United States Patent
Hughes et al.

(10) Patent No.: US 9,868,698 B2
(45) Date of Patent: *Jan. 16, 2018

(54) (2S,4R)-5-(5'-CHLORO-2'-FLUOROBIPHENYL-4-YL)-4-(ETHOXYOXALYLAMINO)-2-HYDROXYMETHYL-2-METHYLPENTANOIC ACID

(71) Applicant: THERAVANCE BIOPHARMA R&D IP, LLC, South San Francisco, CA (US)

(72) Inventors: Adam D. Hughes, Half Moon Bay, CA (US); Erik Fenster, San Bruno, CA (US); Melissa Fleury, Brisbane, CA (US); Anne-Marie Beausoleil, Redwood City, CA (US); Venkat R. Thalladi, Foster City, CA (US); Jerry Nzerem, South San Francisco, CA (US); Miroslav Rapta, San Carlos, CA (US)

(73) Assignee: THERAVANCE BIOPHARMA R&D IP, LLC, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/581,347

(22) Filed: Apr. 28, 2017

(65) Prior Publication Data
US 2017/0355665 A1    Dec. 14, 2017

Related U.S. Application Data

(63) Continuation of application No. 15/229,398, filed on Aug. 5, 2016, now Pat. No. 9,670,143, which is a
(Continued)

(51) Int. Cl.
*C07C 235/74* (2006.01)
(52) U.S. Cl.
CPC ........ *C07C 235/74* (2013.01); *C07B 2200/13* (2013.01)

(58) Field of Classification Search
CPC .......................... C07C 235/74; C07B 2200/13
See application file for complete search history.

(56) References Cited

U.S. PATENT DOCUMENTS 4,189,604 A    2/1980    Umezawa et al.
4,206,232 A    6/1980    Ondetti et al.
(Continued)

FOREIGN PATENT DOCUMENTS

WO    WO 2009/090251 A2    7/2008
WO    WO 2011/088797 A1    7/2011
WO    WO 2014/138053 A1    9/2014

OTHER PUBLICATIONS

Ksander et al., "Dicarboxylic acid dipeptide neutral endopeptidase inhibitors", Journal of Medicinal Chemistry, 38(10): 1689-1700 (1995).

(Continued)

*Primary Examiner* — Trevor Love
(74) *Attorney, Agent, or Firm* — Jeffrey A. Hagenah; Wendy Petka

(57) ABSTRACT

In one aspect, the invention relates to a compound of the structure:

(1)

(Continued)

or a pharmaceutically acceptable salt thereof, and a crystalline form of this compound, having neprilysin inhibition activity. In another aspect, the invention relates to pharmaceutical compositions comprising this compound; methods of using this compound; and processes for preparing this compound.

2 Claims, 5 Drawing Sheets

Related U.S. Application Data continuation of application No. 15/040,481, filed on Feb. 10, 2016, now Pat. No. 9,433,598.

(60) Provisional application No. 62/114,705, filed on Feb. 11, 2015.

(56) References Cited

U.S. PATENT DOCUMENTS

| | | | |
|---|---|---|---|
| 4,374,829 A | 2/1983 | Harris et al. |
| 4,513,009 A | 4/1985 | Rogues et al. |
| 4,722,810 A | 2/1988 | Delaney et al. |
| 4,906,615 A | 3/1990 | Berger et al. |
| 4,929,641 A | 5/1990 | Haslanger et al. |
| 4,939,261 A | 7/1990 | Ksander |
| 4,975,444 A | 12/1990 | Danilewicz et al. |
| 5,021,430 A | 6/1991 | Ksander |
| 5,030,654 A | 7/1991 | Barnish et al. |
| 5,155,100 A | 10/1992 | Erion et al. |
| 5,208,255 A | 5/1993 | Duhamel et al. |
| 5,217,996 A | 6/1993 | Ksander |
| 5,294,632 A | 3/1994 | Erion et al. |
| 5,508,272 A | 4/1996 | Robl |
| 5,599,951 A | 2/1997 | Plaquevent et al. |
| 5,677,297 A | 10/1997 | Waldeck et al. |
| 5,977,075 A | 11/1999 | Ksander et al. |
| 6,602,866 B2 | 8/2003 | Flynn et al. |
| 6,660,756 B2 | 9/2003 | Challenger et al. |
| 8,263,629 B2 | 9/2012 | Coppola et al. |
| 8,394,853 B2 | 3/2013 | Coppola et al. |
| 8,449,890 B2 | 5/2013 | Fleury et al. |
| 8,481,044 B2 | 7/2013 | Fleury et al. |
| 8,513,244 B2 | 8/2013 | Gendron et al. |
| 8,563,512 B2 | 10/2013 | Smith et al. |
| 8,586,536 B2 | 11/2013 | Gendron et al. |
| 8,673,974 B2 | 3/2014 | Coppola et al. |
| 8,686,184 B2 | 4/2014 | Fleury et al. |
| 8,822,534 B2 | 9/2014 | Iwaki et al. |
| 8,871,792 B2 | 10/2014 | Hughes et al. |
| 8,877,938 B2 | 11/2014 | Feng et al. |
| 8,993,631 B2 | 3/2015 | Foo |
| 9,006,249 B2 | 4/2015 | Coppola et al. |
| 9,045,443 B2 | 6/2015 | Mammen et al. |
| 9,108,934 B2 | 8/2015 | Hughes et al. |
| 9,126,956 B2 | 9/2015 | Fleury et al. |
| 2010/0113801 A1 | 5/2010 | Hook et al. |
| 2010/0305131 A1 | 12/2010 | Coppola et al. |
| 2010/0305145 A1 | 12/2010 | Coppola et al. |
| 2011/0124695 A1 | 5/2011 | Iwaki et al. |
| 2012/0122844 A1 | 5/2012 | Foo |
| 2012/0122977 A1 | 5/2012 | Coppola et al. |
| 2012/0309724 A1 | 12/2012 | Fleury et al. |
| 2013/0109639 A1 | 5/2013 | Hughes et al. |
| 2015/0174089 A1 | 6/2015 | Coppola et al. |

OTHER PUBLICATIONS

Misawa et al., "Structure-based design of dipeptide derivatives for the human neutral endopeptidase", Bioorganic & Medicinal Chemistry, 19: 5935-5947 (2011).
International Search Report for PCT/US2012/063036 dated Feb. 13, 2013.
The International Search Report for PCT/US2016/017315 dated Jun. 22, 2016.

(2S,4R)-5-(5'-CHLORO-2'-FLUOROBIPHENYL-4-YL)-4-(ETHOXYOXALYLAMINO)-2-HYDROXYMETHYL-2-METHYLPENTANOIC ACID

CROSS-REFERENCE TO RELATED APPLICATION

This application is a continuation of U.S. application Ser. No. 15/229,398, filed on Aug. 5, 2016, now allowed; which is a continuation of U.S. application Ser. No. 15/040,481, filed on Feb. 10, 2016, now U.S. Pat. No. 9,433,598; which application claims the benefit of U.S. Provisional Application No. 62/114,705, filed on Feb. 11, 2015; the entire disclosures of which are incorporated herein by reference.

BACKGROUND OF THE INVENTION

Field of the Invention

The present invention relates to a novel compound and a crystalline form thereof that are metabolized in vivo to form a compound having utility as a neprilysin-inhibitor. The invention also relates to pharmaceutical compositions comprising compound, processes for preparing this compound, and methods of using compound to treat diseases such as hypertension, heart failure, pulmonary hypertension, and renal disease.

State of the Art

Neprilysin (neutral endopeptidase, EC 3.4.24.11) (NEP), is an endothelial membrane bound $Zn^{2+}$ metallopeptidase found in many organs and tissues, including the brain, kidneys, lungs, gastrointestinal tract, heart, and the peripheral vasculature. NEP degrades and inactivates a number of endogenous peptides, such as enkephalins, circulating bradykinin, angiotensin peptides, and natriuretic peptides, the latter of which have several effects including, for example, vasodilation and natriuresis/diuresis, as well as inhibition of cardiac hypertrophy and ventricular fibrosis. Thus, NEP plays an important role in blood pressure homeostasis and cardiovascular health.

NEP inhibitors, such as thiorphan, candoxatril, and candoxatrilat, have been studied as potential therapeutics. Compounds that inhibit both NEP and angiotensin-I converting enzyme (ACE) are also known, and include omapatrilat, gempatrilat, and sampatrilat. Referred to as vasopeptidase inhibitors, this latter class of compounds is described in Robl et al. (1999) *Exp. Opin. Ther. Patents* 9(12): 1665-1677.

Numerous NEP inhibitors are described in U.S. Patent Application Publication No. 2013/0109639 to Hughes, et al. One such compound is (2S,4R)-5-(5'-chloro-2'-fluorobiphenyl-4-yl)-2-hydroxymethyl-2-methyl-4-(oxalylamino)pentanoic acid, which has the structure:

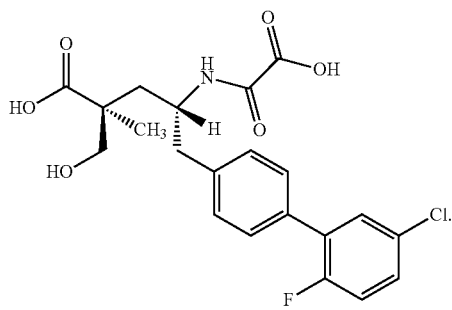

This compound exhibits potent NEP inhibition activity ($pK_i \geq 9$). However, this compound has also been found to have very low oral bioavailability in preclinical species, making it unsuitable or undesirable for oral administration.

One method for increasing the oral bioavailability of a compound is to form a prodrug of the compound. When orally administered, a prodrug should have acceptable oral absorption and be cleaved in vivo to generate the active compound. For NEP inhibitors, it may be preferable that any such prodrug be cleaved rapidly (e.g., within the first hour following oral administration) and completely so that an initial bolus of active compound is available to trigger a cyclic guanosine monophosphate (cGMP) response. It may also be desirable if the prodrug itself has NEP inhibition activity so that the prodrug can contribute to pharmacologic activity before it is cleaved. Moreover, any such prodrug should be chemically stable when stored for a prolonged period of time.

Thus, there exists a need for a prodrug of (2S,4R)-5-(5'-chloro-2'-fluorobiphenyl-4-yl)-2-hydroxymethyl-2-methyl-4-(oxalylamino)pentanoic acid that has acceptable oral absorption and which is rapidly cleaved in vivo to generate the active compound. The prodrug may also have some level of NEP inhibitory activity. This invention is directed to that need.

Additionally, to effectively use a NEP inhibitor compound as a therapeutic agent, it would be desirable to have a solid-state form that can be readily manufactured and that has acceptable chemical and physical stability. For example, it would be highly desirable to have a physical form that is thermally stable at reasonably high temperature, thereby facilitating processing and storage of the material. Crystalline solids are generally preferred over amorphous forms, for enhancing purity and stability of the manufactured product. However, the formation of crystalline forms of organic compounds is highly unpredictable. No reliable methods exist for predicting which, if any, form of an organic compound will be crystalline. Moreover, no methods exist for predicting which, if any, crystalline form will have the physically properties desired for use as pharmaceutical agents. Accordingly, a need exists for a stable, crystalline form which has a reasonably high melting point.

SUMMARY OF THE INVENTION

The present invention provides a novel Compound (1) that is converted in vivo to form a compound that possesses neprilysin (NEP) enzyme inhibition activity. Accordingly, this compound is expected to be useful and advantageous as a therapeutic agent for treating conditions such as hypertension and heart failure.

One aspect of the invention relates to (2S,4R)-5-(5'-chloro-2'-fluorobiphenyl-4-yl)-4-(ethoxyoxalylamino)-2-hydroxymethyl-2-methylpentanoic acid (1):

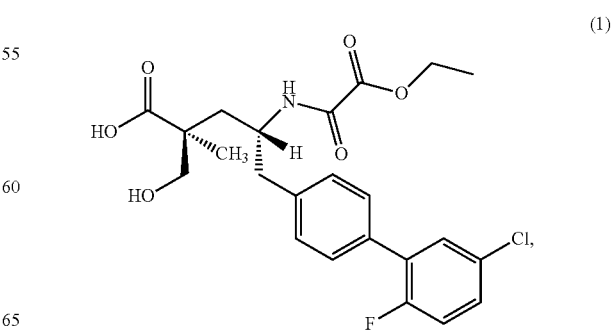

or a pharmaceutically acceptable salt thereof. Another aspect of the invention relates to a crystalline form of Compound 1. In one embodiment, the crystalline form (1') is a hemi-calcium salt of Compound 1.

Another aspect of the invention relates to pharmaceutical compositions comprising one or more pharmaceutically acceptable carriers and Compound 1 or a crystalline form thereof. Such compositions may optionally contain other therapeutic agents, including but not limited to, an $AT_1$ receptor antagonist, an angiotensin-converting enzyme inhibitor, a phosphodiesterase (PDE) inhibitor, a renin inhibitor, a diuretic, or combinations thereof.

Compound 1 possesses NEP enzyme inhibition activity, and is therefore expected to be useful as a therapeutic agent for treating patients suffering from a disease or disorder that is treated by inhibiting the NEP enzyme or by increasing the levels of its peptide substrates. Thus, one aspect of the invention relates to a method of treating patients suffering from a disease or disorder that is treated by inhibiting the NEP enzyme, comprising administering to a patient a therapeutically effective amount of Compound 1. Another aspect of the invention relates to a method of treating hypertension, heart failure, or renal disease, comprising administering to a subject a therapeutically effective amount of Compound 1. Still another aspect of the invention relates to a method for inhibiting a NEP enzyme in a subject comprising administering to the subject, a NEP enzyme-inhibiting amount of Compound 1.

Since Compound 1 possesses NEP inhibition activity, it is also useful as a research tool. Accordingly, one aspect of the invention relates to a method of using Compound 1 as a research tool, the method comprising conducting a biological assay using Compound 1. Compound 1 can also be used to evaluate new chemical compounds. Thus another aspect of the invention relates to a method of evaluating a test compound in a biological assay, comprising: (a) conducting a biological assay with a test compound to provide a first assay value; (b) conducting the biological assay with the compound of the invention to provide a second assay value; wherein step (a) is conducted either before, after or concurrently with step (b); and (c) comparing the first assay value from step (a) with the second assay value from step (b). Exemplary biological assays include a NEP enzyme inhibition assay. Still another aspect of the invention relates to a method of studying a biological system or sample comprising a NEP enzyme, the method comprising: (a) contacting the biological system or sample with the compound of the invention; and (b) determining the effects caused by the compound on the biological system or sample.

Yet another aspect of the invention relates to processes useful for preparing Compound 1 or a crystalline form thereof.

Yet another aspect of the invention relates to the use of Compound 1 or a crystalline form thereof for the manufacture of a medicament, especially for the manufacture of a medicament useful for treating hypertension, heart failure, or renal disease. Another aspect of the invention relates to use of Compound 1 or crystalline form thereof for inhibiting a NEP enzyme in a mammal. Other aspects and embodiments of the invention are disclosed herein.

BRIEF DESCRIPTION OF THE DRAWINGS

Various aspects of the present invention are illustrated by reference to the accompanying drawings.

DETAILED DESCRIPTION OF THE INVENTION

Figure 1:
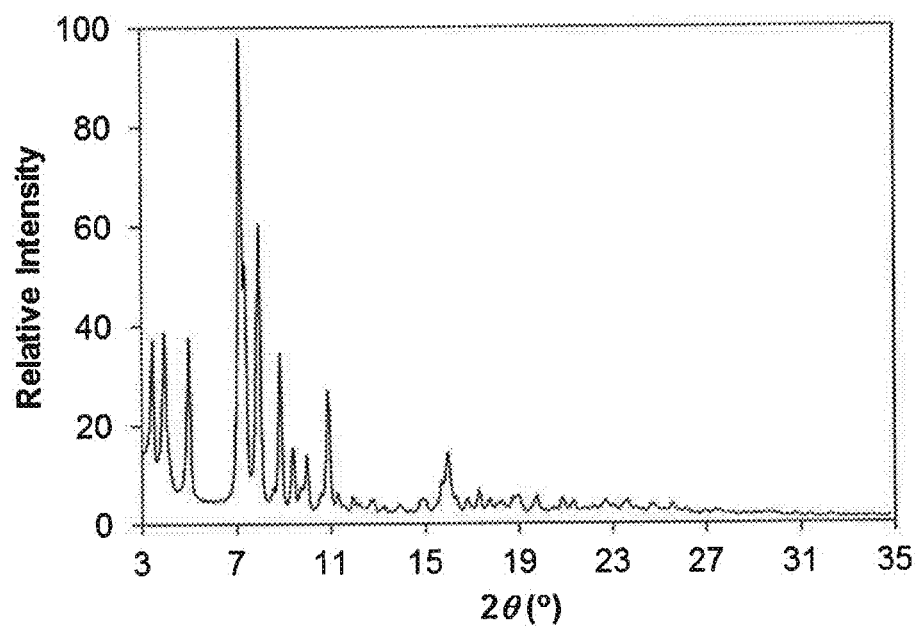
FIG. 1 shows a powder X-ray diffraction (PXRD) pattern of the crystalline form of calcium (2S,4R)-5-(5'-chloro-2'-fluoro-[1,1'-biphenyl]-4-yl)-4-(2-ethoxy-2-oxoacetamido)-2-(hydroxymethyl)-2-methylpentanoate (1').

In one aspect, the invention relates to (2S,4R)-5-(5'-chloro-2'-fluorobiphenyl-4-yl)-4-(ethoxyoxalylamino)-2-hydroxymethyl-2-methylpentanoic acid (1), or a pharmaceutically acceptable salt thereof.

Compound 1 of the invention contains two chiral centers and therefore, this compound may be prepared and used in various stereoisomeric forms. Specifically, the carbon atoms have a particular (R,R), (S,S), (S,R), or (R,S) configuration or are enriched in a stereoisomeric form having such configuration. Compound 1, as shown and named, is in the (S,R) configuration. It will be understood by those skilled in the art that minor amounts of other stereoisomers may be present in the compositions of the invention unless otherwise indicated, provided that the utility of the composition as a whole is not eliminated by the presence of such other isomers. Individual stereoisomers may be obtained by numerous methods that are well known in the art, including chiral chromatography using a suitable chiral stationary phase or support, or by chemically converting them into diastereoisomers, separating the diastereoisomers by conventional means such as chromatography or recrystallization, then regenerating the original stereoisomer.

Compound 1 is an ethyl ester prodrug, where the ethyl moiety serves to improve the compound's lipophilicity, and therefore improve the passive membrane permeability of the active compound by masking the carboxylic acid. Once in the body, it is believed that this ester bond is hydrolyzed by esterases that are found in the blood, liver and other organs and tissues.

Compound 1 of the invention has been found to inhibit the neprilysin (NEP) enzyme. In addition, the compound possesses greater potency for NEP inhibition once it is metabolized in vivo. Thus, when discussing the activity of the compound of the invention, it is understood that the compound may exhibit a certain level of activity in an assay and an improved level of activity once metabolized to its active form. One measure of the ability of a compound to inhibit NEP activity is the inhibition constant ($pK_i$). The $pK_i$ value is the negative logarithm to base 10 of the dissociation constant ($K_i$), which is typically reported in molar units. Compound 1, when metabolized, forms (2S,4R)-5-(5'-chloro-2'-fluorobiphenyl-4-yl)-2-hydroxymethyl-2-methyl-4-(oxalylamino)pentanoic acid (the "active agent or active metabolite"), which is reported in U.S. Patent Application Publication No. 2013/0109639 as having a $pK_i$ at NEP≥9. Other properties and utilities of Compound 1 can be demonstrated using in vitro and in vivo assays that are well-known to those skilled in the art, including, inter alia, those described in U.S. Patent Application Publication No. 2013/0109639.

Compound 1, as well as those compounds used in its synthesis, may also include isotopically-labeled compounds, that is, where one or more atoms have been enriched with atoms having an atomic mass different from the atomic mass predominately found in nature. Examples of isotopes that may be incorporated into the compounds of formula I, for example, include, but are not limited to, $^2H$, $^3H$, $^{13}C$, $^{14}C$, $^{15}N$, $^{18}O$, $^{17}O$, $^{35}S$, $^{36}Cl$, and $^{18}F$. Of particular interest is Compound 1 enriched in tritium or carbon-14 which can be used, for example, in tissue distribution studies; Compound 1 enriched in deuterium especially at a site of metabolism resulting, for example, in a compound having greater metabolic stability; and Compound 1 enriched in a positron emitting isotope, such as $^{11}C$, $^{18}F$, $^{15}O$ and $^{13}N$, which can be used, for example, in Positron Emission Topography (PET) studies.

Chemical structures are named herein according to IUPAC conventions as implemented in ChemDraw software (Perkin Elmer, Inc., Cambridge, Mass.).

Definitions

When describing the compound, compositions, methods and processes of the invention, the following terms have the following meanings unless otherwise indicated. Additionally, as used herein, the singular forms "a," "an," and "the" include the corresponding plural forms unless the context of use clearly dictates otherwise. The terms "comprising", "including," and "having" are intended to be inclusive and mean that there may be additional elements other than the listed elements. All numbers expressing quantities of ingredients, properties such as molecular weight, reaction conditions, and so forth used herein are to be understood as being modified in all instances by the term "about," unless otherwise indicated. Accordingly, the numbers set forth herein are approximations that may vary depending upon the desired properties sought to be obtained by the present invention. At least, and not as an attempt to limit the application of the doctrine of equivalents to the scope of the claims, each number should at least be construed in light of the reported significant digits and by applying ordinary rounding techniques.

The term "about" or "approximately" when used in the context of thermal behavior of Compound 1 is defined as ±1-3° C. The term "approximate" when used in the context of % dose of Compound 1 excreted in the urine is defined by a margin of error that is typically about twice the standard deviation or the half-width of a 95 percent confidence interval. The term "approximate" in other areas of the disclosure may be used to indicate standard deviation or the amount of variation or dispersion of a set of data values.

The term "controlled-release" as used herein is synonymous with sustained-release and extended-release and relates to amount of drug delivered over extended period of time in a subject. Generally, controlled-release tablets and capsules release the active compound into the subject over time periods of about 8-, 12-, 16-, and 24-hours. On the other hand, the term "immediate-release" refers to the active compound being released in a subject within a small period of time, typically less than about 30 minutes. The term "delayed-release" is directed to tablets and capsules that release the pharmaceutical dose after a set period of time. These dosage forms are usually enteric-coated in order to prevent release in the stomach but allow the release in the intestinal track.

As used herein, the phrase "of the formula" or "having the formula" or "having the structure" is not intended to be limiting and is used in the same way that the term "comprising" is commonly used. For example, if one structure is depicted, it is understood that all stereoisomer and tautomer forms are encompassed, unless stated otherwise.

In general, in describing pharmaceutical solids, the term "calcium (2S,4R)-5-(5'-chloro-2'-fluoro-[1,1'-biphenyl]-4-yl)-4-(2-ethoxy-2-oxoacetamido)-2-(hydroxymethyl)-2-methylpentanoate" implies an approximate 2:1 stoichiometric amount of the carboxylate anion of Compound 1 to calcium counterion. The term hemi-calcium salt of Compound 1 is equivalent to the calcium salt of Compound 1. In one embodiment of the invention, crystalline form of Compound 1' is a non-hydroscopic solid.

The term "melting point" as used herein means the temperature at which the maximum endothermic heat flow is observed by differential scanning calorimetry, for the thermal transition that corresponds to the solid-to-liquid phase change.

The term "pharmaceutically acceptable" refers to a material that is not biologically or otherwise unacceptable when used in the invention. For example, the term "pharmaceutically acceptable carrier" refers to a material that can be incorporated into a composition and administered to a patient without causing unacceptable biological effects or interacting in an unacceptable manner with other components of the composition. Such pharmaceutically acceptable materials typically have met the required standards of toxicological and manufacturing testing, and include those materials identified as suitable inactive ingredients by the U.S. Food and Drug administration.

The term "pharmaceutically acceptable salt" means a salt prepared from a base or an acid which is acceptable for administration to a patient, such as a mammal (for example, salts having acceptable mammalian safety for a given dosage regime). However, it is understood that the salts covered by the invention are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a compound contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (for example, citric, gluconic, glycolic, lactic, lactobionic, malic, and tartaric acids), aliphatic monocarboxylic acids (for example, acetic, butyric, formic, propionic and trifluoroacetic acids), amino acids (for example, aspartic and glutamic acids), aromatic carboxylic acids (for example, benzoic, p-chlorobenzoic, diphenylacetic, gentisic, hippuric, and triphenylacetic acids), aromatic hydroxyl acids (for example, o-hydroxybenzoic, p-hydroxybenzoic, 1-hydroxynaphthalene-2-carboxylic and 3-hydroxynaphthalene-2-carboxylic acids), ascorbic, dicarboxylic acids (for example, fumaric, maleic, oxalic and succinic acids), glucoronic, mandelic, mucic, nicotinic, orotic, pamoic, pantothenic, sulfonic acids (for example, benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like.

The term "therapeutically effective amount" means an amount sufficient to effect treatment when administered to a patient in need thereof, that is, the amount of drug needed to obtain the desired therapeutic effect. For example, a therapeutically effective amount for treating hypertension is an amount of compound needed to, for example, reduce, suppress, eliminate, or prevent the symptoms of hypertension, or to treat the underlying cause of hypertension. In one embodiment, a therapeutically effective amount is that amount of drug needed to reduce blood pressure or the amount of drug needed to maintain normal blood pressure. On the other hand, the term "effective amount" means an amount sufficient to obtain a desired result, which may not necessarily be a therapeutic result. For example, when studying a system comprising a NEP enzyme, an "effective amount" may be the amount needed to inhibit the enzyme.

The term "treating" or "treatment" as used herein means the treating or treatment of a disease or medical condition (such as hypertension) in a patient, such as a mammal (particularly a human) that includes one or more of the following: (a) preventing the disease or medical condition from occurring, i.e., preventing the reoccurrence of the disease or medical condition or prophylactic treatment of a patient that is pre-disposed to the disease or medical condition; (b) ameliorating the disease or medical condition, i.e., eliminating or causing regression of the disease or medical condition in a patient; (c) suppressing the disease or medical condition, i.e., slowing or arresting the development of the disease or medical condition in a patient; or (d) alleviating the symptoms of the disease or medical condition in a patient. For example, the term "treating hypertension" would include preventing hypertension from occurring, ameliorating hypertension, suppressing hypertension, and alleviating the symptoms of hypertension (for example, lowering blood pressure). The term "subject" or "patient" is intended to include those mammals, such as humans, that are in need of treatment or disease prevention or that are presently being treated for disease prevention or treatment of a specific disease or medical condition, as well as test subjects in which the crystalline compound is being evaluated or being used in an assay, for example an animal model.

All other terms used herein are intended to have their ordinary meaning as understood by those of ordinary skill in the art to which they pertain.

General Synthetic Procedures

Compound 1 and its crystalline calcium salt form can be synthesized from readily available starting materials as described below and in the Examples. It will be appreciated that where typical or preferred process conditions (i.e., reaction temperatures, times, mole ratios of reactants, solvents, pressures, etc.) are given, other process conditions can also be used unless otherwise stated. It will be appreciated that while specific process conditions (i.e., crystallization temperatures, times, mole ratios of reactants, solvents, pressures, etc.) are given, other process conditions can also be used unless otherwise stated. In some instances, reactions or crystallizations were conducted at room temperature and no actual temperature measurement was taken. It is understood that room temperature can be taken to mean a temperature within the range commonly associated with the ambient temperature in a laboratory environment, and will typically be in the range of about 15° C. to about 30° C., such as about 20° C. to about 25° C. In other instances, reactions or crystallizations were conducted at room temperature and the temperature was actually measured and recorded.

Any molar ratios described in the methods of the invention can be readily determined by various methods available to those skilled in the art. For example, such molar ratios can be readily determined by $^1$H NMR. Alternatively, elemental analysis and HPLC methods can be used to determine the molar ratio.

In one embodiment, the invention relates to (2S,4R)-5-(5'-chloro-2'-fluorobiphenyl-4-yl)-4-(ethoxyoxalylamino)-2-hydroxymethyl-2-methylpentanoic acid (1), or a pharmaceutically acceptable salt thereof.

In another embodiment, Compound 1 can be prepared by mixing ethanol and oxalyl chloride to form a solution, reacting (2S,4R)-4-amino-5-(5'-chloro-2'-fluorobiphenyl-4-yl)-2-hydroxymethyl-2-methylpentanoic acid benzyl ester with the solution, and combining resulting mixture with palladium on carbon under hydrogen.

In yet another embodiment, Compound 1 can be prepared by (a) dissolving ethanol in dichloromethane; (b) adding oxalyl chloride to form a solution and stirring at room temperature; (c) evaporating solvent from solution; (d) adding remaining solution to (2S,4R)-4-amino-5-(5'-chloro-2'-fluorobiphenyl-4-yl)-2-hydroxymethyl-2-methylpentanoic acid benzyl ester that is first dissolved in dichloromethane; (e) adding N,N-diisopropylethylamine and stirring a room temperature; (0 evaporating solvent to form a solid; (g) combining solid with palladium 10 wt % on carbon in solvent to form a mixture; (h) placing mixture under hydrogen with stirring; and (i) filtering off palladium on carbon and vacuum drying to form solid Compound 1. The resulting solids in steps (0 and (i) may also be purified by chromatography.

Preparation of the crystalline hemi-calcium salt of Compound 1 is generally conducted in a suitable inert diluent, examples of which include, but are not limited to, acetone, acetonitrile, ethyl acetate, methyl ethyl ketone, methanol, ethanol, isopropanol, isobutanol, dichloromethane, methyl t-butyl ether, cyclopentyl methyl ether, hexanes, and the like, and mixtures thereof, optionally containing water. Mixtures of inert diluents (also referred to as solvent systems) include acetone with water, acetonitrile with water, ethanol and ethyl acetate, ethyl acetate and hexanes, and lower alcohols ($C_{1-6}$alkyl-OH) with water, for example, methanol and water and isopropanol and water. Particularly suitable solvent systems include ethanol, ethanol:water and ethyl acetate:ethanol containing calcium propionate or other calcium salts. Upon completion of the crystallization, the crystalline compound can be isolated from the reaction mixture by any conventional means such as precipitation, filtration, concentration, centrifugation, dried in vacuo, and the like.

In one embodiment, the invention relates to a crystalline form of (2S,4R)-5-(5'-chloro-2'-fluorobiphenyl-4-yl)-4-(ethoxyoxalylamino)-2-hydroxymethyl-2-methylpentanoic acid. In another embodiment, the crystalline form is calcium (2S,4R)-5-(5'-chloro-2'-fluoro-[1,1'-biphenyl]-4-yl)-4-(2-ethoxy-2-oxoacetamido)-2-(hydroxymethyl)-2-methylpentanoate (1').

In another embodiment, the crystalline form 1' can be prepared by (a) dissolving (2S,4R)-5-(5'-chloro-2'-fluorobiphenyl-4-yl)-4-(ethoxyoxalylamino)-2-hydroxymethyl-2-methylpentanoic acid in ethanol and N,N-diisopropylethylamine to form solution A; (b) dissolving calcium trifluoromethane sulfonate in ethanol to form solution B; (c) adding dropwise solution B to solution A to form a slurry; (d) stirring at room temperature; and (e) isolating the resulting solids to yield Compound 1'. Another embodiment includes a second crystallization step. Here, the second recrystallization process further comprises (f) cooling Compound 1' to about 5° C. and adding a cold ethanol:water mixture under vigorous stirring; and (g) filtering and drying at room temperature to yield Compound 1'.

Crystalline Properties

As is well known in the field of powder X-ray diffraction (PXRD) analysis, relative peak heights of PXRD patterns are dependent on a number of factors relating to sample preparation and instrument geometry, while peak positions are relatively insensitive to experimental details. PXRD, differential scanning calorimetry (DSC), thermogravimetric analyses (TGA), and dynamic moisture sorption (DMS) assessment (also known as moisture sorption-desorption analysis) were performed as described herein.

In one aspect, the invention relates to (2S,4R)-5-(5'-chloro-2'-fluorobiphenyl-4-yl)-4-(ethoxyoxalylamino)-2-hydroxymethyl-2-methylpentanoic acid in crystalline form. In another aspect, the crystalline form is calcium (2S,4R)-5-(5'-chloro-2'-fluoro-[1,1'-biphenyl]-4-yl)-4-(2-ethoxy-2-oxoacetamido)-2-(hydroxymethyl)-2-methylpentanoate (1'). This crystalline form 1' is characterized by a PXRD pattern in which the peak positions are substantially in accordance with those shown in FIG. 1. Peaks with relative intensities greater than 0.1% in area are listed in the table below. This pattern shows sharp diffraction peaks in the range 3-25° in 2θ.

| 2θ* | d (Å) | Area | Area % |
|---|---|---|---|
| 3.47 | 25.45 | 1577.40 | 16.30 |
| 3.98 | 22.20 | 2084.20 | 21.50 |
| 5.00 | 17.67 | 2012.20 | 20.70 |
| 7.18 | 12.31 | 7729.90 | 79.70 |
| 7.38 | 11.97 | 9698.10 | 100.00 |
| 7.97 | 11.08 | 4616.90 | 47.60 |
| 8.57 | 10.32 | 318.10 | 3.30 |
| 8.87 | 9.96 | 1860.30 | 19.20 |
| 9.42 | 9.38 | 708.30 | 7.30 |
| 9.99 | 8.85 | 876.80 | 9.00 |
| 10.60 | 8.34 | 333.50 | 3.40 |
| 10.91 | 8.11 | 2013.70 | 20.80 |
| 11.58 | 7.63 | 22.40 | 0.20 |
| 11.95 | 7.40 | 194.00 | 2.00 |
| 12.19 | 7.25 | 269.10 | 2.80 |
| 14.86 | 5.96 | 297.90 | 3.10 |
| 15.74 | 5.63 | 1294.90 | 13.40 |
| 15.98 | 5.54 | 1659.40 | 17.10 |
| 16.31 | 5.43 | 235.70 | 2.40 |
| 17.29 | 5.13 | 264.50 | 2.70 |
| 18.98 | 4.67 | 394.80 | 4.10 |
| 19.75 | 4.49 | 295.50 | 3.00 |
| 20.83 | 4.26 | 255.70 | 2.60 |
| 22.69 | 3.92 | 276.20 | 2.80 |
| 23.58 | 3.77 | 279.20 | 2.90 |

*2θ values are reported as value ± 0.20.

Thus, in one embodiment, crystalline form 1' is characterized by a PXRD pattern comprising diffraction peaks at 2θ values of 7.18±0.2, 7.38±0.2 and 7.97±0.2.

In another embodiment, crystalline form 1' is characterized by a PXRD pattern comprising diffraction peaks at 2θ values of 3.98±0.2, 5.00±0.2, 7.18±0.2, 7.38±0.2, 7.97±0.2, 8.87±0.2, and 10.91±0.2.

In another embodiment, crystalline form V is further characterized by having one or more additional diffraction peaks at 2θ values selected from 3.47±0.2, 9.99±0.2, 15.74±0.2, 15.98±0.2, and 18.98±0.2; and in yet another embodiment crystalline form 1' is further characterized by having three or more such additional diffraction peaks.

Figure 2:
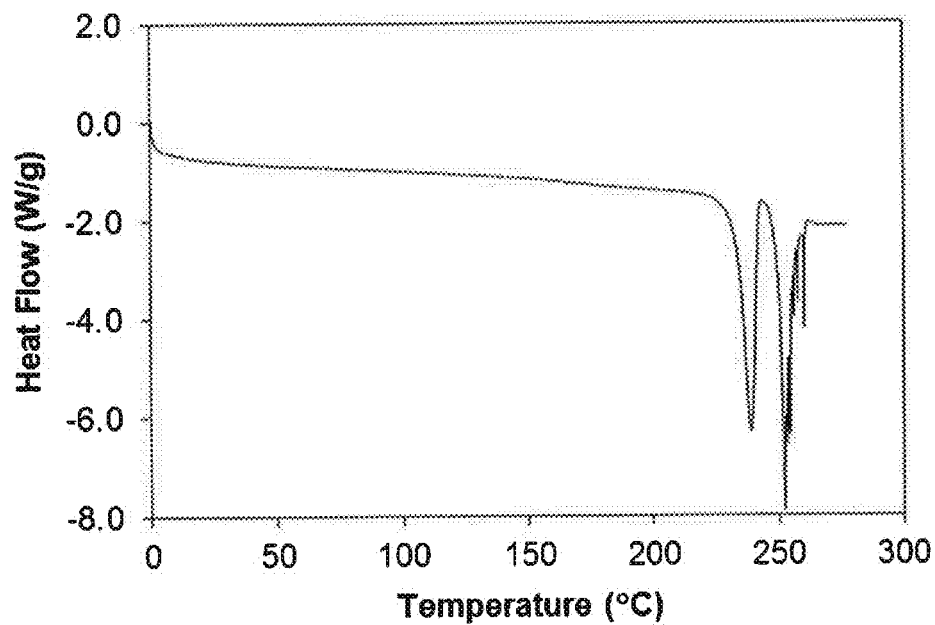
FIG. 2 shows a differential scanning calorimetry (DSC) thermogram of the crystalline form of calcium (2S,4R)-5-(5'-chloro-2'-fluoro-[1,1'-biphenyl]-4-yl)-4-(2-ethoxy-2-oxoacetamido)-2-(hydroxymethyl)-2-methylpentanoate (1').

In one embodiment, crystalline form 1' is characterized by the DSC thermogram substantially in accordance with that shown in FIG. 2. The crystalline form 1' is characterized by a DSC trace recorded at a heating rate of 10° C. per minute which shows a maximum in endothermic heat flow at a temperature between about 237° C. and about 241° C. The DSC thermogram illustrates a melting endotherm with a peak at approximately 239° C., onset at 233° C., and with an enthalpy of ~67 J/g. A second endotherm embodies decomposition and other unknown thermal events.

Figure 3:
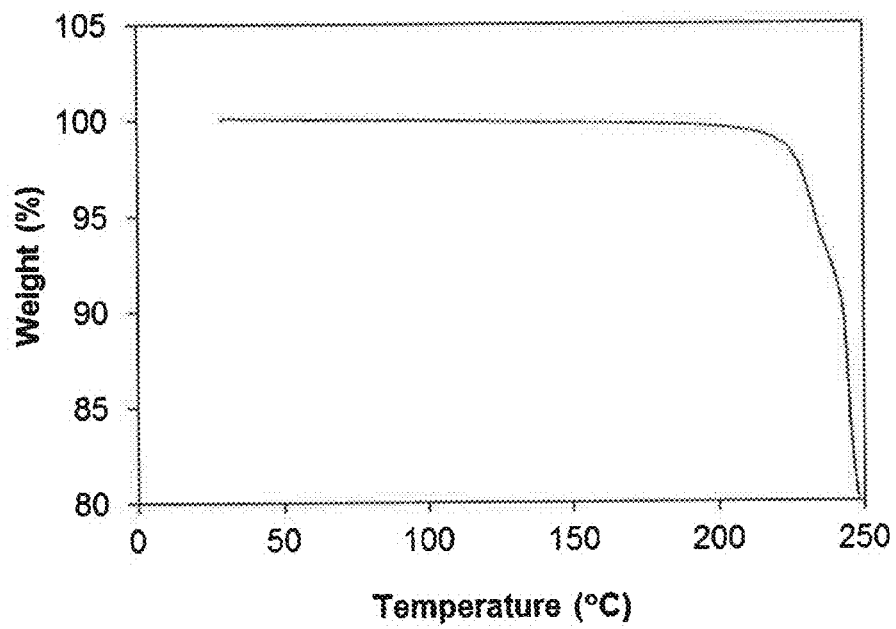
FIG. 3 shows a thermal gravimetric analysis (TGA) plot for of the crystalline form of calcium (2S,4R)-5-(5'-chloro-2'-fluoro-[1,1'-biphenyl]-4-yl)-4-(2-ethoxy-2-oxoacetamido)-2-(hydroxymethyl)-2-methylpentanoate (1').

In one embodiment, the crystalline form V is characterized by the TGA plot in FIG. 3. The TGA plot shows onset of decomposition at a temperature of about 225° C. The crystalline compound decomposes after melting, as seen by significant weight loss after ~250° C., which also corresponds to a second endotherm in the DSC trace.

Figure 4:
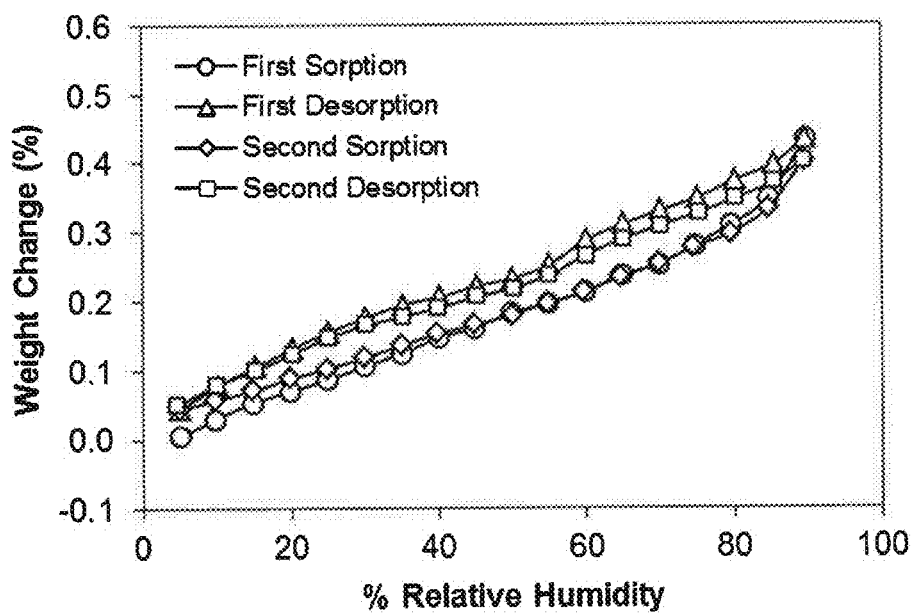
FIG. 4 shows a dynamic moisture sorption (DMS) isotherm of the crystalline form of calcium (2S,4R)-5-(5'-chloro-2'-fluoro-[1,1'-biphenyl]-4-yl)-4-(2-ethoxy-2-oxoacetamido)-2-(hydroxymethyl)-2-methylpentanoate (1').

In one embodiment, crystalline form 1' is characterized by the DMS isotherm in FIG. 4. This form is a non-hygroscopic solid. The total moisture gain observed is less than 1% by weight when exposed to between 5% and 90% relative humidity. No significant hysteresis is found between consecutive sorption-desorption cycles. The solid obtained after sorption-desorption cycles showed the same PXRD pattern as the starting material, indicating no change in form after this experiment.

Figure 5:
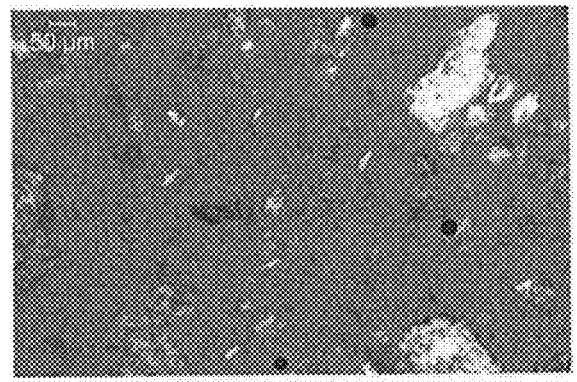
FIG. 5 is a polarized light microscopic (PLM) image of the crystalline form of calcium (2S,4R)-5-(5'-chloro-2'-fluoro-[1,1'-biphenyl]-4-yl)-4-(2-ethoxy-2-oxoacetamido)-2-(hydroxymethyl)-2-methylpentanoate (1').

The crystalline form 1' can be characterized by the PLM image in FIG. 5, which shows this form as being thin birefringent crystals.

Figure 8:
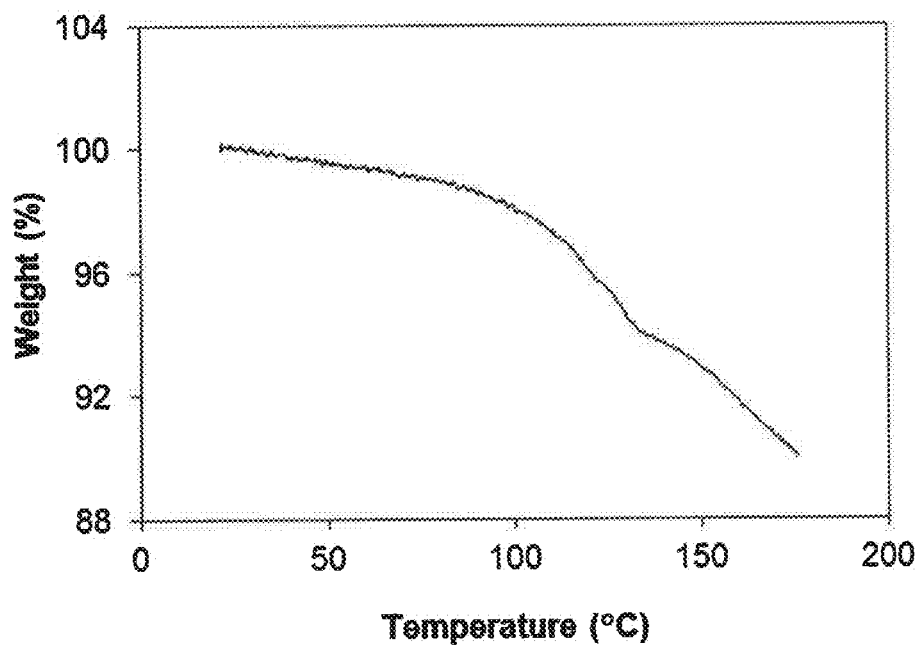
FIG. 8 shows a thermal gravimetric analysis (TGA) plot for of the crystalline form of arginine (2S,4R)-5-(5'-chloro-2'-fluoro-[1,1'-biphenyl]-4-yl)-4-(2-ethoxy-2-oxoacetamido)-2-(hydroxymethyl)-2-methylpentanoate (1").
Figure 9:
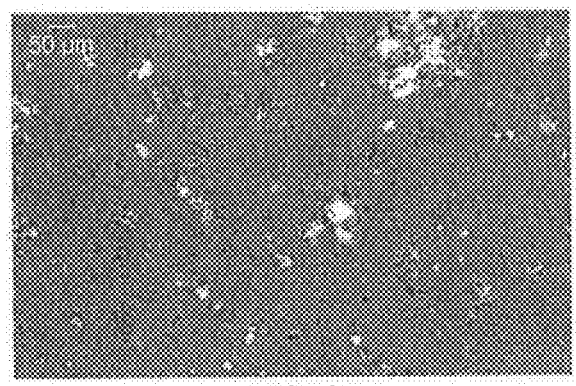
FIG. 9 is a polarized light microscopic (PLM) image of the crystalline form of arginine (2S,4R)-5-(5'-chloro-2'-fluoro-[1,1'-biphenyl]-4-yl)-4-(2-ethoxy-2-oxoacetamido)-2-(hydroxymethyl)-2-methylpentanoate (1").

Crystals of L-arginine (2S,4R)-5-(5'-chloro-2'-fluoro-[1,1'-biphenyl]-4-yl)-4-(2-ethoxy-2-oxoacetamido)-2-(hydroxymethyl)-2-methylpentanoate (1") were also prepared. However, exposing these crystals to ambient conditions led to slow deliquescence. The crystalline form 1" is characterized by a PXRD and a DSC trace in FIGS. 6 and 7, respectively. The DSC trace was recorded at a heating rate of 10° C. per minute and shows a maximum in endothermic heat flow at a temperature between about 113° C. and about 117° C. The DSC thermogram illustrates a melting endotherm with a peak at approximately 116.9° C., onset at 106.8° C., and with an enthalpy of ~70.3 J/g. Crystalline form 1" is also characterized by the TGA plot in FIG. 8, where ~6.5% weight loss was observed up until 140° C. and a continued loss of mass is observed after 140° C. Crystalline form 1" can be characterized by the PLM image in FIG. 9, which shows this form as being thin birefringent crystals.

Utility

The in vitro-to-in vivo extrapolation of drug behavior in a subject continues to improve (see, e.g., Chiba et al., AAPS J., 2009 June; 11(2): 262-276). In the present invention, in vitro human neprilysin inhibitor activity was assessed (Assay 1) in order to determine neprilysin inhibitory activity of Compound 1. A threshold of $pK_i \geq 9.0$ was met for this compound. However, additional in vivo experiments were further performed in order to more accurately predict the behavior of Compound 1 in a subject.

A critical parameter in evaluating the suitability of a prodrug is the determination of how rapidly the prodrug is converted to the active agent or active metabolite. In the present invention, Compound 1, being an ester prodrug, is converted to the active agent or active metabolite, Comparison Compound C2, by an enzymatic reaction, e.g., esterase hydrolysis, which can be highly species-dependent. For that reason, it is preferable to evaluate conversion rates in multiple species when extrapolating to human subjects. Additionally, there are several properties that useful in evaluating whether a sufficient amount of the drug will be delivered to the plasma in order to achieve the necessary therapeutic benefit, for example, high oral bioavailability and low renal clearance for those subjects with compromised kidney function.

For the present invention, oral and intravenous pharmacokinetic studies were conducted in rat, dog, and monkey species in order to determine the oral bioavailability of the Compound 1 as compared to active metabolite Comparison Compound C2 (Assay 2). Additionally, oral and intravenous pharmacokinetic studies were conducted in rat and dog species in order to compare Compound 1 with other chemically similar ester prodrugs or compounds (Assay 3).

Compound 1 inhibits the NEP enzyme, and therefore is expected to be useful for the treatment and/or prevention of medical conditions responsive to NEP inhibition. Thus it is expected that patients suffering from a disease or disorder that is treated by inhibiting the NEP enzyme or by increasing the levels of its peptide substrates, can be treated by administering a therapeutically effective amount of Compound 1. For example, by inhibiting NEP, Compound 1 is expected to potentiate the biological effects of endogenous peptides that are metabolized by NEP, such as the natriuretic peptides, bombesin, bradykinins, calcitonin, endothelins, enkephalins, neurotensin, substance P and vasoactive intestinal peptide. Thus, this compound is expected to have other physiological actions, for example, on the renal, central nervous, reproductive and gastrointestinal systems.

Drugs are removed from a subject body by various elimination processes which are categorized generally as excretion and biotransformation. Excretion relates to the removal of the intact non-volatile drug mainly by renal (kidney) to bladder to urine while other pathways of excretion include bile (liver), sweat, saliva, milk (via lactation) or other bodily fluids. Volatile drugs like alcohol and gaseous anesthetics are excreted via the lungs into expired air. On the other hand, biotransformation, or drug metabolism, relates to a drug being chemically converted in the body to a metabolite and is usually an enzymatic process. Exception to this is when a drug is chemically changed non-enzymatically, e.g., ester hydrolysis. Enzymes involved in biotransformation of drugs are located mainly in the liver. Other tissues such as kidney, lung, small intestine and skin also contain metabolic enzymes.

Pharmacokinetic studies can also be used to investigate elimination pathways in a subject, e.g., renal clearance via excretion of the administered drug in urine over time. The renal excretion of Compound 1 in a dog model was conducted to assess kidney excretion as an elimination pathway (Assay 4). This elimination pathway is important for subjects that have compromised kidney function and need therapies that are minimally cleared by kidney excretion. In one embodiment, the renal excretion of Compound 1 or crystalline form thereof in the subject is approximately ≤15%, ≤10%, ≤5%, ≤3%, ≤2%, ≤1% or ≤0.5% of the administered dose over 24 hours.

As described in the assay section below, included along with Compound 1 in an in vitro NEP enzyme assay, and in in vivo determinations of oral bioavailability and renal excretion in multiple animal species, were comparator compounds of similar chemical structure. Surprisingly, significant differences in results were observed. While individual comparator compounds exhibited properties, similar to those of Compound 1 in one or more assays, only Compound 1 exhibited, at the same time, high inhibitory activity of human neprilysin, high oral bioavailability, and low renal excretion expected to lead to particular utility in the treatment of disease.

Additionally, to effectively use Compound 1 as a therapeutic agent, it is desirable to have a solid-state form of this compound that can be readily manufactured and that has acceptable chemical and physical stability, including a high melting point. Crystals of the free acid of Compound 1 could not be obtained. Arginine and calcium crystals of Compound 1 were ultimately made but the arginine crystals were deliquescent at ambient conditions and were difficult to develop further. On the other hand, the calcium crystals were stable and melted around 239° C. and may be used for further development as a therapeutic agent.

Cardiovascular Diseases

By potentiating the effects of vasoactive peptides like the natriuretic peptides and bradykinin, Compound 1 is expected to find utility in treating and/or preventing medical conditions such as cardiovascular diseases. See, for example, Rogues et al. (1993) *Pharmacol. Rev.* 45:87-146 and Dempsey et al. (2009) *Amer. J. of Pathology* 174(3): 782-796. Cardiovascular diseases of particular interest include hypertension and heart failure. Hypertension includes, by way of illustration and not limitation: primary hypertension, which is also referred to as essential hypertension or idiopathic hypertension; secondary hypertension; hypertension with accompanying renal disease; severe hypertension with or without accompanying renal disease;

pulmonary hypertension, including pulmonary arterial hypertension; and resistant hypertension. Heart failure includes, by way of illustration and not limitation: congestive heart failure; acute heart failure; chronic heart failure, for example with reduced left ventricular ejection fraction (also referred to as systolic heart failure) or with preserved left ventricular ejection fraction (also referred to as diastolic heart failure); and acute and chronic decompensated heart failure. Thus, one embodiment of the invention relates to a method for treating hypertension, particularly primary hypertension or pulmonary arterial hypertension, comprising administering to a patient a therapeutically effective amount of Compound 1.

For treatment of primary hypertension, the therapeutically effective amount is typically the amount that is sufficient to lower the patient's blood pressure. This would include both mild-to-moderate hypertension and severe hypertension. When used to treat hypertension, Compound 1 may be administered in combination with other therapeutic agents such as aldosterone antagonists, aldosterone synthase inhibitors, angiotensin-converting enzyme inhibitors and dual-acting angiotensin-converting enzyme/neprilysin inhibitors, angiotensin-converting enzyme 2 (ACE2) activators and stimulators, angiotensin-II vaccines, anti-diabetic agents, anti-lipid agents, anti-thrombotic agents, $AT_1$ receptor antagonists and dual-acting $AT_1$ receptor antagonist/neprilysin inhibitors, $\beta_1$-adrenergic receptor antagonists, dual-acting $\beta$-adrenergic receptor antagonist/$\alpha_1$-receptor antagonists, calcium channel blockers, diuretics, endothelin receptor antagonists, endothelin converting enzyme inhibitors, neprilysin inhibitors, natriuretic peptides and their analogs, natriuretic peptide clearance receptor antagonists, nitric oxide donors, non-steroidal anti-inflammatory agents, phosphodiesterase inhibitors (specifically PDE-V inhibitors), prostaglandin receptor agonists, renin inhibitors, soluble guanylate cyclase stimulators and activators, and combinations thereof. In one particular embodiment of the invention, the compound of the invention is combined with an $AT_1$ receptor antagonist, a calcium channel blocker, a diuretic, or a combination thereof, and used to treat primary hypertension. In another particular embodiment of the invention, the compound of the invention is combined with an $AT_1$ receptor antagonist, and used to treat hypertension with accompanying renal disease. When used to treat resistant hypertension, the compound may be administered in combination with other therapeutic agents such as aldosterone synthase inhibitors.

For treatment of pulmonary arterial hypertension, the therapeutically effective amount is typically the amount that is sufficient to lower the pulmonary vascular resistance. Other goals of therapy are to improve a patient's exercise capacity. For example, in a clinical setting, the therapeutically effective amount can be the amount that improves a patient's ability to walk comfortably for a period of 6 minutes (covering a distance of approximately 20-40 meters). When used to treat pulmonary arterial hypertension the compound may be administered in combination with other therapeutic agents such as α-adrenergic receptor antagonists, $\beta_1$-adrenergic receptor antagonists, $\beta_2$-adrenergic receptor agonists, angiotensin-converting enzyme inhibitors, anticoagulants, calcium channel blockers, diuretics, endothelin receptor antagonists, PDE-V inhibitors, prostaglandin analogs, selective serotonin reuptake inhibitors, and combinations thereof. In one particular embodiment of the invention, Compound 1 is combined with a PDE-V inhibitor or a selective serotonin reuptake inhibitor and used to treat pulmonary arterial hypertension.

Another embodiment of the invention relates to a method for treating heart failure, in particular congestive heart failure (including both systolic and diastolic congestive heart failure), comprising administering to a patient a therapeutically effective amount of Compound 1. Typically, the therapeutically effective amount is the amount that is sufficient to lower blood pressure and/or improve renal functions. In a clinical setting, the therapeutically effective amount can be the amount that is sufficient to improve cardiac hemodynamics, like for instance reduction in wedge pressure, right atrial pressure, filling pressure, and vascular resistance. In one embodiment, Compound 1 is administered as an intravenous dosage form. When used to treat heart failure, the compound may be administered in combination with other therapeutic agents such as adenosine receptor antagonists, advanced glycation end product breakers, aldosterone antagonists, $AT_1$ receptor antagonists, $\beta_1$-adrenergic receptor antagonists, dual-acting $\beta$-adrenergic receptor antagonist/$\alpha_1$-receptor antagonists, chymase inhibitors, digoxin, diuretics, endothelin converting enzyme (ECE) inhibitors, endothelin receptor antagonists, natriuretic peptides and their analogs, natriuretic peptide clearance receptor antagonists, nitric oxide donors, prostaglandin analogs, PDE-V inhibitors, soluble guanylate cyclase activators and stimulators, and vasopressin receptor antagonists. In one particular embodiment of the invention, Compound 1 is combined with an aldosterone antagonist, a $\beta_1$-adrenergic receptor antagonist, an $AT_1$ receptor antagonist, or a diuretic, and used to treat congestive heart failure.

Diarrhea

As a NEP inhibitor, the Compound 1 is expected to inhibit the degradation of endogenous enkephalins and thus such compounds may also find utility for the treatment of diarrhea, including infectious and secretory/watery diarrhea. See, for example, Baumer et al. (1992) Gut 33:753-758; Farthing (2006) Digestive Diseases 24:47-58; and Marçais-Collado (1987) Eur. J. Pharmacol. 144(2):125-132. When used to treat diarrhea, Compound 1 may be combined with one or more additional antidiarrheal agents.

Renal Diseases

By potentiating the effects of vasoactive peptides like the natriuretic peptides and bradykinin, Compound 1 is expected to enhance renal function (see Chen et al. (1999) Circulation 100:2443-2448; Lipkin et al. (1997) Kidney Int. 52:792-801; and Dussaule et al. (1993) Clin. Sci. 84:31-39) and find utility in treating and/or preventing renal diseases in a renally-impaired subject. Renal diseases of particular interest include diabetic nephropathy, chronic kidney disease, proteinuria, and particularly acute kidney injury (caused, for example, by cardiovascular surgery, chemotherapy, or the use of contrast dyes in medical imaging) or acute renal failure (see Sharkovska et al. (2011) Clin. Lab. 57:507-515 and Newaz et al. (2010) Renal Failure 32:384-390).

A renally-impaired subject that has chronic kidney disease (CKD) may be classified according to the National Kidney Foundation Kidney Disease Outcomes Quality Initiative (NKF KDOQI) Guidelines. Once chronic kidney disease is established, i.e., kidney damage or glomerular filtration rate (GFR)<60 mL/min/1.73 m² for ≥3 months, the stage of disease may be assigned according to KDOQI CKD classification. These include Stage 1 (kidney damage with normal or increased GFR): GFR≥90; Stage 2 (kidney damage with mild decreased GFR): GFR 60-89; Stage 3 (Moderate decreased GFR): GFR 30-59; Stage 4 (severe decrease GFR): GFR 15-29; and Stage 5 (kidney failure): GFR<15 (or dialysis). GFR is defined in units of mL/min/1.73 m$^2$.

One embodiment includes a method of treating a renally-impaired subject comprising administering a therapeutically effective amount of Compound 1 or a crystalline form thereof, specifically crystalline form 1'. This method further includes treating a renally-impaired subject with hypertension or heart failure. When used to treat renal disease, Compound 1 or a crystalline form thereof, specifically crystalline form 1' may be administered in combination with other therapeutic agents such as angiotensin-converting enzyme inhibitors, $AT_1$ receptor antagonists, and diuretics.

Another embodiment includes a method of treating a renally-impaired subject having chronic kidney disease with an estimated glomular filtration rate (eGFR) between 60 mL/min/1.73 m$^2$ and 15 mL/min/1.73 m$^2$ comprising administering to a patient a therapeutically effective amount of Compound 1 or a crystalline form thereof, specifically crystalline form 1'. Another embodiment includes a method of treating a renally-impaired subject having chronic kidney disease with an estimated glomular filtration rate (eGFR)≥90 mL/min/1.73 m$^2$ (Stage 1) or an eGFR<15 mL/min/1.73 m$^2$ (Stage 5) comprising administering to a patient a therapeutically effective amount of Compound 1 or a crystalline form thereof, specifically crystalline form 1'. For purposes of this invention, severe kidney disease may be classified as an eGFR<30 mL/min/1.73 m$^2$. In yet another embodiment, a method of treating a renally-impaired subject having chronic kidney disease classified as Stage 1, Stage 2, Stage 3, Stage 4, Stage 5 or eGFR ranges covering one or more of these stages with Compound 1 or a crystalline form thereof, specifically crystalline form 1' is included.

Preventative Therapy

By potentiating the effects of the natriuretic peptides, Compound 1 is also expected to be useful in preventative therapy, due to the antihypertrophic and antifibrotic effects of the natriuretic peptides (see Potter et al. (2009) *Handbook of Experimental Pharmacology* 191:341-366), for example in preventing the progression of cardiac insufficiency after myocardial infarction, preventing arterial restenosis after angioplasty, preventing thickening of blood vessel walls after vascular operations, preventing atherosclerosis, and preventing diabetic angiopathy.

Glaucoma

By potentiating the effects of the natriuretic peptides, Compound 1 is expected to be useful to treat glaucoma. See, for example, Diestelhorst et al. (1989) *International Ophthalmology* 12:99-101. When used to treat glaucoma, Compound 1 may be combined with one or more additional antiglaucoma agents.

Pain Relief

As a NEP inhibitor, Compound 1 is expected to inhibit the degradation of endogenous enkephalins and thus such compounds may also find utility as analgesics. See, for example, Rogues et al. (1980) *Nature* 288:286-288 and Thanawala et al. (2008) *Current Drug Targets* 9:887-894. When used to treat pain, Compound 1 may be combined with one or more additional antinociceptive drugs such as aminopeptidase N or dipeptidyl peptidase III inhibitors, non-steroidal anti-inflammatory agents, monoamine reuptake inhibitors, muscle relaxants, NMDA receptor antagonists, opioid receptor agonists, 5-$HT_{1D}$ serotonin receptor agonists, and tricyclic antidepressants.

Other Utilities

Due to its NEP inhibition properties, Compound 1 is also expected to be useful as an antitussive agent, as well as find utility in the treatment of portal hypertension associated with liver cirrhosis (see Sansoe et al. (2005) *J. Hepatol.* 43:791-798), cancer (see Vesely (2005) *J. Investigative Med.* 53:360-365), depression (see Noble et al. (2007) *Exp. Opin. Ther. Targets* 11:145-159), menstrual disorders, preterm labor, pre-eclampsia, endometriosis, reproductive disorders (for example, male and female infertility, polycystic ovarian syndrome, implantation failure), and male and female sexual dysfunction, including male erectile dysfunction and female sexual arousal disorder. More specifically, Compound 1 is expected to be useful in treating female sexual dysfunction (see Pryde et al. (2006) *J. Med. Chem.* 49:4409-4424), which is often defined as a female patient's difficulty or inability to find satisfaction in sexual expression. This covers a variety of diverse female sexual disorders including, by way of illustration and not limitation, hypoactive sexual desire disorder, sexual arousal disorder, orgasmic disorder and sexual pain disorder. When used to treat such disorders, especially female sexual dysfunction, the compound of the invention may be combined with one or more of the following secondary agents: PDE-V inhibitors, dopamine agonists, estrogen receptor agonists and/or antagonists, androgens, and estrogens. Due to its NEP inhibition property, Compound 1 is also expected to have anti-inflammatory properties, and is expected to have utility as such, particularly when used in combination with statins.

Recent studies suggest that NEP plays a role in regulating nerve function in insulin-deficient diabetes and diet induced obesity. Coppey et al. (2011) *Neuropharmacology* 60:259-266. Therefore, due to its NEP inhibition property, Compound 1 is also expected to be useful in providing protection from nerve impairment caused by diabetes or diet induced obesity.

The amount of Compound 1 administered per dose or the total amount administered per day may be predetermined or it may be determined on an individual patient basis by taking into consideration numerous factors, including the nature and severity of the patient's condition, the condition being treated, the age, weight, and general health of the patient, the tolerance of the patient to the active agent or active metabolite, the route of administration, pharmacological considerations such as the activity, efficacy, pharmacokinetics and toxicology profiles of the compound and any secondary agents being administered, and the like. Treatment of a patient suffering from a disease or medical condition (such as hypertension) can begin with a predetermined dosage or a dosage determined by the treating physician, and will continue for a period of time necessary to prevent, ameliorate, suppress, or alleviate the symptoms of the disease or medical condition. Patients undergoing such treatment will typically be monitored on a routine basis to determine the effectiveness of therapy. For example, in treating hypertension, blood pressure measurements may be used to determine the effectiveness of treatment. Similar indicators for other diseases and conditions described herein, are well known and are readily available to the treating physician. Continuous monitoring by the physician will insure that the optimal amount of Compound 1 will be administered at any given time, as well as facilitating the determination of the duration of treatment. This is of particular value when secondary agents are also being administered, as their selection, dosage, and duration of therapy may also require adjustment. In this way, the treatment regimen and dosing schedule can be adjusted over the course of therapy so that the lowest amount of active agent or active metabolite that exhibits the desired effectiveness is administered and, further, that administration is continued only so long as is necessary to successfully treat the disease or medical condition.

Compound 1 also finds utility as an intermediate useful for the preparation of crystalline forms of Compound 1, including, for example, crystalline form 1'.

Research Tools

Since Compound 1 possesses NEP enzyme inhibition activity, it is also useful as a research tool for investigating or studying biological systems or samples having a NEP enzyme, for example to study diseases where the NEP enzyme or its peptide substrates plays a role. Any suitable biological system or sample having a NEP enzyme may be employed in such studies which may be conducted either in vitro or in vivo. Representative biological systems or samples suitable for such studies include, but are not limited to, cells, cellular extracts, plasma membranes, tissue samples, isolated organs, mammals (such as mice, rats, guinea pigs, rabbits, dogs, pigs, humans, and so forth), and the like, with mammals being of particular interest. In one particular embodiment of the invention, NEP enzyme activity in a mammal is inhibited by administering a NEP-inhibiting amount of Compound 1.

When used as a research tool, a biological system or sample comprising a NEP enzyme is typically contacted with a NEP enzyme-inhibiting amount of Compound 1. After the biological system or sample is exposed to the compound, the effects of inhibiting the NEP enzyme are determined using conventional procedures and equipment, such as by measuring receptor binding in a binding assay or measuring ligand-mediated changes in a functional assay. Exposure encompasses contacting cells or tissue with the compound, administering the compound to a mammal, for example by i.p., p. o, i. v., s.c., or inhaled administration, and so forth. This determining step can involve measuring a response (a quantitative analysis) or can involve making an observation (a qualitative analysis). Measuring a response involves, for example, determining the effects of the compound on the biological system or sample using conventional procedures and equipment, such as enzyme activity assays and measuring enzyme substrate or product mediated changes in functional assays. The assay results can be used to determine the activity level as well as the amount of compound necessary to achieve the desired result, that is, a NEP enzyme-inhibiting amount. Typically, the determining step will involve determining the effects of inhibiting the NEP enzyme.

Additionally, Compound 1 can be used as a research tool for evaluating other chemical compounds, and thus is also useful in screening assays to discover, for example, new compounds having NEP-inhibiting activity. In this manner, Compound 1 is used as a standard in an assay to allow comparison of the results obtained with a test compound and with Compound 1 to identify those test compounds that have about equal or superior activity, if any. For example, $pK_i$ data for a test compound or a group of test compounds is compared to the $pK_i$ data for Compound 1 to identify those test compounds that have the desired properties, for example, test compounds having a $pK_i$ value equal or superior to the compound of the invention. This aspect of the invention includes, as separate embodiments, both the generation of comparison data (using the appropriate assays) and the analysis of test data to identify test compounds of interest. Thus, a test compound can be evaluated in a biological assay, by a method comprising the steps of: (a) conducting a biological assay with a test compound to provide a first assay value; (b) conducting the biological assay with Compound 1 to provide a second assay value; wherein step (a) is conducted either before, after or concurrently with step (b); and (c) comparing the first assay value from step (a) with the second assay value from step (b). Exemplary biological assays include a NEP enzyme inhibition assay.

Still another aspect of the invention relates to a method of studying a biological system or sample comprising a NEP enzyme, the method comprising: (a) contacting the biological system or sample with Compound 1; and (b) determining the effects caused by the compound on the biological system or sample.

Pharmaceutical Compositions and Formulations

Compound 1 is typically administered to a patient in the form of a pharmaceutical composition or formulation. Such pharmaceutical compositions may be administered to the patient by any acceptable route of administration including, but not limited to, oral, rectal, vaginal, nasal, inhaled, topical (including transdermal), ocular, and parenteral modes of administration. Further, Compound 1 may be administered, for example orally, in multiple doses per day (for example, two, three, or four times daily), in a single daily dose or a single weekly dose. It will be understood that any form of Compound 1, (that is, free base, free acid, pharmaceutically acceptable salt, solvate, etc.) that is suitable for the particular mode of administration can be used in the pharmaceutical compositions discussed herein.

Accordingly, in one embodiment, the invention relates to a pharmaceutical composition comprising a pharmaceutically acceptable carrier and Compound 1. The composition may contain other therapeutic and/or formulating agents if desired. When discussing compositions, the "Compound 1" may also be referred to herein as the "active agent," to distinguish it from other components of the formulation, such as the carrier. Thus, it is understood that the term "active agent" includes the compounds of the invention as well as its pharmaceutically acceptable salts.

The pharmaceutical compositions of the invention typically contain a therapeutically effective amount of Compound 1. Those skilled in the art will recognize, however, that a pharmaceutical composition may contain more than a therapeutically effective amount, such as in bulk compositions, or less than a therapeutically effective amount, that is, individual unit doses designed for multiple administration to achieve a therapeutically effective amount. Typically, the composition will contain from about 0.01-95 wt % of active agent, including, from about 0.01-30 wt %, such as from about 0.01-10 wt %, with the actual amount depending upon the formulation itself, the route of administration, the frequency of dosing, and so forth. In one embodiment, a composition suitable for an oral dosage form, for example, may contain about 5-70 wt %, or from about 10-60 wt % of active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable composition for a particular mode of administration is well within the scope of those skilled in the pharmaceutical arts. Additionally, carriers or excipients used in such compositions are commercially available. By way of further illustration, conventional formulation techniques are described in Remington: The Science and Practice of Pharmacy, 20th Edition, Lippincott Williams & White, Baltimore, Md. (2000); and H. C. Ansel et al., Pharmaceutical Dosage Forms and Drug Delivery Systems, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; fatty acid salts, such as magnesium stearate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; compressed propellant gases, such as chlorofluorocarbons and hydrofluorocarbons; and other non-toxic compatible substances employed in pharmaceutical compositions.

In one embodiment of the invention, the pharmaceutically acceptable carrier is magnesium stearate. For example, the pharmaceutical composition may comprise Compound 1 or a crystalline form 1' and magnesium stearate in a ratio of about 3:1 to about 10:1 of Compound 1 or a crystalline form 1' to magnesium stearate. Other ratios of Compound 1 or a crystalline form 1' to magnesium stearate include, but are not limited to, 1:1, 5:1, 15:1, 20:1, 25:1, 30:1 and 50:1.

Pharmaceutical compositions are typically prepared by thoroughly and intimately mixing or blending the active agent with a pharmaceutically acceptable carrier and one or more optional ingredients. The resulting uniformly blended mixture may then be shaped or loaded into tablets, capsules, pills, canisters, cartridges, dispensers and the like using conventional procedures and equipment.

In one embodiment, the pharmaceutical compositions are suitable for oral administration. Suitable compositions for oral administration may be in the form of capsules, tablets, pills, lozenges, cachets, dragees, powders, granules; solutions or suspensions in an aqueous or non-aqueous liquid; oil-in-water or water-in-oil liquid emulsions; elixirs or syrups; and the like; each containing a predetermined amount of the active agent.

When intended for oral administration in a solid dosage form (capsules, tablets, pills and the like), the composition will typically comprise the active agent and one or more pharmaceutically acceptable carriers, such as sodium citrate, dicalcium phosphate, or magnesium stearate. Solid dosage forms may also comprise fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents. For the purpose of this invention, the terms "pharmaceutically acceptable carriers" are inclusive of all the terms such as carriers, fillers or extenders, binders, humectants, solution retarding agents, wetting agents, absorbents, lubricants, coloring agents and buffering agents described above.

Release agents, wetting agents, coating agents, sweetening, flavoring and perfuming agents, preservatives and antioxidants may also be present in the pharmaceutical compositions. Exemplary coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methyl cellulose acetate succinate, and the like. Examples of pharmaceutically acceptable antioxidants include: water-soluble antioxidants, such as ascorbic acid, cysteine hydrochloride, sodium bisulfate, sodium metabisulfate sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like.

Compositions may also be formulated to provide slow or controlled release of the active agent using, by way of example, hydroxypropyl methyl cellulose in varying proportions or other polymer matrices, liposomes and/or microspheres. In addition, the pharmaceutical compositions of the invention may contain opacifying agents and may be formulated so that they release the active agent only, or preferentially, in a certain portion of the gastrointestinal tract, optionally, in a delayed manner. Examples of embedding compositions which can be used include polymeric substances and waxes. The active agent can also be in micro-encapsulated form, optionally with one or more of the above-described excipients.

One embodiment of the invention includes an oral dosage form comprising Compound 1 or crystalline form 1' in a capsule, tablet, liquid or suspension. Another embodiment of the invention relates to an oral dosage form where a release of the Compound 1 or crystalline form 1' in a subject is an immediate, controlled or delayed release. If a capsule is used as an oral dosage form, another embodiment includes the capsule being comprised of gelatin, polysaccharides or synthetic polymers. In a particular embodiment, the capsule comprises hydroxypropyl methylcelluose.

Suitable capsule materials according to the invention are selected from gelatin, cellulose derivatives, starch, starch derivatives, chitosan and synthetic plastics. If gelatin is used as the capsule material, it may be used in admixture with other additives selected from polyethyleneglycol (PEG), glycerol, sorbitol, polypropyleneglycol, PEO-PPO block copolymers and other polyalcohols and polyethers. When a cellulose derivative is used as the capsule material, hydroxypropylmethylcellulose, hydroxypropylcellulose, methylcellulose, hydroxymethylcellulose and hydroxyethylcellulose are preferred polymers. If synthetic plastics are used as a capsule material, polyethylene, polycarbonate, polyester, polypropylene and polyethylene terephthalate are preferred materials. Particularly preferred are polyethylene, polycarbonate or polyethylene terephthalate.

Suitable liquid dosage forms for oral administration include, by way of illustration, pharmaceutically acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (for example, cottonseed, groundnut, corn, germ, olive, castor and sesame oils), glycerol, tetrahydrofuryl alcohol, polyethylene glycols and fatty acid esters of sorbitan, and mixtures thereof. Suspensions may contain suspending agents such as, for example, ethoxylated isostearyl alcohols, polyoxyethylene sorbitol and sorbitan esters, microcrystalline cellulose, aluminium metahydroxide, bentonite, agar-agar and tragacanth, and mixtures thereof.

When intended for oral administration, the pharmaceutical compositions of the invention may be packaged in a unit dosage form. The term "unit dosage form" refers to a physically discrete unit suitable for dosing a patient, that is, each unit containing a predetermined quantity of the active agent calculated to produce the desired therapeutic effect either alone or in combination with one or more additional units. For example, such unit dosage forms may be capsules, tablets, pills, and the like.

In another embodiment, the compositions of the invention are suitable for inhaled administration, and will typically be in the form of an aerosol or a powder. Such compositions are generally administered using well-known delivery devices, such as a nebulizer, dry powder, or metered-dose inhaler. Nebulizer devices produce a stream of high velocity air that causes the composition to spray as a mist that is carried into a patient's respiratory tract. An exemplary nebulizer formulation comprises the active agent dissolved in a carrier to form a solution, or micronized and combined with a carrier to form a suspension of micronized particles of respirable size. Dry powder inhalers administer the active agent as a free-flowing powder that is dispersed in a patient's airstream during inspiration. An exemplary dry powder formulation comprises the active agent dry-blended with an excipient such as lactose, starch, mannitol, dextrose, polylactic acid, polylactide-co-glycolide, and combinations thereof. Metered-dose inhalers discharge a measured amount of the active agent using compressed propellant gas. An exemplary metered-dose formulation comprises a solution or suspension of the active agent in a liquefied propellant, such as a chlorofluorocarbon or hydrofluoroalkane. Optional components of such formulations include co-solvents, such as ethanol or pentane, and surfactants, such as sorbitan trioleate, oleic acid, lecithin, glycerin, and sodium lauryl sulfate. Such compositions are typically prepared by adding chilled or pressurized hydrofluoroalkane to a suitable container containing the active agent, ethanol (if present) and the surfactant (if present). To prepare a suspension, the active agent is micronized and then combined with the propellant. Alternatively, a suspension formulation can be prepared by spray drying a coating of surfactant on micronized particles of the active agent. The formulation is then loaded into an aerosol canister, which forms a portion of the inhaler.

Compound 1 and compositions thereof can also be administered parenterally, for example, by subcutaneous, intravenous, intramuscular, or intraperitoneal injection. For such administration, the active agent is provided in a sterile solution, suspension, or emulsion. Exemplary solvents for preparing such formulations include water, saline, electrolytes, low molecular weight alcohols such as propylene glycol and polyethylene glycol, oils, amino acids, gelatin, sugars, fatty acid esters such as ethyl oleate, and the like. Parenteral formulations may also contain one or more antioxidants, solubilizers, stabilizers, preservatives, wetting agents, emulsifiers, and dispersing agents. Surfactants, additional stabilizing agents or pH-adjusting agents (acids, bases or buffers) and anti-oxidants are particularly useful to provide stability to the formulation, for example, to minimize or avoid hydrolysis of ester and amide linkages that may be present in the compound. These formulations may be rendered sterile by use of a sterile injectable medium, a sterilizing agent, filtration, irradiation, or heat.

Representative physiologically-acceptable aqueous carriers include, by way of example, Sterile Water for Injection, USP; Dextrose Injection, USP (e.g., 2.5, 5.0, 10, 20% dextrose, including 5% Dextrose Injection (D5/W)); Dextrose and Sodium Chloride Injection, USP (e.g., dextrose varying from 2.5 to 10% and sodium chloride varying from 0.12 (19 mEq sodium) to 0.9% (154 mEq sodium)); Mannitol Injection, USP, (e.g., 5, 10, 15, 20 and 25% mannitol); Ringer's Injection, USP (e.g., 147 mEq sodium, 4 mEq potassium, 4.5 mEq calcium and 156 mEq chloride per liter); Lactated Ringer's Injection, USP (e.g., 2.7 mEq calcium, 4 mEq potassium, 130 mEq sodium, and 28 mEq lactate per liter); Sodium Chloride Injection, USP (e.g., 0.9% sodium chloride) and the like.

When administered to a patient, the Compound 1 will typically be diluted in about 0.5 mL to about 10 mL of the aqueous carrier per mg of the Compound 1, such as about 0.6 to about 8 mL per mg.

In one particular embodiment, the parenteral formulation comprises an aqueous cyclodextrin solution as the pharmaceutically acceptable carrier. Suitable cyclodextrins include cyclic molecules containing six or more α-D-glucopyranose units linked at the 1,4 positions by a linkages as in amylase, β-cyclodextrin or cycloheptaamylose. Exemplary cyclodextrins include cyclodextrin derivatives such as hydroxypropyl and sulfobutyl ether cyclodextrins such as hydroxypropyl-β-cyclodextrin and sulfobutyl ether β-cyclodextrin. Exemplary buffers for such formulations include carboxylic acid-based buffers such as citrate, lactate and maleate buffer solutions. In one embodiment of the invention, an intravenous dosage form comprises Compound 1 or crystalline form V in a buffered solution.

In one embodiment, Compound 1 or a pharmaceutical composition thereof is a lyophilized powder. Typically, the lyophilized powder is sterile and is packaged in a hermetically-sealed vial or ampoule or similar container.

Compound 1 can also be administered transdermally using known transdermal delivery systems and excipients. For example, Compound 1 can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

Secondary Agents

Compound 1 may be useful as the sole treatment of a disease or may be combined with one or more additional therapeutic agents in order to obtain the desired therapeutic effect. Thus, in one embodiment, pharmaceutical compositions of the invention contain other drugs that are co-administered with Compound 1. For example, the composition may further comprise one or more drugs (also referred to as "secondary agents(s)"). Such therapeutic agents are well known in the art, and include adenosine receptor antagonists, α-adrenergic receptor antagonists, $\beta_1$-adrenergic receptor antagonists, $\beta_2$-adrenergic receptor agonists, dual-acting β-adrenergic receptor antagonist/$\alpha_1$-receptor antagonists, advanced glycation end product breakers, aldosterone antagonists, aldosterone synthase inhibitors, aminopeptidase N inhibitors, androgens, angiotensin-converting enzyme inhibitors and dual-acting angiotensin-converting enzyme/neprilysin inhibitors, angiotensin-converting enzyme 2 activators and stimulators, angiotensin-II vaccines, anticoagulants, anti-diabetic agents, antidiarrheal agents, anti-glaucoma agents, anti-lipid agents, antinociceptive agents, anti-thrombotic agents, $AT_1$ receptor antagonists and dual-acting $AT_1$ receptor antagonist/neprilysin inhibitors and multifunctional angiotensin receptor blockers, bradykinin receptor antagonists, calcium channel blockers, chymase inhibitors, digoxin, diuretics, dopamine agonists, endothelin converting enzyme inhibitors, endothelin receptor antagonists, HMG-CoA reductase inhibitors, estrogens, estrogen receptor agonists and/or antagonists, monoamine reuptake inhibitors, muscle relaxants, natriuretic peptides and their analogs, natriuretic peptide clearance receptor antagonists, neprilysin inhibitors, nitric oxide donors, non-steroidal anti-inflammatory agents, N-methyl d-aspartate receptor antagonists, opioid receptor agonists, phosphodiesterase inhibitors, prostaglandin analogs, prostaglandin receptor agonists, renin inhibitors, selective serotonin reuptake inhibitors, sodium channel blocker, soluble guanylate cyclase stimulators and activators, tricyclic antidepressants, vasopressin receptor antagonists, and combinations thereof. Specific examples of these agents are detailed herein.

A specific embodiment includes a pharmaceutical composition comprising Compound 1 or crystalline form thereof and an $AT_1$ receptor antagonist, an angiotensin-converting enzyme inhibitor, a phosphodiesterase (PDE) inhibitor, a renin inhibitor, a diuretic, or combinations thereof, and optionally one or more pharmaceutically acceptable carriers.

Accordingly, in yet another aspect of the invention, a pharmaceutical composition comprises Compound 1, a second active agent, and a pharmaceutically acceptable carrier. Third, fourth etc. active agents may also be included in the composition. In combination therapy, the amount of compound 1 that is administered, as well as the amount of secondary agents, may be less than the amount typically administered in monotherapy.

Compound 1 may be physically mixed with the second active agent to form a composition containing both agents; or each agent may be present in separate and distinct compositions which are administered to the patient simultaneously or at separate times. For example, Compound 1 can be combined with a second active agent using conventional procedures and equipment to form a combination of active agents comprising Compound 1 and a second active agent. Additionally, the active agents may be combined with a pharmaceutically acceptable carrier to form a pharmaceutical composition comprising Compound 1, a second active agent and a pharmaceutically acceptable carrier. In this embodiment, the components of the composition are typically mixed or blended to create a physical mixture. The physical mixture is then administered in a therapeutically effective amount using any of the routes described herein.

Alternatively, the active agents may remain separate and distinct before administration to the patient. In this embodiment, the agents are not physically mixed together before administration but are administered simultaneously or at separate times as separate compositions. Such compositions can be packaged separately or may be packaged together in a kit. When administered at separate times, the secondary agent will typically be administered less than 24 hours after administration of Compound 1, ranging anywhere from concurrent with administration of the compound of the invention to about 24 hours post-dose. This is also referred to as sequential administration. Thus, Compound 1 can be orally administered simultaneously or sequentially with another active agent using two tablets, with one tablet for each active agent, where sequential may mean being administered immediately after administration of Compound 1 or at some predetermined time later (for example, one hour later or three hours later). It is also contemplated that the secondary agent may be administered more than 24 hours after administration of Compound 1. Alternatively, the combination may be administered by different routes of administration, that is, one orally and the other by inhalation.

In one embodiment, the kit comprises a first dosage form comprising Compound 1 and at least one additional dosage form comprising one or more of the secondary agents set forth herein, in quantities sufficient to carry out the methods of the invention. The first dosage form and the second (or third, etc.) dosage form together comprise a therapeutically effective amount of active agents for the treatment or prevention of a disease or medical condition in a patient.

Secondary agent(s), when included, are present in a therapeutically effective amount such that they are typically administered in an amount that produces a therapeutically beneficial effect when co-administered with Compound 1 of the invention. The secondary agent can be in the form of a pharmaceutically acceptable salt, solvate, optically pure stereoisomer, and so forth. The secondary agent may also be in the form of a prodrug, for example, a compound having a carboxylic acid group that has been esterified. Thus, secondary agents listed herein are intended to include all such forms, and are commercially available or can be prepared using conventional procedures and reagents.

In one embodiment, Compound 1 is administered in combination with an adenosine receptor antagonist, examples of which include naxifylline, rolofylline, SLV-320, theophylline, and tonapofylline.

In one embodiment, Compound 1 is administered in combination with an α-adrenergic receptor antagonist, examples of which include doxazosin, prazosin, tamsulosin, and terazosin.

Compound 1 may also be administered in combination with a $\beta_1$-adrenergic receptor antagonist ("$\beta_1$-blocker"), examples of which include acebutolol, alprenolol, amosulalol, arotinolol, atenolol, befunolol, betaxolol, bevantolol, bisoprolol, bopindolol, bucindolol, bucumolol, bufetolol, bufuralol, bunitrolol, bupranolol, bubridine, butofilolol, carazolol, carteolol, carvedilol, celiprolol, cetamolol, cloranolol, dilevalol, epanolol, esmolol, indenolol, labetolol, levobunolol, mepindolol, metipranolol, metoprolol such as metoprolol succinate and metoprolol tartrate, moprolol, nadolol, nadoxolol, nebivalol, nipradilol, oxprenolol, penbutolol, perbutolol, pindolol, practolol, pronethalol, propranolol, sotalol, sufinalol, talindol, tertatolol, tilisolol, timolol, toliprolol, xibenolol, and combinations thereof. In one particular embodiment, the $\beta_1$-antagonist is selected from atenolol, bisoprolol, metoprolol, propranolol, sotalol, and combinations thereof. Typically, the β$_1$-blocker will be administered in an amount sufficient to provide from about 2-900 mg per dose.

In one embodiment, Compound 1 is administered in combination with a β$_2$-adrenergic receptor agonist, examples of which include albuterol, bitolterol, fenoterol, formoterol, indacaterol, isoetharine, levalbuterol, metaproterenol, pirbuterol, salbutamol, salmefamol, salmeterol, terbutaline, vilanterol, and the like. Typically, the β$_2$-adrenergic receptor agonist will be administered in an amount sufficient to provide from about 0.05-500 μg per dose.

In one embodiment, Compound 1 is administered in combination with an advanced glycation end product (AGE) breaker, examples of which include alagebrium (or ALT-711) and TRC4149.

In another embodiment, Compound 1 is administered in combination with an aldosterone antagonist, examples of which include eplerenone, spironolactone, and combinations thereof. Typically, the aldosterone antagonist will be administered in an amount sufficient to provide from about 5-300 mg per day.

In one embodiment, Compound 1 is administered in combination with an aminopeptidase N or dipeptidyl peptidase III inhibitor, examples of which include bestatin and PC18 (2-amino-4-methylsulfonyl butane thiol, methionine thiol).

Compound 1 can also be administered in combination with an angiotensin-converting enzyme (ACE) inhibitor, examples of which include accupril, alacepril, benazepril, benazeprilat, captopril, ceranapril, cilazapril, delapril, enalapril, enalaprilat, fosinopril, fosinoprilat, imidapril, lisinopril, moexipril, monopril, moveltipril, pentopril, perindopril, quinapril, quinaprilat, ramipril, ramiprilat, saralasin acetate, spirapril, temocapril, trandolapril, zofenopril, and combinations thereof. In a particular embodiment, the ACE inhibitor is selected from: benazepril, captopril, enalapril, lisinopril, ramipril, and combinations thereof. Typically, the ACE inhibitor will be administered in an amount sufficient to provide from about 1-150 mg per day.

In another embodiment, Compound 1 is administered in combination with a dual-acting angiotensin-converting enzyme/neprilysin (ACE/NEP) inhibitor, examples of which include: AVE-0848 ((4S,7S,12bR)-7-[3-methyl-2(S)-sulfanylbutyramido]-6-oxo-1,2,3,4,6,7,8,12b-octahydropyrido[2,1-a][2]-benzazepine-4-carboxylic acid); AVE-7688 (ilepatril) and its parent compound; BMS-182657 (2-[2-oxo-3(S)-[3-phenyl-2(S)-sulfanylpropionamido]-2,3,4,5-tetrahydro-1H-1-benzazepin-1-yl]acetic acid); CGS-35601 (N-[1-[4-methyl-2 (S)-sulfanylpentanamido]cyclopentylcarbonyl]-L-tryptophan); fasidotril; fasidotrilate; enalaprilat; ER-32935 ((3R,6S,9aR)-6-[3(S)-methyl-2(S)-sulfanylpentanamido]-5-oxoperhydrothiazolo[3,2-a]azepine-3-carboxylic acid); gempatrilat; MDL-101264 ((4S,7S,12bR)-7-[2(S)-(2-morpholinoacetylthio)-3-phenylpropionamido]-6-oxo-1,2,3,4,6,7,8,12b-octahydropyrido[2,1-a][2] benzazepine-4-carboxylic acid); MDL-101287 ([4S-[4α,7α(R*),12β]]-7-[2-(carboxymethyl)-3-phenylpropionamido]-6-oxo-1,2,3,4,6,7,8,12b-octahydropyrido[2,1-a][2] benzazepine-4-carboxylic acid); omapatrilat; RB-105 (N-[2 (S)-(mercaptomethyl)-3-(R)-phenylbutyl]-L-alanine); sampatrilat; SA-898 ((2R,4R)—N-[2-(2-hydroxyphenyl)-3-(3-mercaptopropionyOthiazolidin-4-ylcarbonyl]-L-phenylalanine); Sch-50690 (N-[1(S)-carboxy-2-[N2-(methanesulfonyl)-L-lysylamino]ethyl]-L-valyl-L-tyrosine); and combinations thereof, may also be included. In one particular embodiment, the ACE/NEP inhibitor is selected from: AVE-7688, enalaprilat, fasidotril, fasidotrilate, omapatrilat, sampatrilat, and combinations thereof.

In one embodiment, Compound 1 is administered in combination with an angiotensin-converting enzyme 2 (ACE2) activator or stimulator.

In one embodiment, Compound 1 is administered in combination with an angiotensin-II vaccine, examples of which include ATR12181 and CYT006-AngQb.

In one embodiment, Compound 1 is administered in combination with an anticoagulant, examples of which include: coumarins such as warfarin; heparin; and direct thrombin inhibitors such as argatroban, bivalirudin, dabigatran, and lepirudin.

In yet another embodiment, Compound 1 is administered in combination with an anti-diabetic agent, examples of which include injectable drugs as well as orally effective drugs, and combinations thereof. Examples of injectable drugs include insulin and insulin derivatives. Examples of orally effective drugs include: biguanides such as metformin;
glucagon antagonists; α-glucosidase inhibitors such as acarbose and miglitol; dipeptidyl peptidase IV inhibitors (DPP-IV inhibitors) such as alogliptin, denagliptin, linagliptin, saxagliptin, sitagliptin, and vildagliptin; meglitinides such as repaglinide; oxadiazolidinediones; sulfonylureas such as chlorpropamide, glimepiride, glipizide, glyburide, and tolazamide; thiazolidinediones such as pioglitazone and rosiglitazone; and combinations thereof.

In another embodiment, Compound 1 is administered in combination with antidiarrheal treatments. Representative treatment options include oral rehydration solutions (ORS), loperamide, diphenoxylate, and bismuth subsalicylate.

In yet another embodiment, Compound 1 is administered in combination with an anti-glaucoma agent, examples of which include: α-adrenergic agonists such as brimonidine; β$_1$-adrenergic receptor antagonists; topical β$_1$-blockers such as betaxolol, levobunolol, and timolol; carbonic anhydrase inhibitors such as acetazolamide, brinzolamide, or dorzolamide; cholinergic agonists such as cevimeline and DMXB-anabaseine; epinephrine compounds; miotics such as pilocarpine; and prostaglandin analogs.

In yet another embodiment, Compound 1 is administered in combination with an anti-lipid agent, examples of which include: cholesteryl ester transfer protein inhibitors (CETPs) such as anacetrapib, dalcetrapib, and torcetrapib; statins such as atorvastatin, fluvastatin, lovastatin, pravastatin, rosuvastatin and simvastatin; and combinations thereof.

In one embodiment, Compound 1 is administered in combination with an anti-thrombotic agent, examples of which include: aspirin; anti-platelet agents such as clopidogrel, prasugrel, and ticlopidine; heparin; and combinations thereof.

In one embodiment, Compound 1 is administered in combination with an AT$_1$ receptor antagonist, also known as angiotensin II type 1 receptor blockers (ARBs). Representative ARBs include abitesartan, azilsartan (e.g., azilsartan medoxomil), benzyllosartan, candesartan, candesartan cilexetil, elisartan, embusartan, enoltasosartan, eprosartan, EXP3174, fonsartan, forasartan, glycyllosartan, irbesartan, isoteoline, losartan, medoxomil, milfasartan, olmesartan (e.g., olmesartan medoxomil), opomisartan, pratosartan, ripisartan, saprisartan, saralasin, sarmesin, TAK-591, tasosartan, telmisartan, valsartan, zolasartan, and combinations thereof. In a particular embodiment, the ARB is selected from azilsartan medoxomil, candesartan cilexetil, eprosartan, irbesartan, losartan, olmesartan medoxomil, saprisartan, tasosartan, telmisartan, valsartan, and combinations thereof.

Exemplary salts and/or prodrugs include candesartan cilexetil, eprosartan mesylate, losartan potassium salt, and olmesartan medoxomil. Typically, the ARB will be administered in an amount sufficient to provide from about 4-600 mg per dose, with exemplary daily dosages ranging from 20-320 mg per day.

Compound 1 may also be administered in combination with a dual-acting agent, such as an $AT_1$ receptor antagonist/neprilysin inhibitor (ARB/NEP) inhibitor, examples of which include compounds described in U.S. Pat. Nos. 7,879,896 and 8,013,005, both to Allegretti et al., such as the compound, 4'-{2-ethoxy-4-ethyl-5-[((S)-2-mercapto-4-methylpentanoylamino)-methyl]imidazol-1-ylmethyl}-3'-fluorobiphenyl-2-carboxylic acid.

Compound 1 may also be administered in combination with multifunctional angiotensin receptor blockers as described in Kurtz & Klein (2009) *Hypertension Research* 32:826-834.

In one embodiment, Compound 1 is administered in combination with a bradykinin receptor antagonist, for example, icatibant (HOE-140). It is expected that this combination therapy may present the advantage of preventing angioedema or other unwanted consequences of elevated bradykinin levels.

In one embodiment, Compound 1 is administered in combination with a calcium channel blocker, examples of which include amlodipine, anipamil, aranipine, barnidipine, bencyclane, benidipine, bepridil, clentiazem, cilnidipine, cinnarizine, diltiazem, efonidipine, elgodipine, etafenone, felodipine, fendiline, flunarizine, gallopamil, isradipine, lacidipine, lercanidipine, lidoflazine, lomerizine, manidipine, mibefradil, nicardipine, nifedipine, niguldipine, niludipine, nilvadipine, nimodipine, nisoldipine, nitrendipine, nivaldipine, perhexiline, prenylamine, ryosidine, semotiadil, terodiline, tiapamil, verapamil, and combinations thereof. In a particular embodiment, the calcium channel blocker is selected from amlodipine, bepridil, diltiazem, felodipine, isradipine, lacidipine, nicardipine, nifedipine, niguldipine, niludipine, nimodipine, nisoldipine, ryosidine, verapamil, and combinations thereof. Typically, the calcium channel blocker will be administered in an amount sufficient to provide from about 2-500 mg per dose.

In one embodiment, Compound 1 is administered in combination with a chymase inhibitor, such as TPC-806 and 2-(5-formylamino-6-oxo-2-phenyl-1,6-dihydropyrimidine-1-yl)-N-[{3,4-dioxo-1-phenyl-7-(2-pyridyloxy)}-2-heptyl]acetamide (NK3201).

In one embodiment, Compound 1 is administered in combination with a diuretic, examples of which include: carbonic anhydrase inhibitors such as acetazolamide and dichlorphenamide; loop diuretics, which include sulfonamide derivatives such as acetazolamide, ambuside, azosemide, bumetanide, butazolamide, chloraminophenamide, clofenamide, clopamide, clorexolone, disulfamide, ethoxzolamide, furosemide, mefruside, methazolamide, piretanide, torsemide, tripamide, and xipamide, as well as non-sulfonamide diuretics such as ethacrynic acid and other phenoxyacetic acid compounds such as tienilic acid, indacrinone and quincarbate; osmotic diuretics such as mannitol; potassium-sparing diuretics, which include aldosterone antagonists such as spironolactone, and $Na^+$ channel inhibitors such as amiloride and triamterene; thiazide and thiazide-like diuretics such as althiazide, bendroflumethiazide, benzylhydrochlorothiazide, benzthiazide, buthiazide, chlorthalidone, chlorothiazide, cyclopenthiazide, cyclothiazide, epithiazide, ethiazide, fenquizone, flumethiazide, hydrochlorothiazide, hydroflumethiazide, indapamide, methylclothiazide, meticrane, metolazone, paraflutizide, polythiazide, quinethazone, teclothiazide, and trichloromethiazide; and combinations thereof. In a particular embodiment, the diuretic is selected from amiloride, bumetanide, chlorothiazide, chlorthalidone, dichlorphenamide, ethacrynic acid, furosemide, hydrochlorothiazide, hydroflumethiazide, indapamide, methylclothiazide, metolazone, torsemide, triamterene, and combinations thereof. The diuretic will be administered in an amount sufficient to provide from about 5-50 mg per day, more typically 6-25 mg per day, with common dosages being 6.25 mg, 12.5 mg or 25 mg per day.

Compound 1 may also be administered in combination with an endothelin converting enzyme (ECE) inhibitor, examples of which include phosphoramidon, CGS 26303, and combinations thereof.

In a particular embodiment, Compound 1 is administered in combination with an endothelin receptor antagonist, examples of which include: selective endothelin receptor antagonists that affect endothelin A receptors, such as avosentan, ambrisentan, atrasentan, BQ-123, clazosentan, darusentan, sitaxentan, and zibotentan; and dual endothelin receptor antagonists that affect both endothelin A and B receptors, such as bosentan, macitentan, and tezosentan.

In yet another embodiment, Compound 1 is administered in combination with one or more HMG-CoA reductase inhibitors, which are also known as statins. Representative statins include atorvastatin, fluvastatin, lovastatin, pitavastatin, pravastatin, rosuvastatin and simvastatin.

In one embodiment, Compound 1 is administered in combination with a monoamine reuptake inhibitor, examples of which include norepinephrine reuptake inhibitors such as atomoxetine, buproprion and the buproprion metabolite hydroxybuproprion, maprotiline, reboxetine, and viloxazine; selective serotonin reuptake inhibitors (SSRIs) such as citalopram and the citalopram metabolite desmethylcitalopram, dapoxetine, escitalopram (e.g., escitalopram oxalate), fluoxetine and the fluoxetine desmethyl metabolite norfluoxetine, fluvoxamine (e.g., fluvoxamine maleate), paroxetine, sertraline and the sertraline metabolite demethylsertraline; dual serotonin-norepinephrine reuptake inhibitors (SNRIs) such as bicifadine, duloxetine, milnacipran, nefazodone, and venlafaxine; and combinations thereof.

In another embodiment, Compound 1 is administered in combination with a muscle relaxant, examples of which include: carisoprodol, chlorzoxazone, cyclobenzaprine, diflunisal, metaxalone, methocarbamol, and combinations thereof.

In one embodiment, Compound 1 is administered in combination with a natriuretic peptide or analog, examples of which include: carperitide, CD-NP (Nile Therapeutics), CU-NP, nesiritide, PL-3994 (Palatin Technologies, Inc.), ularitide, cenderitide, and compounds described in Ogawa et al (2004) *J. Biol. Chem.* 279:28625-31. These compounds are also referred to as natriuretic peptide receptor-A (NPR-A) agonists. In another embodiment, Compound 1 is administered in combination with a natriuretic peptide clearance receptor (NPR-C) antagonist such as SC-46542, cANF (4-23), and AP-811 (Veale (2000) *Bioorg Med Chem Lett* 10:1949-52). For example, AP-811 has shown synergy when combined with the NEP inhibitor, thiorphan (Wegner (1995) *Clin. Exper. Hypert.* 17:861-876).

In another embodiment, Compound 1 is administered in combination with a neprilysin (NEP) inhibitor, examples of which include: AHU-377; candoxatril; candoxatrilat; dexecadotril ((+)-N-[2(R)-(acetylthiomethyl)-3-phenylpropionyl]glycine benzyl ester); CGS-24128 (3-[3-(biphenyl-4- yl)-2-(phosphonomethylamino)propionamido]propionic acid); CGS-24592 ((S)-3-[3-(biphenyl-4-yl)-2-(phosphonomethylamino)propionamido]propionic acid); CGS-25155 (N-[9(R)-(acetylthiomethyl)-10-oxo-1-azacyclodecan-2(S)-ylcarbonyl]-4(R)-hydroxy-L-proline benzyl ester); 3-(1-carbamoylcyclohexyl)propionic acid derivatives described in WO 2006/027680 to Hepworth et al. (Pfizer Inc.); JMV-390-1 (2(R)-benzyl-3-(N-hydroxycarbamoyl)propionyl-L-isoleucyl-L-leucine); ecadotril; phosphoramidon; retrothiorphan; RU-42827 (2-(mercaptomethyl)-N-(4-pyridinyl)benzenepropionamide); RU-44004 (N-(4-morpholinyl)-3-phenyl-2-(sulfanylmethyl)propionamide); SCH-32615 ((S)—N—[N-(1-carboxy-2-phenylethyl)-L-phenylalanyl]-β-alanine) and its prodrug SCH-34826 ((S)—N—[N-[1-[[(2,2-dimethyl-1,3-dioxolan-4-yl)methoxy]carbonyl]-2-phenylethyl]-L-phenylalanyl]-β-alanine); sialorphin; SCH-42495 (N-[2(S)-(acetylsulfanylmethyl)-3-(2-methylphenyl)propionyl]-L-methionine ethyl ester); spinorphin; SQ-28132 (N-[2-(mercaptomethyl)-1-oxo-3-phenylpropyl]leucine); SQ-28603 (N-[2-(mercaptomethyl)-1-oxo-3-phenylpropyl]-β-alanine); SQ-29072 (7-[[2-(mercaptomethyl)-1-oxo-3-phenylpropyl]amino]heptanoic acid); thiorphan and its prodrug racecadotril; UK-69578 (cis-4-[[[1-[2-carboxy-3-(2-methoxyethoxy)propyl]cyclopentyl]carbonyl]amino]cyclohexanecarboxylic acid); UK-447,841 (2-{1-[3-(4-chlorophenyl)propylcarbamoyl]-cyclopentylmethyl}-4-methoxybutyric acid); UK-505,749 ((R)-2-methyl-3-{1-[3-(2-methylbenzothiazol-6-yl)propylcarbamoyl]cyclopentyl}propionic acid); 5-biphenyl-4-yl-4-(3-carboxypropionylamino)-2-methylpentanoic acid and 5-biphenyl-4-yl-4-(3-carboxypropionylamino)-2-methyl-pentanoic acid ethyl ester (WO 2007/056546); daglutril [(3S,2'R)-3-{1-[2'-(ethoxycarbonyl)-4'-phenylbutyl]-cyclopentan-1-carbonylamino}-2,3,4,5-tetrahydro-2-oxo-1H-1-benzazepine-1-acetic acid] described in WO 2007/106708 to Khder et al. (Novartis AG); and combinations thereof. In a particular embodiment, the NEP inhibitor is selected from AHU-377, candoxatril, candoxatrilat, CGS-24128, phosphoramidon, SCH-32615, SCH-34826, SQ-28603, thiorphan, and combinations thereof. In a particular embodiment, the NEP inhibitor is a compound such as daglutril or CGS-26303 ([N-[2-(biphenyl-4-yl)-1(S)-(1H-tetrazol-5-yl)ethyl]amino]methylphosphonic acid), which have activity both as inhibitors of the endothelin converting enzyme (ECE) and of NEP. Other dual acting ECE/NEP compounds can also be used. The NEP inhibitor will be administered in an amount sufficient to provide from about 20-800 mg per day, with typical daily dosages ranging from 50-700 mg per day, more commonly 100-600 or 100-300 mg per day.

In one embodiment, Compound 1 is administered in combination with a nitric oxide donor, examples of which include: nicorandil; organic nitrates such as pentaerythritol tetranitrate; and sydnonimines such as linsidomine and molsidomine.

In yet another embodiment, Compound 1 is administered in combination with a non-steroidal anti-inflammatory agent (NSAID), examples of which include: acemetacin, acetyl salicylic acid, alclofenac, alminoprofen, amfenac, amiprilose, aloxiprin, anirolac, apazone, azapropazone, benorilate, benoxaprofen, bezpiperylon, broperamole, bucloxic acid, carprofen, clidanac, diclofenac, diflunisal, diftalone, enolicam, etodolac, etoricoxib, fenbufen, fenclofenac, fenclozic acid, fenoprofen, fentiazac, feprazone, flufenamic acid, flufenisal, fluprofen, flurbiprofen, furofenac, ibufenac, ibuprofen, indomethacin, indoprofen, isoxepac, isoxicam, ketoprofen, ketorolac, lofemizole, lornoxicam, meclofenamate, meclofenamic acid, mefenamic acid, meloxicam, mesalamine, miroprofen, mofebutazone, nabumetone, naproxen, niflumic acid, oxaprozin, oxpinac, oxyphenbutazone, phenylbutazone, piroxicam, pirprofen, pranoprofen, salsalate, sudoxicam, sulfasalazine, sulindac, suprofen, tenoxicam, tiopinac, tiaprofenic acid, tioxaprofen, tolfenamic acid, tolmetin, triflumidate, zidometacin, zomepirac, and combinations thereof. In a particular embodiment, the NSAID is selected from etodolac, flurbiprofen, ibuprofen, indomethacin, ketoprofen, ketorolac, meloxicam, naproxen, oxaprozin, piroxicam, and combinations thereof.

In one embodiment, Compound 1 is administered in combination with an N-methyl d-aspartate (NMDA) receptor antagonist, examples of which include amantadine, dextromethorphan, dextropropoxyphene, ketamine, ketobemidone, memantine, methadone, and so forth.

In still another embodiment, Compound 1 is administered in combination with an opioid receptor agonist (also referred to as opioid analgesics). Representative opioid receptor agonists include: buprenorphine, butorphanol, codeine, dihydrocodeine, fentanyl, hydrocodone, hydromorphone, levallorphan, levorphanol, meperidine, methadone, morphine, nalbuphine, nalmefene, nalorphine, naloxone, naltrexone, nalorphine, oxycodone, oxymorphone, pentazocine, propoxyphene, tramadol, and combinations thereof. In certain embodiments, the opioid receptor agonist is selected from codeine, dihydrocodeine, hydrocodone, hydromorphone, morphine, oxycodone, oxymorphone, tramadol, and combinations thereof.

In a particular embodiment, Compound 1 is administered in combination with a phosphodiesterase (PDE) inhibitor, particularly a PDE-V inhibitor. Representative PDE-V inhibitors include avanafil, lodenafil, mirodenafil, sildenafil (Revatie), tadalafil (Adcirca®), vardenafil (Levitra®), and udenafil.

In another embodiment, Compound 1 is administered in combination with a prostaglandin analog (also referred to as prostanoids or prostacyclin analogs). Representative prostaglandin analogs include beraprost sodium, bimatoprost, epoprostenol, iloprost, latanoprost, tafluprost, travoprost, and treprostinil, with bimatoprost, latanoprost, and tafluprost being of particular interest.

In yet another embodiment, Compound 1 is administered in combination with a prostaglandin receptor agonist, examples of which include bimatoprost, latanoprost, travoprost, and so forth.

Compound 1 may also be administered in combination with a renin inhibitor, examples of which include aliskiren, enalkiren, remikiren, and combinations thereof.

In another embodiment, Compound 1 is administered in combination with a selective serotonin reuptake inhibitor (SSRI), examples of which include: citalopram and the citalopram metabolite desmethyl-citalopram, dapoxetine, escitalopram (e.g., escitalopram oxalate), fluoxetine and the fluoxetine desmethyl metabolite norfluoxetine, fluvoxamine (e.g., fluvoxamine maleate), paroxetine, sertraline and the sertraline metabolite demethylsertraline, and combinations thereof.

In one embodiment, Compound 1 is administered in combination with a 5-HT$_{1D}$ serotonin receptor agonist, examples of which include, triptans such as almotriptan, avitriptan, eletriptan, frovatriptan, naratriptan, rizatriptan, sumatriptan, and zolmitriptan.

In one embodiment, Compound 1 is administered in combination with a sodium channel blocker, examples of which include carbamazepine, fosphenytoin, lamotrigine, lidocaine, mexiletine, oxcarbazepine, phenytoin, and combinations thereof.

In one embodiment, Compound 1 is administered in combination with a soluble guanylate cyclase stimulator or activator, examples of which include ataciguat, riociguat, and combinations thereof.

In one embodiment, Compound 1 is administered in combination with a tricyclic antidepressant (TCA), examples of which include amitriptyline, amitriptylinoxide, butriptyline, clomipramine, demexiptiline, desipramine, dibenzepin, dimetacrine, dosulepin, doxepin, imipramine, imipraminoxide, lofepramine, melitracen, metapramine, nitroxazepine, nortriptyline, noxiptiline, pipofezine, propizepine, protriptyline, quinupramine, and combinations thereof.

In one embodiment, Compound 1 is administered in combination with a vasopressin receptor antagonist, examples of which include conivaptan and tolvaptan.

Combined secondary therapeutic agents may also be helpful in further combination therapy with the compound of the invention. For example, the compound of the invention can be combined with a diuretic and an ARB, or a calcium channel blocker and an ARB, or a diuretic and an ACE inhibitor, or a calcium channel blocker and a statin. Specific examples include, a combination of the ACE inhibitor enalapril (in the maleate salt form) and the diuretic hydrochlorothiazide, which is sold under the mark Vaseretic®, or a combination of the calcium channel blocker amlodipine (in the besylate salt form) and the ARB olmesartan (in the medoxomil prodrug form), or a combination of a calcium channel blocker and a statin, all may also be used with Compound 1. Other therapeutic agents such as $\alpha_2$-adrenergic receptor agonists and vasopressin receptor antagonists may also be helpful in combination therapy. Exemplary $\alpha_2$-adrenergic receptor agonists include clonidine, dexmedetomidine, and guanfacine.

The following formulations illustrate representative pharmaceutical compositions of the invention.

Exemplary Hard Gelatin Capsules for Oral Administration

The compound of the invention (50 g), 440 g spray-dried lactose and 10 g magnesium stearate are thoroughly blended. The resulting composition is then loaded into hard gelatin capsules (500 mg of composition per capsule). Alternately, Compound 1 (20 mg) is thoroughly blended with starch (89 mg), microcrystalline cellulose (89 mg) and magnesium stearate (2 mg). The mixture is then passed through a No. 45 mesh U.S. sieve and loaded into a hard gelatin capsule (200 mg of composition per capsule).

Alternately, Compound 1 (30 g), a secondary agent (20 g), 440 g spray-dried lactose and 10 g magnesium stearate are thoroughly blended, and processed as described above.

Exemplary Gelatin Capsule Formulation for Oral Administration

Compound 1 (100 mg) is thoroughly blended with polyoxyethylene sorbitan monooleate (50 mg) and starch powder (250 mg). The mixture is then loaded into a gelatin capsule (400 mg of composition per capsule). Alternately, Compound 1 (70 mg) and a secondary agent (30 mg) are thoroughly blended with polyoxyethylene sorbitan monooleate (50 mg) and starch powder (250 mg), and the resulting mixture loaded into a gelatin capsule (400 mg of composition per capsule).

Alternately, Compound 1 (40 mg) is thoroughly blended with microcrystalline cellulose (Avicel PH 103; 259.2 mg) and magnesium stearate (0.8 mg). The mixture is then loaded into a gelatin capsule (Size #1, White, Opaque) (300 mg of composition per capsule).

Exemplary Hydroxypropyl Methylcellulose (HPMC) Capsule for Oral Administration

Compound 1 (50 mg or 100 mg) is loaded directly into a HPMC capsule.

Exemplary Tablet Formulation for Oral Administration

Compound 1 (10 mg), starch (45 mg) and microcrystalline cellulose (35 mg) are passed through a No. 20 mesh U.S. sieve and mixed thoroughly. The granules so produced are dried at 50-60° C. and passed through a No. 16 mesh U.S. sieve. A solution of polyvinylpyrrolidone (4 mg as a 10% solution in sterile water) is mixed with sodium carboxymethyl starch (4.5 mg), magnesium stearate (0.5 mg), and talc (1 mg), and this mixture is then passed through a No. 16 mesh U.S. sieve. The sodium carboxymethyl starch, magnesium stearate and talc are then added to the granules. After mixing, the mixture is compressed on a tablet machine to afford a tablet weighing 100 mg.

Alternately, Compound 1 (250 mg) is thoroughly blended with microcrystalline cellulose (400 mg), silicon dioxide fumed (10 mg), and stearic acid (5 mg). The mixture is then compressed to form tablets (665 mg of composition per tablet).

Alternately, Compound 1 (400 mg) is thoroughly blended with cornstarch (50 mg), croscarmellose sodium (25 mg), lactose (120 mg), and magnesium stearate (5 mg). The mixture is then compressed to form a single-scored tablet (600 mg of composition per tablet).

Alternately, Compound 1 (100 mg) is thoroughly blended with cornstarch (100 mg) with an aqueous solution of gelatin (20 mg). The mixture is dried and ground to a fine powder. Microcrystalline cellulose (50 mg) and magnesium stearate (5 mg) are then admixed with the gelatin formulation, granulated and the resulting mixture compressed to form tablets (100 mg of the compound of the invention per tablet).

Exemplary Suspension Formulation for Oral Administration

The following ingredients are mixed to form a suspension containing 100 mg of Compound 1 per 10 mL of suspension:

| Exemplary Liquid Formulation for Oral Administration | |
|---|---|
| Ingredients | Amount |
| Compound 1 | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |

-continued

| Exemplary Liquid Formulation for Oral Administration | |
| --- | --- |
| Ingredients | Amount |
| Sorbitol (70% solution) | 12.85 g |
| Veegum ® K (magnesium aluminum silicate) | 1.0 g |
| Flavoring | 0.035 mL |
| Colorings | 0.5 mg |
| Distilled water | q.s. to 100 mL |

A suitable liquid formulation is one with a carboxylic acid-based buffer such as citrate, lactate and maleate buffer solutions. For example, Compound 1 (which may be pre-mixed with DMSO) is blended with a 100 mM ammonium citrate buffer and the pH adjusted to pH 5, or is blended with a 100 mM citric acid solution and the pH adjusted to pH 2. Such solutions may also include a solubilizing excipient such as a cyclodextrin, for example the solution may include 10 wt % hydroxypropyl-β-cyclodextrin.

Other suitable formulations include a 5% NaHCO$_3$ solution, with or without cyclodextrin.

Exemplary Parenteral IV Formulation for Administration by Injection

Compound 1 (0.2 g) is blended with 0.4 M sodium acetate buffer solution (2.0 mL). The pH of the resulting solution is adjusted to pH 4 using 0.5 N aqueous hydrochloric acid or 0.5 N aqueous sodium hydroxide, as necessary, and then sufficient water for injection is added to provide a total volume of 20 mL. The mixture is then filtered through a sterile filter (0.22 micron) to provide a sterile solution suitable for administration by injection.

The following formulations illustrate representative pharmaceutical compositions of the present invention.

Formulation Example A

A frozen solution suitable for preparing an injectable solution is prepared as follows:

| Ingredients | Amount |
| --- | --- |
| Active Compound 1 or 1' | 10 to 1000 mg |
| Excipients (e.g., dextrose) | 0 to 50 g |
| Water for Injection Solution | 10 to 100 mL |

Representative Procedure: The excipients, if any, are dissolved in about 80% of the water for injection and the active Compound 1 or 1' is added and dissolved. The pH is adjusted with 1 M sodium hydroxide to 3 to 4.5 and the volume is then adjusted to 95% of the final volume with water for injection. The pH is checked and adjusted, if necessary, and the volume is adjusted to the final volume with water for injection. The formulation is then sterile filtered through a 0.22 micron filter and placed into a sterile vial under aseptic conditions. The vial is capped, labeled and stored frozen.

Formulation Example B

A lyophilized powder or crystalline solid suitable for preparing an injectable solution is prepared as follows:

| Ingredients | Amount |
| --- | --- |
| Active Compound 1 or 1' | 10 to 1000 mg |
| Excipients (e.g., mannitol and/or sucrose) | 0 to 50 g |
| Buffer Agent (e.g., citrate) | 0 to 500 mg |
| Water for Injection | 10 to 100 mL |

Representative Procedure: The excipients and/or buffering agents, if any, are dissolved in about 60% of the water for injection. The active Compound 1 or 1' is added and dissolved and the pH is adjusted with 1 M sodium hydroxide to 3 to 4.5 and the volume is adjusted to 95% of the final volume with water for injection. The pH is checked and adjusted, if necessary, and the volume is adjusted to the final volume with water for injection. The formulation is then sterile filtered through a 0.22 micron filter and placed into a sterile vial under aseptic conditions. The formulation is then freeze-dried using an appropriate lyophilization cycle. The vial is capped (optionally under partial vacuum or dry nitrogen), labeled and stored under refrigeration.

Formulation Example C

An injectable solution for intravenous administration to a patient is prepared from Formulation Example B above as follows:

Representative Procedure: The lyophilized powder of Formulation Example B (e.g., containing 10 to 1000 mg of active Compound 1 or 1') is reconstituted with 20 mL of sterile water and the resulting solution is further diluted with 80 mL of sterile saline in a 100 mL infusion bag. The diluted solution is then administered to the patient intravenously over 30 to 120 minutes.

Exemplary Compositions for Administration by Inhalation

Compound 1 (0.2 mg) is micronized and then blended with lactose (25 mg). This blended mixture is then loaded into a gelatin inhalation cartridge. The contents of the cartridge are administered using a dry powder inhaler, for example.

Alternately, micronized Compound 1 (10 g) is dispersed in a solution prepared by dissolving lecithin (0.2 g) in demineralized water (200 mL). The resulting suspension is spray dried and then micronized to form a micronized composition comprising particles having a mean diameter less than about 1.5 µm. The micronized composition is then loaded into metered-dose inhaler cartridges containing pressurized 1,1,1,2-tetrafluoroethane in an amount sufficient to provide about 10 µg to about 500 µg of the compound of the invention per dose when administered by the inhaler.

Alternately, Compound 1 (25 mg) is dissolved in citrate buffered (pH 5) isotonic saline (125 mL). The mixture is stirred and sonicated until the compound is dissolved. The pH of the solution is checked and adjusted, if necessary, to pH 5 by slowly adding aqueous 1 N NaOH. The solution is administered using a nebulizer device that provides about 10 µg to about 500 µg of Compound 1 per dose.

Examples

The following Preparations and Examples are provided to illustrate specific embodiments of the invention. These specific embodiments, however, are not intended to limit the scope of the invention in any way unless specifically indicated.

The following abbreviations have the following meanings unless otherwise indicated and any other abbreviations used herein and not defined have their standard, generally accepted meaning:

| | |
|---|---|
| AcOH | acetic acid |
| BOC | t-butoxycarbonyl (—C(O)OC(CH$_3$)$_3$) |
| (BOC)$_2$O | di-t-butyl dicarbonate |
| Bn | benzyl |
| CPME | cyclopentyl methyl ether |
| DCC | 1,3-dicyclohexylcarbodiimide |
| DCM | dichloromethane or methylene chloride |
| DIPE | diisopropyl ether |
| DIPEA | N,N-diisopropylethylamine |
| DMAP | 4-dimethylaminopyridine |
| DMF | N,N-dimethylformamide |
| Et$_3$N | triethylamine |
| EtOH | ethanol |
| Et$_2$O | diethyl ether |
| EtOAc | ethyl acetate |
| MeCN | acetonitrile |
| NaHMDS | sodium bis(trimethylsilyl)amide |
| Pd(PPh$_3$)$_4$ | tetrakis(triphenylphosphine)palladium(0) |
| PE | petroleum ether |
| SilicaCat ®DPP—Pd | silica based diphenylphosphine palladium (II) catalyst |
| TFA | trifluoroacetic acid |
| THF | tetrahydrofuran |

Unless noted otherwise, all materials, such as reagents, starting materials and solvents, were purchased from commercial suppliers (such as Sigma-Aldrich, Fluka Riedel-de Haën, and the like) and were used without further purification.

Reactions were run under nitrogen atmosphere, unless noted otherwise. The progress of reactions were monitored by thin layer chromatography (TLC), analytical high performance liquid chromatography (anal. HPLC), and mass spectrometry, the details of which are given in specific examples. Generally, solvents used in analytical HPLC were as follows: solvent A was 98% H$_2$O/2% MeCN/1.0 mL/L TFA; solvent B was 90% MeCN/10% H$_2$O/1.0 mL/L TFA.

Reactions were worked up as described specifically in each preparation for example; commonly reaction mixtures were purified by extraction and other purification methods such as temperature-, and solvent-dependent crystallization, and precipitation. In addition, reaction mixtures were routinely purified by preparative HPLC, typically using Microsorb C18 and Microsorb BDS column packings and conventional eluents. Progress of reactions was typically measured by liquid chromatography mass spectrometry (LCMS). Characterization of isomers was done by Nuclear Overhauser effect spectroscopy (NOE). Characterization of reaction products was routinely carried out by mass and $^1$H-NMR spectrometry. For NMR measurement, samples were dissolved in deuterated solvent (CD$_3$OD, CDCl$_3$, or DMSO-d$_6$), and $^1$H-NMR spectra were acquired with a Varian Gemini 2000 instrument (400 MHz) under standard observation conditions. Mass spectrometric identification of compounds was typically conducted using an electrospray ionization method (ESMS) with an Applied Biosystems (Foster City, Calif.) model API 150 EX instrument or an Agilent (Palo Alto, Calif.) model 1200 LC/MSD instrument.

Measurement Techniques

Powder X-Ray Diffraction

Powder X-ray diffraction analysis was performed using a Bruker D8-Advance X-ray diffractometer. The X-ray source was Cu-Kα radiation with output voltage of 40 kV and current of 40 mA. The instrument was operated in Bragg-Brentano geometry and used Goebel Mirrors to obtain parallel X-ray beam. Any divergence in the beam was limited by a 0.2° vertical divergence slit at the source and Soller slits (2.5°) at the source and the detector. For measurement, a small amount of powder (5-25 mg) was gently pressed onto a zero-background silicon sample-holder to form a smooth surface and subjected to X-ray exposure. The samples were scanned in coupled θ-2θ mode from 2° to 35° in 2θ with a step size of 0.02° and a scan speed of 0.3 seconds per step. The data acquisition was controlled by Bruker DiffracSuite software and analyzed by Jade software (version 7.5.1). The instrument was calibrated with a corundum standard, within ±0.02° 2θ angle.

It should be kept in mind that the Bragg-Brentano geometry used in the data collection is prone to preferred orientation. Under these conditions it is possible that the relative intensities of the diffraction peaks may not represent the true relative intensities that would be obtained from an idealized distribution of spherical particles or from a diffraction pattern simulated from a single crystal data. It is also possible that some peaks are not seen in some diffraction patterns due to the extensive preferred orientation.

Differential Scanning Calorimetry

DSC measurements were performed using a TA Instruments Model Q-100 module with a Thermal Analyst controller. Data were collected and analyzed using TA Instruments Universal Analysis software. A sample was accurately weighed into a covered aluminum pan. After a 5 minute isothermal equilibration period at 5° C., the sample was heated using a linear heating ramp of 10° C./min from 0° C. up to 275° C.

Thermogravimetric Analysis

TGA measurements were performed using a TA Instruments Model Q-500 module equipped with high resolution capability. Data were collected using TA Instruments Thermal Analyst controller and analyzed using TA Instruments Universal Analysis software. A weighed sample was placed onto a platinum pan and scanned with a heating rate of 10° C. from ambient temperature to 200° C. The balance and furnace chambers were purged with nitrogen flow during use.

Polarized Light Microscopy

For polarized light microscopy (PLM) studies, samples were examined under an optical microscope (Olympus BX51) with cross-polarized light filter. Images were collected with a PaxCam camera controlled by PaxIt Imaging Software (version 6.4). Samples were prepared on glass slides with light mineral oil as immersion medium. Depending on the size of the particles, a 4×, a 10× or a 20× objective lens was used for magnification.

Dynamic Moisture Sorption Assessment

DMS measurements were performed using a VTI atmospheric microbalance, SGA-100 system (VTI Corp., Hialeah, Fla. 33016). A weighed sample was used and the humidity was lowest possible value (close to 0% relative humidity) at the start of the analysis. The DMS analysis consisted of a scan rate of 5% relative humidity/step over the full humidity range of 5-90%. The DMS run was performed isothermally at 25° C.

Synthetic Procedures and Comparative Examples

The following compounds were synthesized and evaluated for NEP enzyme inhibition activity:

| Compound Name | General Designation | Preparation/ Example | Structure |
|---|---|---|---|
| Compound 1 | Compound | Preparation 1/ Example 1 | 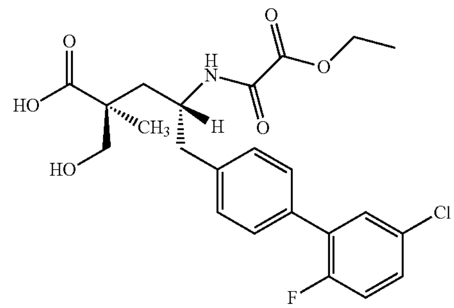 [SMILES: CCOC(=O)C(=O)N[C@H](Cc1ccc(-c2cc(Cl)ccc2F)cc1)C[C@@](C)(CO)C(=O)O] |
| Comparison Compound C2 | Active Metabolite | Preparation 2/ Example 2 | 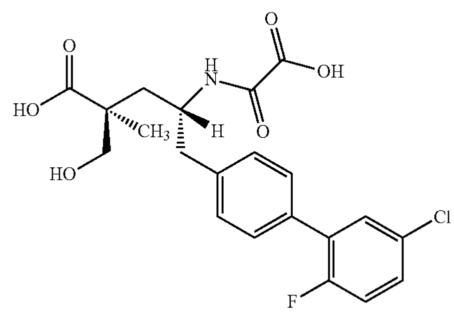 [SMILES: C[C@@](CO)(C[C@@H](Cc1ccc(-c2cc(Cl)ccc2F)cc1)NC(=O)C(=O)O)C(=O)O] |
| Comparison Compound C3 | Compound or Prodrug | Preparations 3 and 4/ Example 3 | 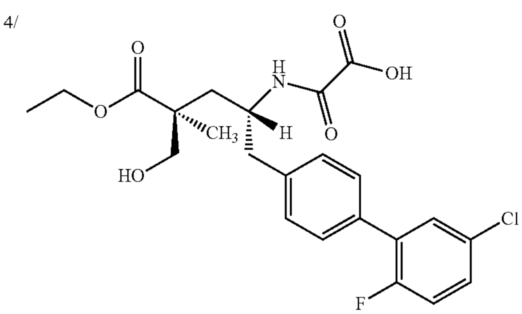 |
| Comparison Compound C4 | Compound or Prodrug | Preparations 5, 6, 7, and 8/ Example 4 | 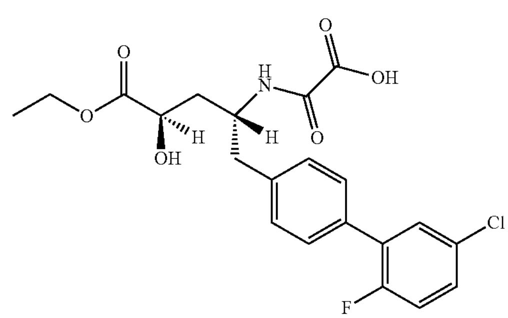 [SMILES: CCOC(=O)[C@H](O)C[C@@H](Cc1ccc(-c2cc(Cl)ccc2F)cc1)NC(=O)C(=O)O] |

-continued

| Compound Name | General Designation | Preparation/Example | Structure |
|---|---|---|---|
| Comparison Compound C5 | Compound or Prodrug | Preparation 9/Example 5 | 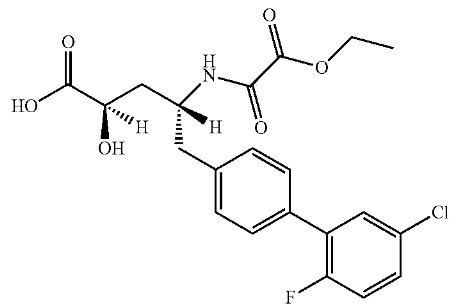 [SMILES: CCOC(=O)C(=O)N[C@H](Cc1ccc(-c2cc(Cl)ccc2F)cc1)C[C@@H](O)C(=O)O] |
| Comparison Compound C6 | Active Metabolite | Example 6 | 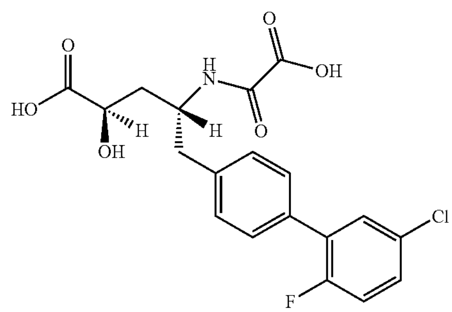 [SMILES: O=C(O)C(=O)N[C@H](Cc1ccc(-c2cc(Cl)ccc2F)cc1)C[C@@H](O)C(=O)O] |

Preparation 1: (2S,4R)-4-Amino-5-(5'-chloro-2'-fluorobiphenyl-4-yl)-2-hydroxymethyl-2-methylpentanoic acid benzyl ester (Compound 7)

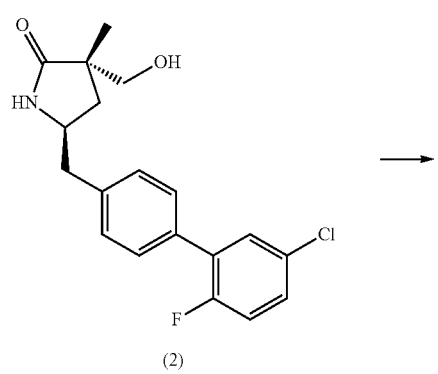

(2)

(3S,5R)-5-(5'-Chloro-2'-fluoro-biphenyl-4-ylmethyl)-3-hydroxymethyl-3-methyl-pyrrolidin-2-one (2) (201.0 g, 578 mmol) was combined with DCM (4020 mL) to yield a homogenous clear brown solution which was then cooled to 0° C. with stirring. 3,4-dihydro-2H-pyran (118 mL, 1.3 mol) and 4-methylbenzenesulfonic acid (34.8 g, 202 mmol) were added and the mixture was heated to 18.5° C. over 2 hours, then stirred at 18.5° C. overnight (>98% conversion). The reaction was quenched with saturated aqueous NaHCO$_3$, and the phases were allowed to separate. The organic layer was dried with Na$_2$SO$_4$, then filtered, followed by solvent removal to yield a thick dark brown crude (~300 g), which was dissolved in DIPE (2 L) and stirred at 5° C. overnight to yield a white slurry. The slurry was filtered, and the solids dried over 2 days to yield Compound 3 (113.8 g). The filtrate was dried yielding a thick oil, which was dissolved in DIPE (~100 mL) and stirred overnight at 5° C. to isolate additional Compound 3 (total yield 225 g)

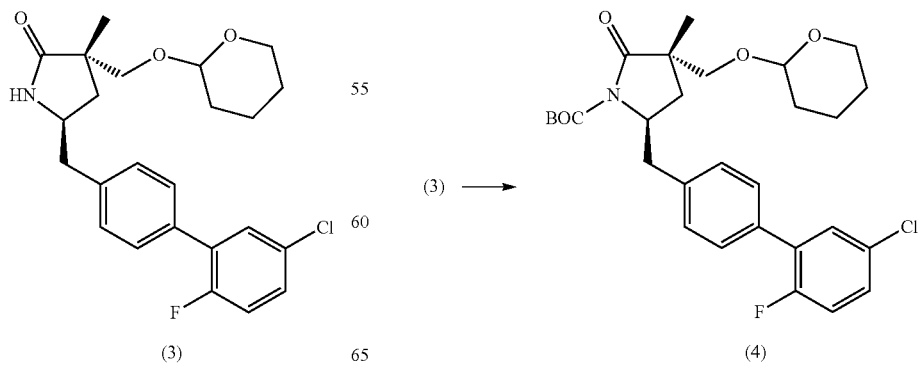

(3) → (4)

Compound 3 (208 g, 482 mmol) was dissolved in THF (1912 mL, 23 mol) with stirring to yield a clear homogeneous solution. The mixture was purged with nitrogen and then cooled to −10° C. 1M NaHMDS in THF (539 mL, 539 mmol) was added dropwise and the mixture was stirred for 30 minutes. di-t-Butyl dicarbonate (131 g, 602 mmol) dissolved in THF (393 mL, 4.8 mol) was added dropwise and the resulting mixture was stirred at room temperature overnight. The reaction was quenched with saturated aqueous NH₄Cl (5.0 L) and EtOAc (3.1 L) was added. The phases were separated and the organic layer was washed with saturated aqueous NaCl (5.0 L). The phases were separated and the organic layer was dried over MgSO₄. Solvent removal yielded a thick oil which upon further drying over two days yielded Compound 4 (265 g) as a foamed up solid.

Compound 5 (277.0 g, 498 mmol) was dissolved in DMF (970 mL) to yield a colorless solution. K₂CO₃ (103 g, 747 mmol) was added and resulting mixture was stirred for 15 minutes. Benzyl bromide (71.1 ml, 598 mmol) was added in one portion and the mixture was stirred at room temperature overnight; complete conversion after 20 hours. NH₄Cl (6 L) and EtOAc (1 L) were added and the phases were separated. The organic layer was washed with saturated aqueous NaCl (6 L), and dried over Na₂SO₄, followed by solvent removal to yield crude Compound 6 (335 g), which was used directly in the next step.

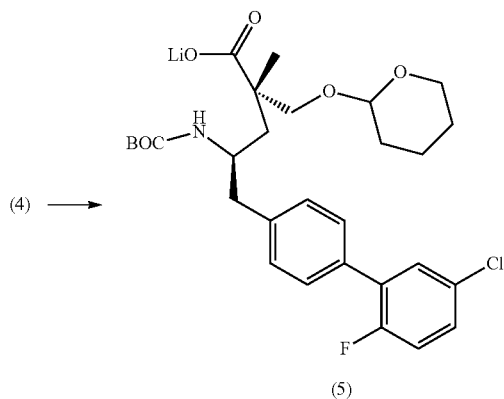

(4) →

(5)

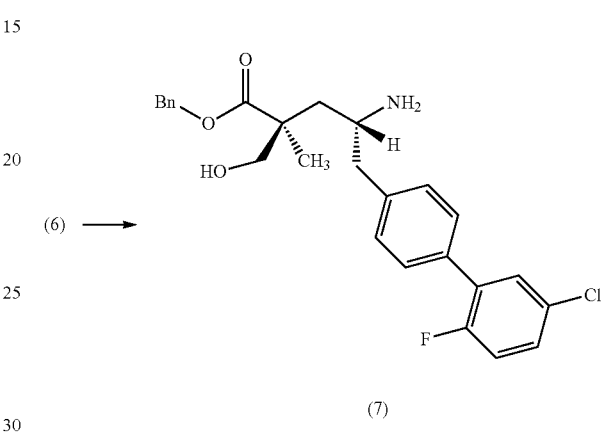

(6) →

(7)

Compound 4 (265 g, 498 mmol) was dissolved in THF (1.7 L) to yield a homogeneous clear-light brown solution. 1.0M LiOH in water (1.5 L, 1.5 mol) was added and the resulting mixture was stirred at room temperature over 4 hours. The reaction was complete after 6 hours but the mixture remained stirring at 15° C. overnight. EtOAc (1.7 L) was added, and the mixture was washed with saturated aqueous NH₄Cl (1.7 L) and the phases were separated. The organic layer was washed with saturated aqueous NaCl, separated, dried over Na₂SO₄, then filtered and dried to yield Compound 5 (300 g) as a foamed up off-white to yellow solid (overage is due to residual EtOAc).

3M HCl (1.7 L, 5.0 mol) in CPME was combined with Compound 6 (319.0 g, 498 mmol), and the resulting mixture was stirred at room temperature for over 24 hours, yielding a slurry (>99% conversion). Additional CPME (1.0 L) was added and the resulting slurry was stirred for 1 hour. The mixture was filtered and the wet cake was rinsed with CPME (500 mL). Filtration and drying yielded Compound 7 (190 g) as a white cake.

Example 1: (2S,4R)-5-(5'-Chloro-2'-fluorobiphenyl-4-yl)-4-(ethoxyoxalylamino)-2-hydroxymethyl-2-methylpentanoic Acid (Compound 1)

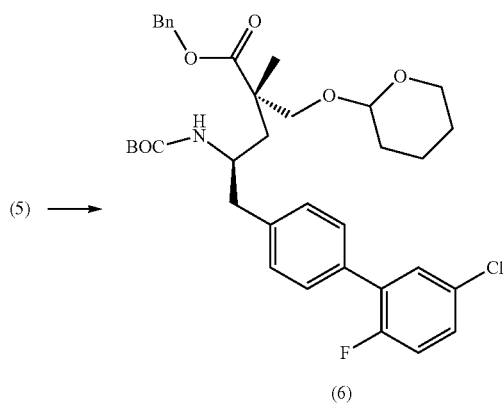 [SMILES: CC(C)(C)OC(=O)N[C@H](Cc1ccc(-c2cc(Cl)ccc2F)cc1)C[C@@](C)(COC1CCCCO1)C(=O)OCc1ccccc1]

(5) →

(6)

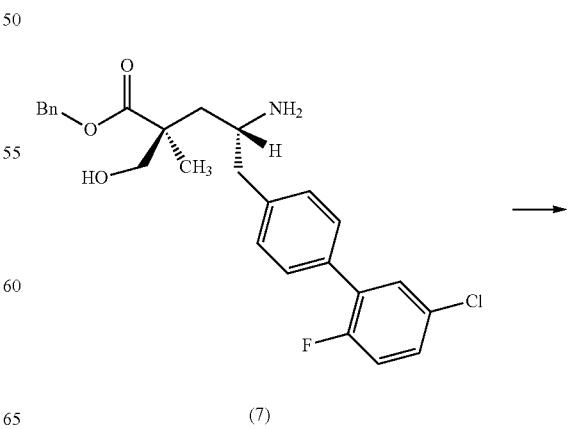

(7)

-continued

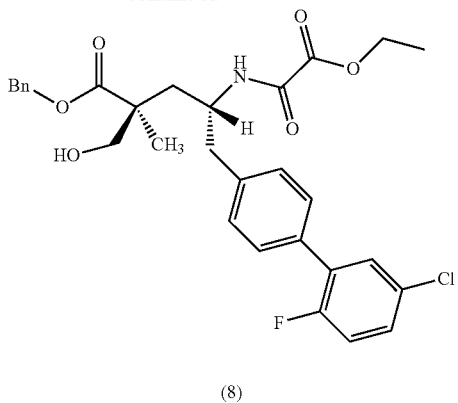

(8)

chromatography (20-95% EtOAc/hexanes) to yield Compound 8 (1.0 g, 1.9 mmol) was used directly in the next step.

(8) →

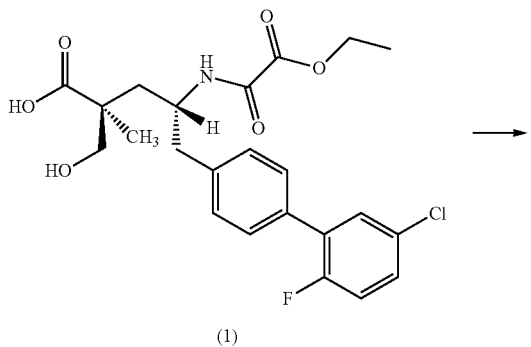

(1)

EtOH (576 μL, 9.9 mmol) was dissolved in DCM (3 mL). Oxalyl chloride (1.0 mL, 12.1 mmol) was added, and the resulting solution was stirred at room temperature for 30 minutes. The solvent was evaporated without heat, yielding a solution which was used directly the next step. (2S,4R)-4-Amino-5-(5'-chloro-2'-fluorobiphenyl-4-yl)-2-hydroxymethyl-2-methylpentanoic acid benzyl ester (7) (1.0 g, 2.2 mmol) was dissolved in DCM (3 mL). The previously obtained solution was added, followed by DIPEA (958 μL, 5.5 mmol). The resulting solution was stirred at room temperature for 15 minutes, at which point LC/MS showed the mass of the desired product. The solvent was removed in vacuo and the crude residue was purified by normal phase Compound 8 (1.0 g, 1.9 mmol) was combined with palladium 10 wt % on carbon (350 mg, 185 μmol), AcOH (5 mL) and EtOAc (5 mL). The mixture was placed under hydrogen and stirred at room temperature for 2 hours, at which point LC/MS showed completion of the benzyl deprotection. The palladium was filtered off using a 0.2 μm PTFE Acrodisc CR filter and the solvent was removed in vacuo. The crude residue was purified by reverse phase chromatography to yield Compound 1 (400 mg). MS m/z [M+H]$^+$ calc'd for $C_{23}H_{25}ClFNO_6$, 466.14. found 466.

Crystalline Calcium (2S,4R)-5-(5'-Chloro-2'-fluoro-[1,1'-biphenyl]-4-yl)-4-(2-ethoxy-2-oxoacetamido)-2-(hydroxymethyl)-2-methylpentanoate (Compound 1')

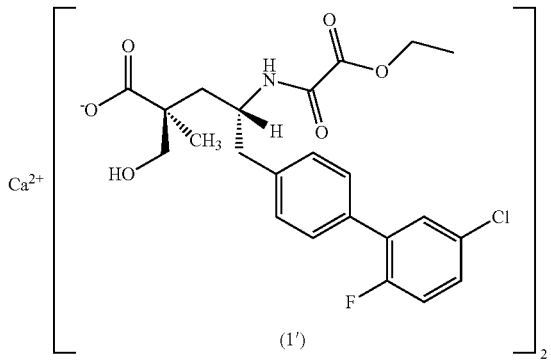

Compound 1 (30 g, 64.4 mmol) was dissolved in 200-proof EtOH (100 mL) and DIPEA (11.25 mL, 64.4 mmol) was subsequently added to this mixture at room temperature. Calcium trifluoromethane sulfonate (10.89 g, 32.2 mmol) was dissolved in EtOH (20 mL) and added dropwise to the mixture containing Compound 1 to form a thick slurry over the course of approximately 1 hour. The thick slurry was then stirred at room temperature for two days. The resulting slurry was slowly filtered and dried over two days to yield 33 g of >99% pure Compound 1'. A second reslurry process was performed by first cooling Compound 1' (33 g, 19.80 mmol) to 5° C. A cold EtOH:water (7:3) mixture (300 mL) was then added and the resulting slurry was stirred vigorously for 4 days. The slurry was then slowly filtered and dried for 24 hours with continuous de-lumping. The slurry was then dried in air at room temperature for an additional 18 hours to yield 29.5 g of >99% pure solid of Compound 1'. This product was analyzed by PXRD, DSC and TGA, as described herein, and data generated is presented in FIGS. 1-3.

Crystalline L-Arginine (2S,4R)-5-(5'-Chloro-2'-fluoro-[1,1'-bipheny]-4-yl)-4-(2-ethoxy-2-oxoacetamido)-2-(hydroxymethyl)-2-methylpentanoate (Compound 1")

solution was cooled at −20° C. for about 10 minutes. In a separate glass vial, L-arginine (68 mg) was dissolved in 0.2 mL of water and the solution was cooled at 5° C. for about 10 minutes. The clear solution containing Compound 1 was slowly transferred to the L-arginine solution. An additional 0.2 mL of 200-proof EtOH was added to the vial previously containing Compound 1 and the contents were further added to the vial containing the L-arginine solution. Seeds of L-arginine crystals obtained from an earlier reaction using a similar procedure just described were added to the combined solution and the entire mixture was kept at 5° C. with gentle stirring to yield a crystalline suspension between 1-2 days. Crystals of Compound 1" were filtered and analyzed by PXRD, DSC and TGA, as described herein, and data generated is presented in FIGS. 6-8.

Preparation 2: (2S,4R)-4-t-Butoxycarbonylamino-5-(5'-chloro-2'-fluorobiphenyl-4-yl)-2-hydroxymethyl-2-methylpentanoic Acid Ethyl Ester (Compound 10)

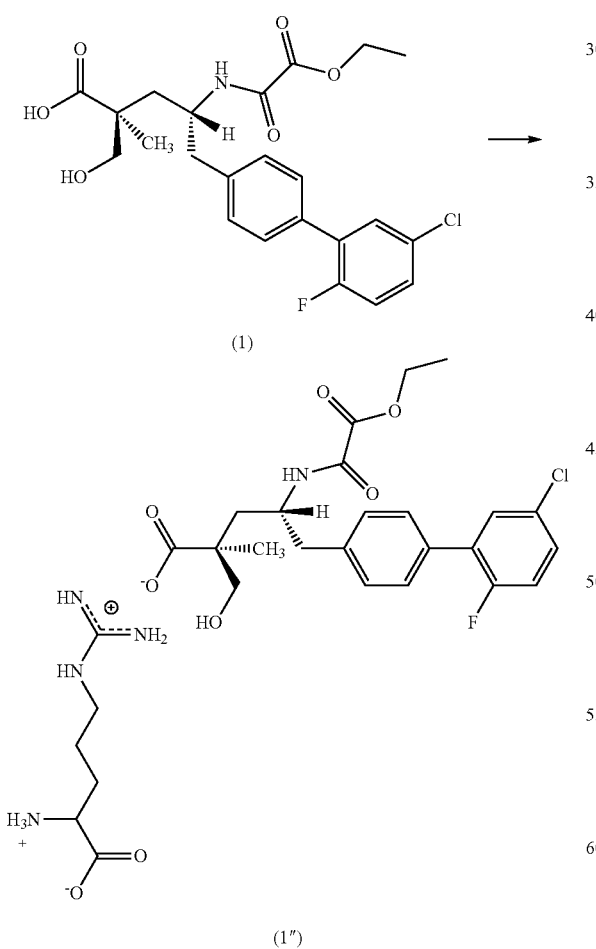

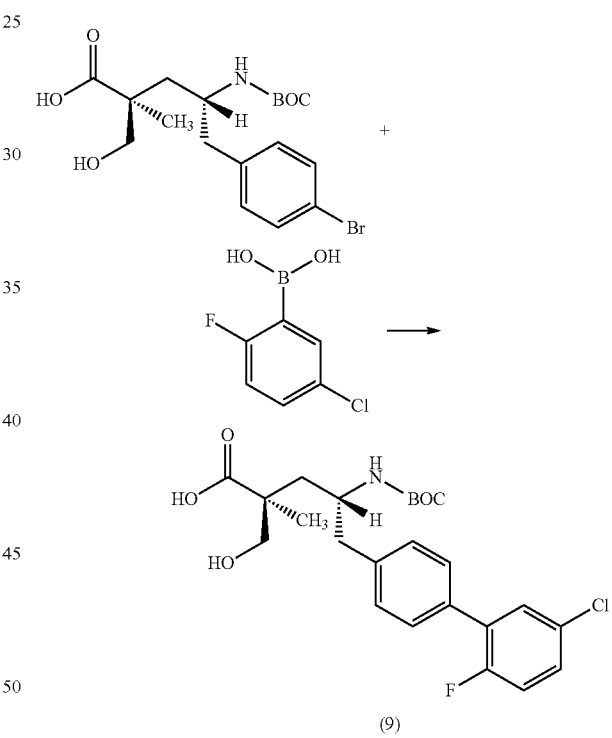

(2S,4R)-5-(4-bromophenyl)-4-t-butoxycarbonylamino-2-hydroxymethyl-2-methylpentanoic acid (1.3 g, 3.1 mmol) was combined with $Na_2CO_3$ (993 mg, 9.4 mmol), water (0.2 mL) and dioxane (1.5 mL). The reaction vessel was capped, purged, and placed under nitrogen. $Pd(PPh_3)_4$ (541 mg, 468 µmol) was quickly added and the vessel was again purged. The mixture was heated for 45 minutes at 90° C., at which point LCMS showed reaction completion. The organic layer was acidified with 1N HCl/water to pH ~4 and extracted with EtOAc. The organic layer was separated, washed with saturated aqueous NaCl and dried over $Mg_2SO_4$. The solvent was removed in vacuo and the crude residue was purified by reverse phase chromatography to yield Compound 9.

Compound 1 (181.6 mg) was dissolved in 200-proof EtOH (0.5 mL) in a glass vial to afford a clear solution. The

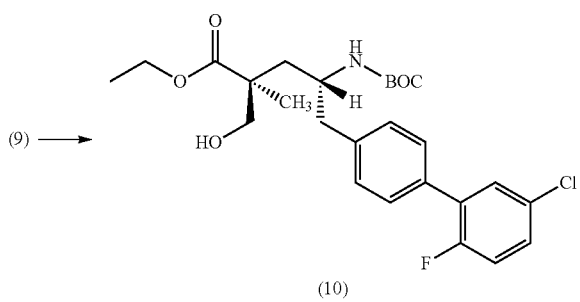 [SMILES: CCOC(=O)[C@](C)(CO)C[C@@H](Cc1ccc(-c2cc(Cl)ccc2F)cc1)NC(=O)OC(C)(C)C]

Compound 9 (1.0 g, 2.1 mmol) was dissolved in EtOH (4 mL) and 4N HCl in dioxane (4 mL) and stirred for 3 hours at 60° C. The solvents were evaporated and the crude residue was dissolved in DCM. (BOC)$_2$O (472 µL, 2.031 mmol) and Et$_3$N (566 µL, 4.1 mmol) were added followed by DMAP (5 mg). The reaction mixture was stirred for 3 hours. The crude was evaporated and was triturated with DCM and filtered w/o further purification to yield Compound 10 (800 mg).

To crude Compound 11 (2.1 g, 5.3 mmol) in DCM (10 mL) was added ethyl 2-chloro-2-oxoacetate (1.3 mL, 11.7 mmol), followed by the slow addition of Et$_3$N (2.6 mL, 18.7 mmol). The resulting mixture was stirred for 15 minutes and the reaction monitored for completion. The crude product was purified by flash chromatography (0-100% EtOAc/hexanes) to yield Compound 12, which was used directly in the next step.

Example 2: (2S,4R)-5-(5'-Chloro-2'-fluorobiphenyl-4-yl)-2-hydroxymethyl-2-methyl-4-(oxalylamino)pentanoic Acid (Comparison Compound C2)

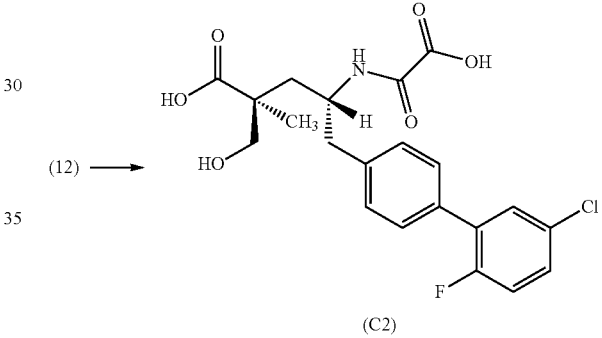

Compound 12 (2.2 g, 3.7 mmol) was combined with THF (5 mL) and NaOH (3.7 mL, 37.0 mmol), followed by the addition of water (10 mL). The resulting mixture was stirred overnight. The solvent was evaporated, AcOH was added and the product was purified by reverse phase chromatography to yield Comparison Compound C2 (540 mg). MS m/z [M+H]$^+$ calc'd for C$_{21}$H$_{21}$ClFNO$_6$, 438.10. found 438.2.

Comparison Compound C2 is described in example 11-2 of U.S. Pat. No. 8,691,868 to Hughes et al.

Preparation 3: (3S,5R)-5-(5'-Chloro-T-fluorobiphenyl-4-ylmethyl)-3-hydroxymethyl-3-methylpyrrolidin-2-one (Compound 21)

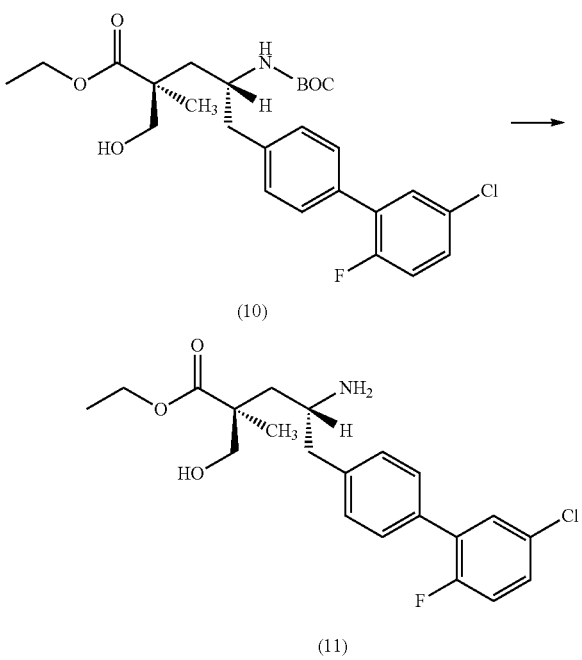

(2S,4R)-4-t-Butoxycarbonylamino-5-(5'-chloro-2'-fluorobiphenyl-4-yl)-2-hydroxymethyl-2-methylpentanoic acid ethyl ester (10) (2.6 g, 5.3 mmol) was combined with MeCN (5 mL) and 4N HCl in dioxane (4 mL) and stirred for 15 minutes. The solvent was removed by centrifugal evaporation to yield Compound 11, which was used directly in the next step.

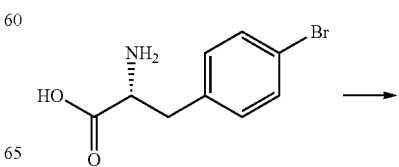

-continued

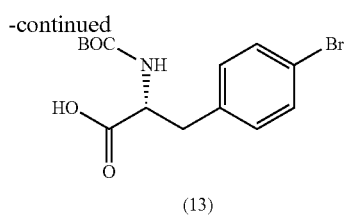

(13)

A solution of (R)-2-amino-3-(4-bromophenyl)propionic acid (3300 g, 13.5 mol, 1.0 eq.) in MeCN (46.2 L) was placed in a reaction flask that had been purged and maintained with an inert atmosphere of nitrogen. A solution of NaOH (1081 g, 27.0 mol, 2.0 eq.) in water (46.2 L) was added in several batches at −10° C. To this was added a solution of di-t-butyl dicarbonate (2948 g, 13.51 mol, 1.0 eq.) in MeCN (6.6 L). The resulting solution was stirred overnight at room temperature, then concentrated in vacuo. The resulting solution was diluted with 45 L of water/ice. The solution pH was adjusted to 2 with HCl (1 mol/L). The resulting solution was extracted with DCM (50 L×3) and the organic layers combined. The resulting mixture was washed with saturated aqueous NaCl (50 L), then dried over $MgSO_4$ and concentrated in vacuo to yield Compound 13 (3720 g) as a white solid.

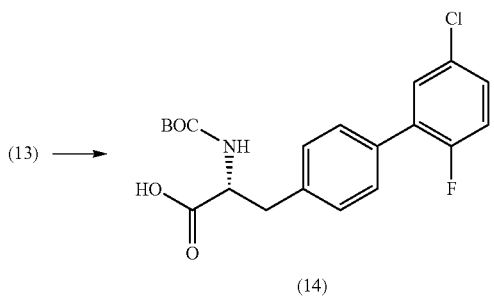 [SMILES: CC(C)(C)OC(=O)N[C@H](Cc1ccc(-c2cc(Cl)ccc2F)cc1)C(=O)O]

(13) →

(14)

A solution of Compound 13 (530 g, 1.54 mol, 1.0 eq.) in dioxane (9.54 L) was combined with (5-chloro-2-fluorophenyl)boronic acid (348 g, 2.0 mol, 1.3 eq.), a solution of $Na_2CO_3$ (228 g, 2.2 mol, 1.4 eq.) in water (1.1 L), and $Pd(PPh_3)_4$ (8.9 g, 7.7 mmol, 0.01 eq.) in a reaction flask that had been purged and maintained with an inert atmosphere of nitrogen. The resulting solution was heated to reflux for 2.5 hours in an oil bath, then cooled to room temperature with a water/ice bath. The resulting solution was diluted with EtOAc (15 L), washed with 1N HCl (5 L) and saturated aqueous NaCl (5 L×4). The combined organics were then dried over $MgSO_4$ and concentrated in vacuo. The residue was washed then with PE (1 L×2) to yield Compound 14 (510 g) as a brown oil.

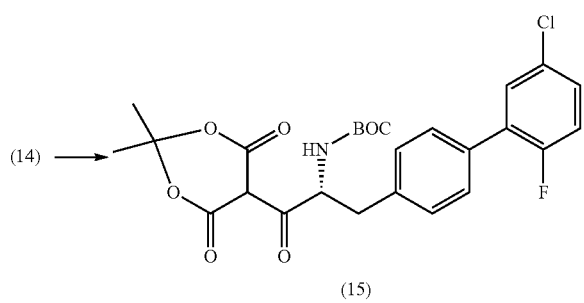 [SMILES: CC(C)(C)OC(=O)N[C@H](Cc1ccc(-c2cc(Cl)ccc2F)cc1)C(=O)C1C(=O)OC(C)(C)OC1=O]

(14) →

(15)

A solution of Compound 14 (510 g, 1.3 mol, 1.0 eq.) in DCM (5 L) was combined with 2,2-dimethyl-1,3-dioxane-4,6-dione (205 g, 1.4 mol, 1.1 eq.) and 4-dimethylaminopyridine (237 g, 1.9 mol, 1.5 eq.) in a reaction flask that had been purged and maintained with an inert atmosphere of nitrogen. A solution of DCC (294 g, 1.4 mol, 1.1 eq.) in DCM (600 mL) was added dropwise with stirring at −10° C. The resulting solution was stirred overnight at room temperature. The solids were filtered, and the filtrate was washed with 1 N HCl (2 L) and saturated aqueous NaCl (3 L). The combined organics were dried over $MgSO_4$. The solids were filtered, to yield Compound 15 as the filtrate, which was used in the next step directly without further purification.

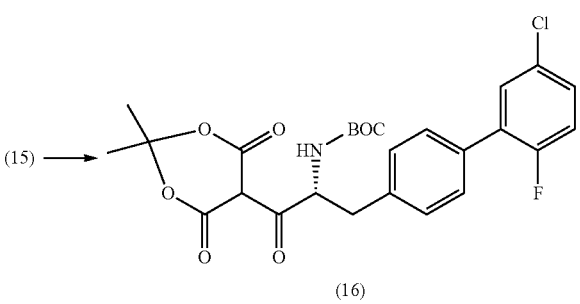 [SMILES: CC(C)(C)OC(=O)N[C@H](Cc1ccc(-c2cc(Cl)ccc2F)cc1)C(=O)C1C(=O)OC(C)(C)OC1=O]

(15) →

(16)

A solution of Compound 15 in DCM (7 L, crude) was combined with AcOH (600 mL) in a reaction flask that had been purged and maintained with an inert atmosphere of nitrogen. $NaBH_4$ (88.8 g, 2.4 mol, 1.8 eq.) was added in several batches at −5° C. The resulting solution was stirred for 3 hours at −5° C. The reaction was then quenched by the dropwise addition of saturated aqueous NaCl (1 L). The resulting solution was diluted with saturated aqueous NaCl (2 L) and the resulting mixture was washed with water (2 L×2), saturated aqueous $NaHCO_3$ (1 L), and saturated aqueous NaCl (2 L). The combined organics were dried over $MgSO_4$ and concentrated in vacuo to yield Compound 16 (520 g) as a yellow oil.

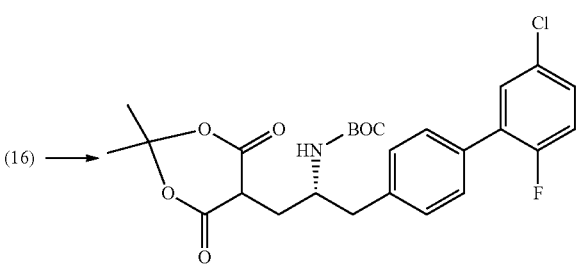

(16) →

(17)

A solution of Compound 16 (520 g, 1.0 mol, 1.0 eq.) in acetone/DMF (1:1) (5.2 L) was combined with $Na_2CO_3$ (163 g, 1.5 mol, 1.5 eq.) and methyl iodide (219 g, 1.5 mol, 1.5 eq.) in a reaction flask that had been purged and maintained with an inert atmosphere of nitrogen. The resulting solution was stirred overnight at room temperature, then diluted with water (15 L). After stirring for 1 hour the solids were collected by filtration. The residue was dissolved in DCM (5 L). The combined organics were dried over $MgSO_4$ and concentrated in vacuo to yield Compound 17 (520 g) as a yellow solid.

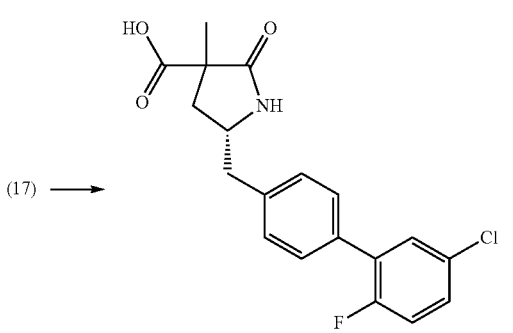

(17) →

→

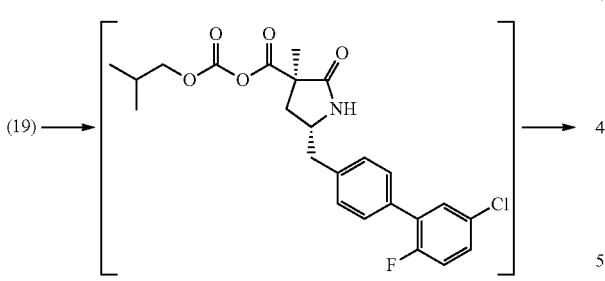

A solution of Compound 17 (520 g, 1.0 mol, 1.0 eq.) in CPME (2.6 L) was placed in a reaction flask that had been purged and maintained with an inert atmosphere of nitrogen. A 4N solution of HCl in CPME (2.6 L) was added at −5° C. The resulting solution was stirred overnight at room temperature, then concentrated to half of the volume in vacuo (yielding Compound 18). The solids were collected by filtration, then washed with a 1:2 mixture of EtOAc and DIPE to yield Compound 19 (220 g) as an off-white solid.

(19) →

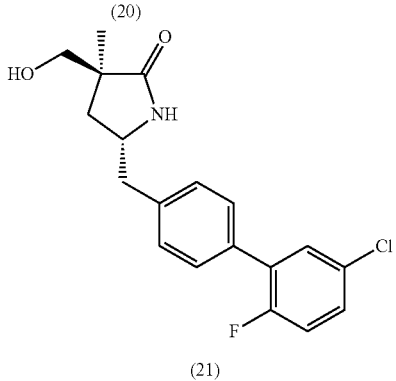

A solution of Compound 19 (218 g, 602.5 mmol, 1.0 eq.) in THF (4 L) and N-methylmorpholine (170 g, 1.7 mol, 2.8 eq.) was placed in a reaction flask that had been purged and maintained with an inert atmosphere of nitrogen. 2-methyl-propyl chloroformate (164.4 g, 1.2 mol, 2.0 eq.) was added dropwise with stirring at −5° C. The resulting solution was stirred for 20 minutes at −5° C. A solution of $NaBH_4$ (91.5 g, 2.4 mol, 4.0 eq.) in water (400 mL) was then added dropwise with stirring at −5° C. The resulting solution was stirred for an additional 1 hour at room temperature. The reaction was then quenched by the dropwise addition of 1N HCl (2.6 L), and the resulting mixture was stirred for 1 hour and then concentrated in vacuo. The residual mixture was then stirred for another 1 hour, and then the solids were collected by filtration. The solids were washed with water, dissolved in THF, dried over $Na_2SO_4$, and concentrated in vacuo to yield Compound 21 (170 g) as a white solid.

Preparation 4: (2S,4R)-4-t-Butoxycarbonylamino-5-(5'-chloro-2'-fluorobiphenyl-4-yl)-2-hydroxymethyl-2-methylpentanoic Acid Benzyl Ester (Compound 23)

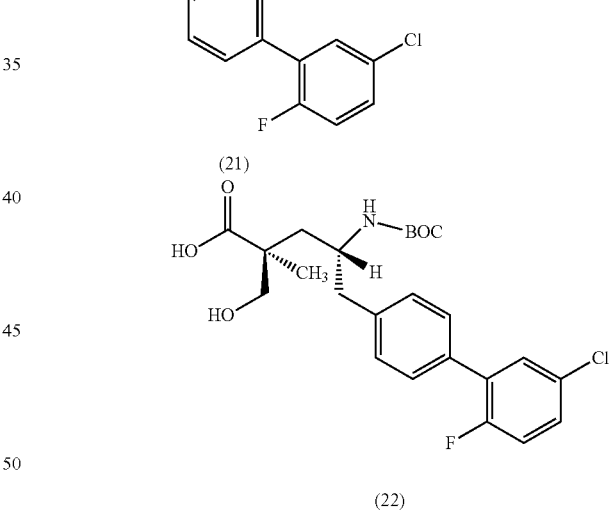

(3S,5R)-5-(5'-chloro-2'-fluorobiphenyl-4-ylmethyl)-3-hydroxymethyl-3-methylpyrrolidin-2-one (21) (5.0 g, 14.4 mmol) was dissolved in THF (10 mL) and placed under nitrogen. The solution was put in an ice bath. NaHMDS (31.6 mL, 31.6 mmol) was added and the mixture was stirred for 10 minutes from 0° C. to room temperature. $(BOC)_2O$ (7.3 mL, 31.6 mmol) was then added and the mixture was stirred for 1 hour at room temperature, at which point LC/MS showed completion. To this crude solution was added a solution of 10N NaOH (21.6 ml, 216 mmol) in water to achieve a pH-12. Additional THF (~10 mL) was added and the solution was stirred overnight at room temperature, at which point LC/MS showed completion. EtOAc was added followed by a solution of 1N HCl until reaching a pH 5. The organic layer was extracted, dried over MgSO₄, filtered, and evaporated. The crude residue was purified by normal phase chromatography (50-100% EtOAc/hexanes) to yield Compound 22 (2.5 g).

(22) ⟶

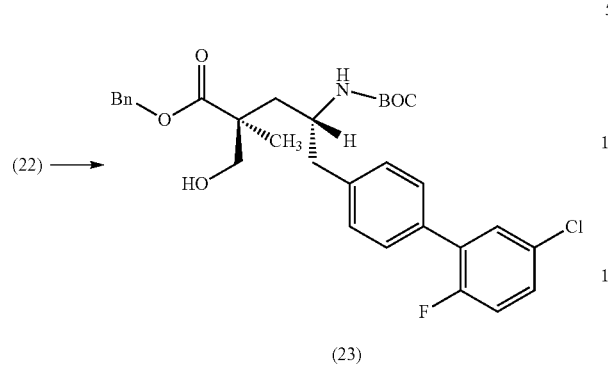

(23)

Compound 22 (550 mg, 1.2 mmol), K₂CO₃ (179 mg, 1.3 mmol) and benzyl bromide (154 µL, 1.3 mmol) were combined in DMF (6 mL) and stirred for 3-4 hours at room temperature, at which point LC/MS showed completion. The solvent was removed in vacuo and the crude residue was purified by normal phase chromatography to yield Compound 23 (453 mg).

Example 3: (2S,4R)-5-(5'-Chloro-2'-fluorobiphenyl-4-yl)-2-hydroxymethyl-2-methyl-4-(oxalylamino) pentanoic Acid Ethyl Ester (Comparison Compound C3)

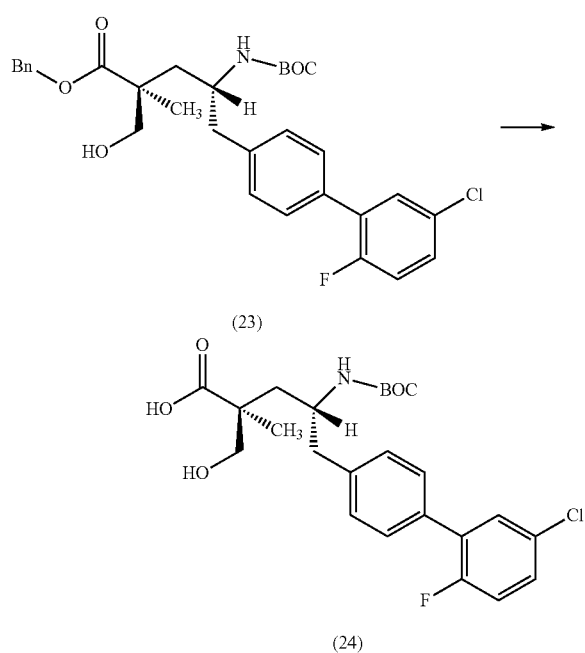

(23)

(24)

AcOH (376 µL, 6.6 mmol) was added to a solution of (2S,4R)-4-t-butoxycarbonylamino-5-(5'-chloro-2'-fluorobiphenyl-4-yl)-2-hydroxymethyl-2-methylpentanoic acid benzyl ester (23) (730 mg, 1.3 mmol) followed by palladium (140 mg, 131 µmol). The resulting mixture was stirred under hydrogen for 3 hours, at which point LCMS showed reaction completion. The mixture was filtered using a 0.2 µm PTFE Acrodisc CR filter, and concentrated to yield Compound 24 (599 mg) as a clear colorless viscous liquid.

(24) ⟶

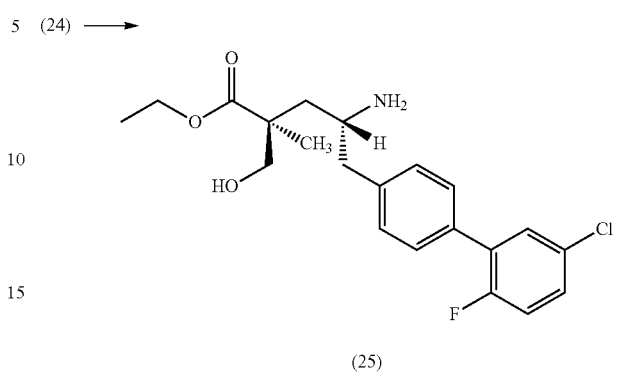

(25)

4N HCl in dioxane (4.8 mL, 19.3 mmol) was added to a solution of Compound 24 (599 mg, 1.3 mmol) in EtOH (5 mL). The resulting mixture was stirred at 80° C. for 3 hours, then concentrated in vacuo to yield a clear colorless liquid. The crude liquid was purified by reverse phase chromatography (20-90% MeCN in water with 0.05% TFA) to yield Compound 25 (455 mg) as a white gum HCl salt.

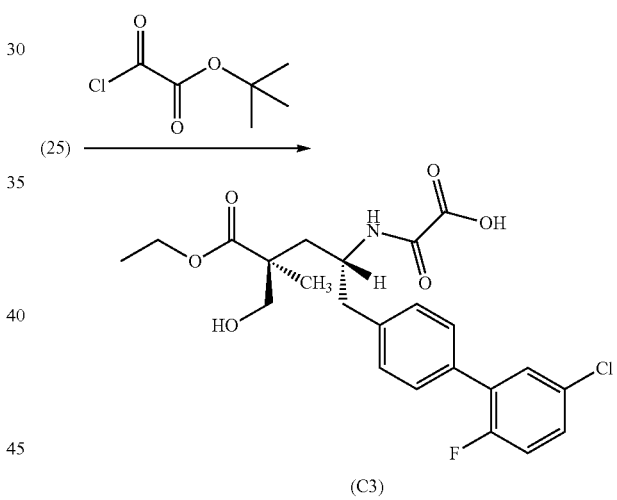

(C3)

t-Butanol (574 µL, 6.0 mmol) was added to a solution of oxalyl chloride (772 µL, 9.0 mmol) in DCM (3 mL) at 0° C., and the mixture was stirred at room temperature for 30 minutes. The reaction mixture was then concentrated in vacuo to yield t-butyl 2-chloro-2-oxoacetate (403 mg) as a clear colorless liquid. The liquid was dissolved in DCM (2.5 mL) to prepare a 1.0 M solution in DCM.

DIPEA (261 µL, 1.5 mmol) was added to a solution of Compound 25 (236 mg, 599 µmop in DCM (3.0 mL) followed by t-butyl 2-chloro-2-oxoacetate (1M solution in DCM; 659 µL, 659 µmol), and the mixture was stirred at room temperature for 15 minutes. TFA (3.0 mL) was then added and the mixture was stirred at room temperature for 30 minutes. The mixture was concentrated in vacuo to yield a clear pale yellow liquid. The crude liquid was purified by reverse phase chromatography (20-90% MeCN in water with 0.05% TFA) to yield Comparison Compound C3 (174 mg) as a white solid. MS m/z [M+H]⁺ calc'd for $C_{23}H_{25}ClFNO_6$, 466.14. found 466.

Preparation 5: (S)-2-(4-Bromobenzyl)-5-oxopyrrolidine-1-carboxylic Acid t-Butyl Ester (Compound 28)

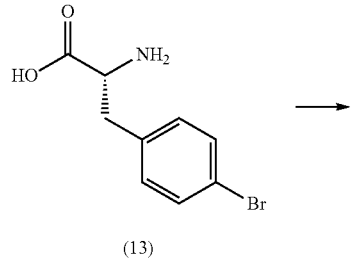

(13)

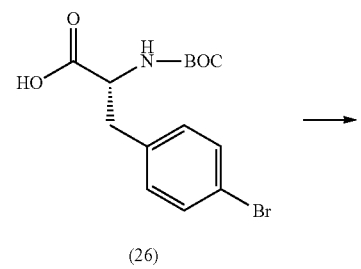

(26)

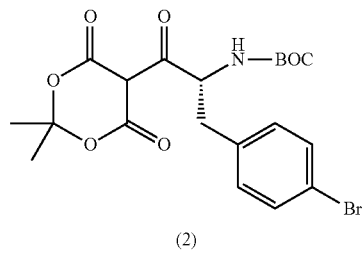

(2)

To a solution of (R)-2-amino-3-(4-bromophenyl)propionic acid (50 g, 0.2 mol) in MeCN (700 mL) was added a solution of NaOH (16.4 g, 0.4 mol) in water (700 mL) at −5° C. After stirring for 10 minutes, a solution of (BOC)$_2$O (44.7 g, 0.2 mol) in MeCN (100 mL) was added. The mixture was warmed to room temperature and stirred overnight. After the evaporation of the MeCN, the residue was diluted with DCM (800 mL) and acidified with 1 M HCl to pH 2 at −5° C. The aqueous was extracted with DCM (3×200 mL). The combined organic layers were washed with saturated aqueous NaCl (500 mL), dried over Na$_2$SO$_4$ and concentrated to yield Compound 13 (66.5 g) as a white solid. LC-MS: 366 [M+Na], 709 [2M+Na].

To a solution of Compound 13 (66.5 g, 193 μmol), Meldrum's acid (33.4 g, 232 mmol) and DMAP (37.7 g, 309 mmol) in anhydrous DCM (600 mL), was added dropwise a solution of DCC (47.9 g, 232 mmol) in anhydrous DCM (200 mL) over 1 hour at −5° C. under nitrogen. The mixture was stirred at −5° C. for 8 hours, then refrigerated overnight. Crystals of dicyclohexylurea were observed. The mixture was filtered, washed with 5% KHSO$_4$ (5×200 mL) and saturated aqueous NaCl (200 mL), then dried over anhydrous MgSO$_4$ under refrigeration overnight. The solution was then evaporated to yield crude Compound 26 (91 g) as a light yellow solid. LC-MS: 492 [M+Na], 961 [2M+Na].

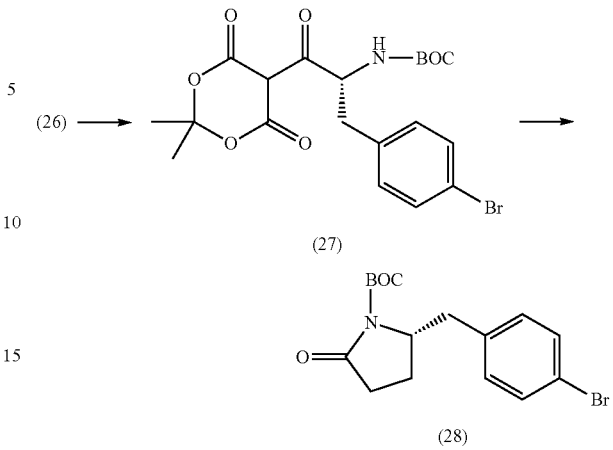

To a solution of crude Compound 26 (91 g, 193 mmol) in anhydrous DCM (1 L) was added AcOH (127.5 g, 2.1 mol) at −5° C. under nitrogen. The mixture was stirred at −5° C. for 30 minutes, then NaBH$_4$ (18.3 g, 483 mmol) was added in small portions over 1 hour. After stirring for another 1 hour at −5° C., saturated aqueous NaCl (500 mL) was added. The organic layer was washed with saturated aqueous NaCl (2×300 mL) and water (2×300 mL), dried over MgSO$_4$, filtered, and concentrated to yield the crude product, which was further purified by washing with Et$_2$O to yield Compound 27 (68 g) as a light yellow solid. LC-MS: 478 [M+Na], 933 [2M+Na].

A solution of Compound 27 (68 g, 149 mmol) in anhydrous toluene (500 mL) was refluxed under nitrogen for 3 hours. After evaporation of the solvent, the residue was purified by chromatography (hexanes:EtOAc=10:1) to yield Compound 28 (38 g) as a light yellow oil. LC-MS: 376 [M+Na], 729 [2M+Na].

Preparation 6: (2R,4R)-4-Amino-5-(4-bromophenyl)2-hydroxypentanoic Acid Ethyl Ester (Compound 33)

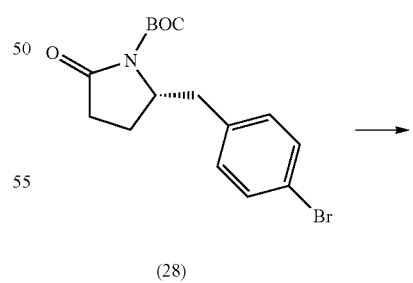

(28)

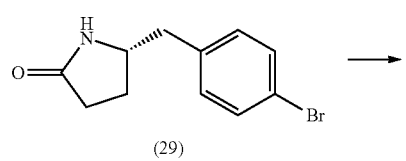

(29)

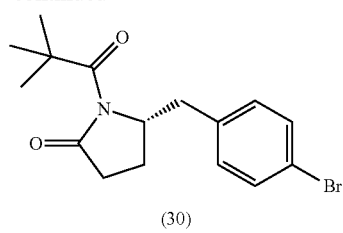

(30)

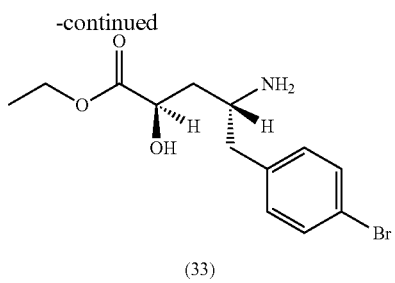

(33)

To a solution of (S)-2-(4-bromobenzyl)-5-oxopyrrolidine-1-carboxylic acid t-butyl ester (28) (38 g, 107 mmol) in anhydrous DCM (250 mL) was added TFA (20 mL, 0.27 mol) at −5° C. under nitrogen. The mixture was warmed to room temperature and stirred overnight. After evaporation of the solvent, the residue was diluted with EtOAc (300 mL) and washed with saturated aqueous $NaHCO_3$ (3×200 mL), water (200 mL), saturated aqueous NaCl (250 mL), dried over $Na_2SO_4$ and concentrated to yield crude Compound 29 (24 g) as a light yellow solid. LC-MS: 254 [M+H].

To a solution of NaH (8.6 g, 250 mmol) in anhydrous THF (200 mL) was added dropwise a solution of Compound 29 (24 g, 94 mmol) in anhydrous THF (200 mL) over 30 minutes at 0° C. under nitrogen. The mixture was warmed to room temperature and stirred for 2 hours. After cooling to 0° C., pivaloyl chloride (18 g, 150 mmol) was added dropwise over 30 minutes. The mixture was warmed to room temperature and stirred overnight. The reaction was quenched with saturated aqueous $NH_4Cl$ (300 mL) and extracted with EtOAc (3×200 mL). The combined organic layers were washed with saturated aqueous NaCl (300 mL), dried over $MgSO_4$, filtered and concentrated to yield the crude product, which was further purified by chromatography (hexanes: EtOAc=25:1) to yield Compound 30 (18 g) as a light yellow solid. LC-MS: 360 (M+Na).

To a solution of Compound 30 (18 g, 53 mmol) in anhydrous THF (250 mL) was added dropwise NaHMDS (47.7 mL, 96 mmol) over 30 minutes at −78° C. under nitrogen. After stirring at −78° C. for 90 minutes, a solution of (+)-(8,8-dichlorocamphorylsulfonyl)-oxaziridine (31.6 g, 106 mmol) was added dropwise over 30 minutes. After stirring at −78° C. for 2 hours, the reaction was quenched with saturated aqueous $NH_4Cl$ (400 mL) and extracted with EtOAc (3×300 mL). The combined organic layers were washed with saturated aqueous NaCl (300 mL), dried over $MgSO_4$, filtered, and concentrated to give the crude product which was further purified by chromatography (hexanes: EtOAc=15:1) to yield Compound 31 (8.9 g) as a light yellow solid. LC-MS: 376 (M+Na).

A solution of Compound 31 (8.9 g, 25 mmol) in concentrated HCl (81 mL, 81 mmol) was heated at 100° C. for 16 hours. The mixture was then concentrated to yield the crude product which was further purified by washing with $Et_2O$ to yield compound 32 (7 g) as a light yellow solid HCl salt. LC-MS: 323 (M+H).

A solution of compound 32 (7 g, 22 mmol) in EtOH (10 mL) was combined with 8M HCl in EtOH (120 mL, 960 mmol) at room temperature. The mixture was heated at 50° C. for 16 hours, then concentrated. The crude product was further purified by washing with $Et_2O$ to yield Compound 33 (6 g) as a light yellow solid HCl salt. LC-MS: 352 (M+H).

Preparation 7: Chloro-oxo-acetic acid t-Butyl Ester (Compound 34)

Oxalyl chloride (232 μL, 2.8 mmol) and t-butyl alcohol (228 μL) were combined in ether (6.7 mL) under nitrogen at 0° C. The resulting mixture was stirred for 30 minutes at room temperature. The solvent was evaporated under vacuum to form Compound 34.

Preparation 8: (2R,4R)-5-(4-Bromophenyl)-4-(t-butoxyoxalyl-amino)-2-hydroxypentanoic Acid Ethyl Ester (Compound 36)

(30) → 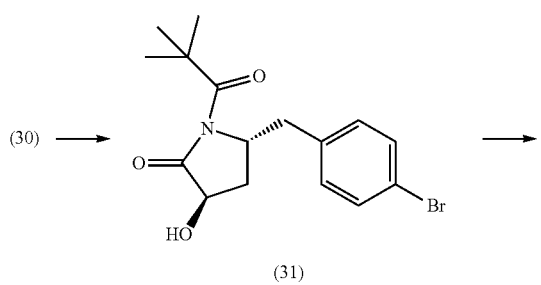

(31)

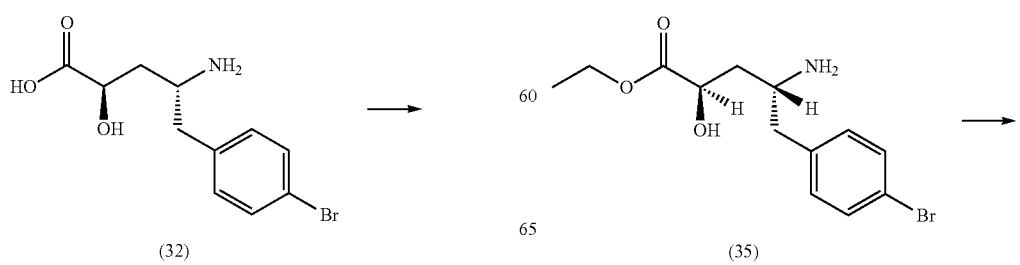

-continued

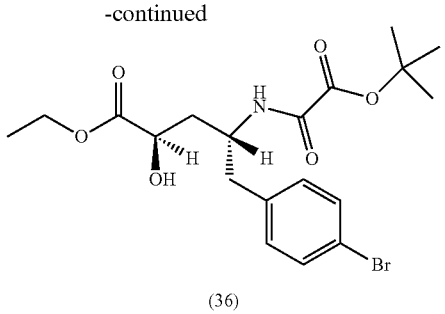

(36)

Oxalyl chloride (401 μL, 4.7 mmol) in DCM (8 mL) was combined with t-butyl alcohol (454 μL, 4.7 mmol). Et$_3$N (198 μL, 1.4 mmol) was added dropwise, and the resulting solution was stirred for 5 minutes. This solution was then added dropwise to a solution of (2R,4R)-4-amino-5-(4-bromophenyl)2-hydroxypentanoic acid ethyl ester (35) (150 mg, 474 μmop and Et$_3$N (198 μl, 1.4 mmol) in DCM (5 mL), and stirred until the reaction was complete. The solvents were evaporated and the crude was purified by normal phase chromatography (20-100% EtOAc/hexanes) to yield Compound 36.

Example 4: (2R,4R)-5-(5'-Chloro-2'-fluorobiphenyl-4-yl)-2-hydroxy-4-(oxalylamino)pentanoic Acid Ethyl Ester (Comparison Compound C4)

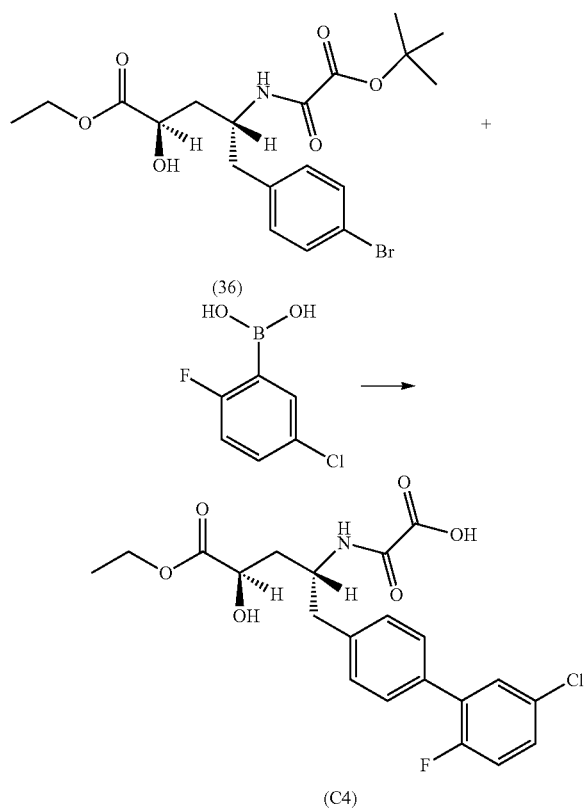

(2R,4R)-5-(4-Bromophenyl)-4-(t-butoxyoxalyl-amino)-2-hydroxypentanoic acid ethyl ester (36) (48.5 mg, 109 μmop was combined with 5-chloro-2-fluorophenylboronic acid (22.8 mg, 131 μmop and K$_2$CO$_3$ (45.2 mg, 327 μmop in t-butyl alcohol (2 mL) and water (0.3 mL). SilicaCat®DPP-Pd (0.28 mmol/g loading; 39 mg, 11 μmop was added and the mixture was heated at 80° C. for 15 minutes, at which time LC/MS showed the desired product. The mixture was filtered and the filtrate concentrated and purified by preparative HPLC to yield Comparison Compound C4 (20 mg). MS m/z [M+H]$^+$ calc'd for C$_{21}$H$_{21}$ClFNO$_6$, 438.10. found 438.0.

Comparison Compound C4 is described in example 5-6 of U.S. Pat. No. 8,691,868 to Hughes et al.

Preparation 9: (2R,4R)-4-Amino-5-(5'-chloro-2'-fluorobiphenyl-4-yl)-2-hydroxypentanoic Acid Ethyl Ester (Compound 42)

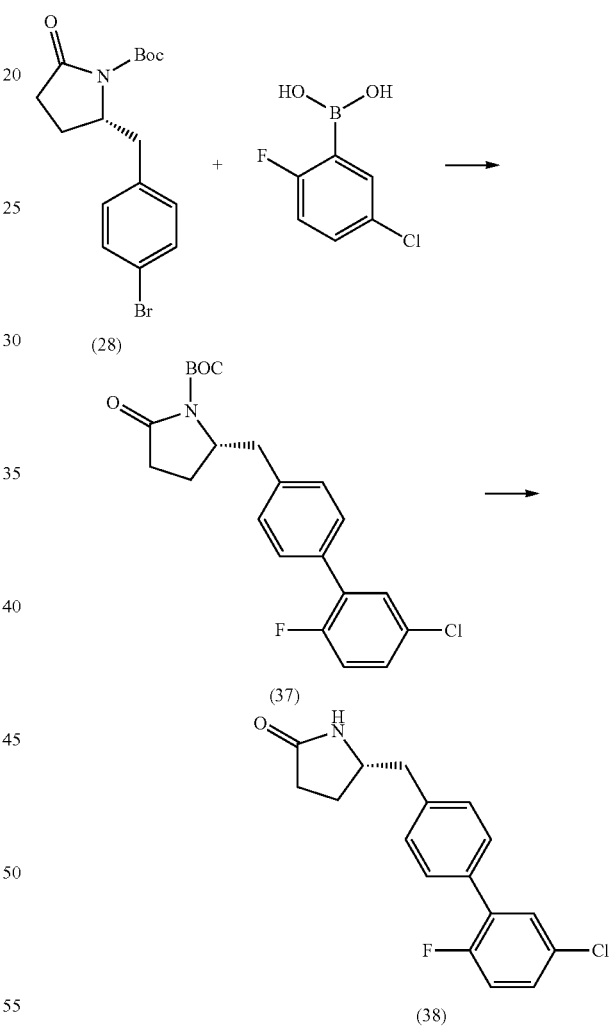

To a solution of (S)-2-(4-bromobenzyl)-5-oxopyrrolidine-1-carboxylic acid t-butyl ester (28) (25 g, 70.6 mmol) in 1,4-dioxane (500 mL) was added 5-chloro-2-fluorophenylboronic acid (24.6 g, 141 mmol), Pd(PPh$_3$)$_4$ (4.1 g, 3.5 mmol) and a solution of K$_2$CO$_3$ (17.8 g, 141 mmol) in water (90 mL), at room temperature under nitrogen. The mixture was heated to 60° C. and stirred overnight. Water (500 mL) was added and the solvent evaporated. The mixture was extracted with EtOAc (3×200 mL). The combined organic layers were washed with saturated aqueous NaCl (300 mL)

and filtered. The filtrate was concentrated to yield the crude product which was purified by chromatography to yield Compound 37 (22.7 g) as a light yellow solid. LC-MS: 829.2 [2M+Na⁺].

To a solution of Compound 37 (4.9 g, 12.1 mol) in DCM (100 mL) was added TFA (4.5 mL, 60.7 mmol) at 0° C. under nitrogen, and stirred for 1 hour. The mixture was warmed to room temperature for 1.5 hours. After evaporation of the solvent, the residue was diluted with EtOAc (100 mL), then washed with saturated aqueous NaHCO₃ (3×100 mL), water (2×100 mL), saturated aqueous NaCl (100 mL), then dried over Na₂SO₄. The mixture was filtered and the filtrate was concentrated to yield crude Compound 38 (combined with a separate lot for a total of 16.9 g). LC-MS: 304 [M+H].

(38) ⟶

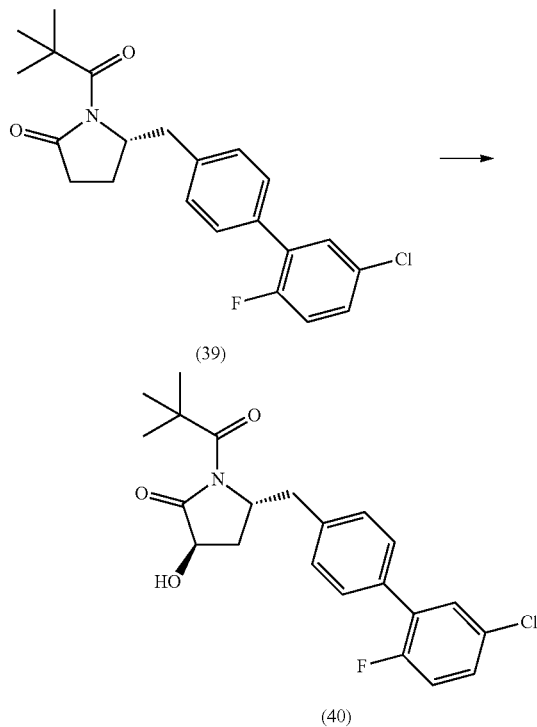

(39)

(40)

To a solution of NaH (2.4 g, 695 mmol) in THF (200 mL) was added dropwise a solution of Compound 38 (8.5 g, 278 mmol) in THF (50 mL) at 0° C. under nitrogen. The mixture was warmed to room temperature and stirred for 2 hours. After cooling to 0° C., pivaloyl chloride (5 g, 41.7 mmol) was added dropwise over 30 minutes. The mixture was warmed to room temperature and stirred for 9.5 hours. The reaction was quenched with saturated aqueous NH₄Cl (250 mL) and extracted with EtOAc (3×400 mL). The combined organic layers were dried over Na₂SO₄ and concentrated to yield the crude product which was purified by chromatography to yield Compound 39 (18 g) as a yellow solid. LC-MS: 388 [M+H⁺].

To a solution of Compound 39 (9 g, 23.2 mmol) in THF (200 mL) was added dropwise NaHMDS (20.9 mL, 41.8 mmol) at −78° C. under nitrogen. After stirring for 1 hour at −78° C., a solution of (+)-(8,8-dichlorocamphorylsulfonyl)oxaziridine (10.4 g, 34.8 mmol) in THF (50 mL) was added dropwise. After stirring at −78° C. for 1 hour, the reaction was quenched with saturated aqueous NH₄Cl (50 mL) and extracted with EtOAc (3×400 mL). The combined organic layers were washed with 1M HCl (400 mL), saturated aqueous NaHCO₃ (400 mL), and saturated aqueous NaCl (400 mL), dried over Na₂SO₄, and concentrated to give the crude product which was purified by chromatography to yield Compound 40 (8.8 g) as a white semi-solid. LC-MS: 426.1 [M+Na⁺].

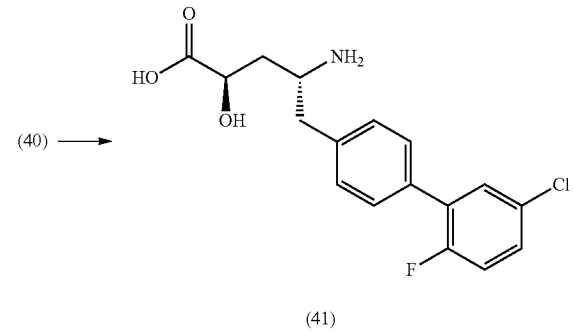 [SMILES: N[C@H](Cc1ccc(-c2cc(Cl)ccc2F)cc1)C[C@@H](O)C(=O)O]

(41)

A solution of Compound 40 (8.8 g, 21.8 mmol) in EtOH (12 mL) was added to concentrated HCl (200 mL) and heated at 100° C. and stirred overnight. The mixture was then concentrated to give the crude product which was purified by washing with Et₂O (100 mL) to yield Compound 41 as a solid HCl salt (7.5 g). LC-MS: 338 [M+H⁺].

(41) ⟶

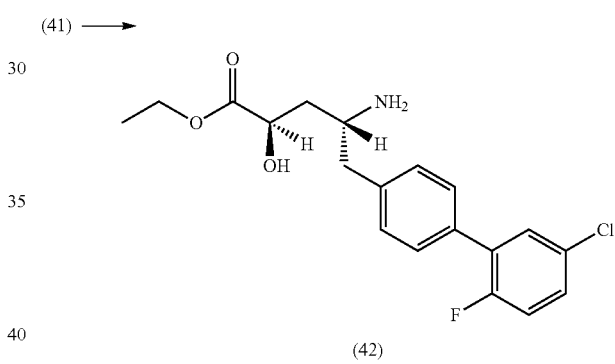

(42)

A solution of Compound 41 (7.5 g, 20.1 mmol) in EtOH/HCl (100 mL) was heated at 50° C. overnight. The mixture was concentrated and the crude product was purified by washing with Et₂O (200 mL) to yield Compound 42 (6.5 g) as a white solid HCl salt. LC-MS: 366.1 [M+H⁺].

Example 5: (2R,4R)-5-(5'-Chloro-T-fluorobiphenyl-4-yl)-4-(ethoxyoxalylamino)-2-hydroxypentanoic Acid (Comparison Compound C5)

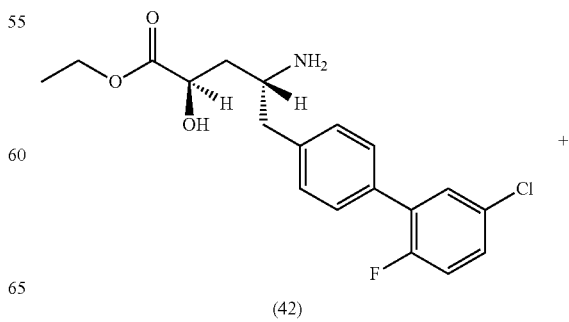

(42)

-continued

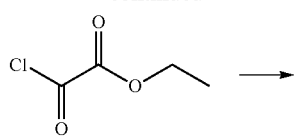

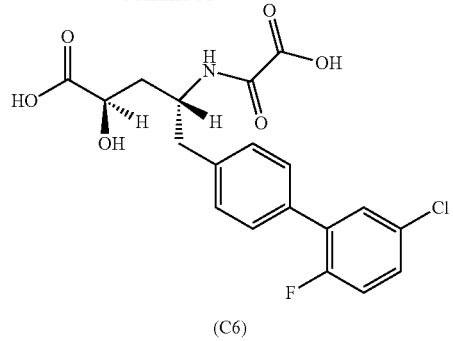

(C6)

(2R,4R)-5-(5'-chloro-2'-fluorobiphenyl-4-yl)-4-(ethoxyoxalylamino)-2-hydroxypentanoic acid (C5) was combined with 1M of LiOH in water (2.5 mL, 2.5 mmol). The mixture was stirred at room temperature for 1 hour at which point LCMS showed reaction completion. The solvent was removed in vacuo to yield Comparison Compound C6 (20.8 mg). MS m/z [M+H]$^+$ calc'd for $C_{19}H_{17}ClFNO_6$, 410.07. found 410.0.

Comparison Compound C6 is described in example 5-5 of U.S. Pat. No. 8,691,868 to Hughes et al.

1.0 N HCl (6 mL) was added to (2R,4R)-4-amino-5-(5'-chloro-2'-fluorobiphenyl-4-yl)-2-hydroxypentanoic acid ethyl ester (42) (114 mg, 313 µmol) and the mixture was stirred at 90° C. for 24 hours then concentrated under reduced pressure. The zwitterion product was combined with Et$_3$N (157 µL, 1.1 mmol) in DCM (6 mL), followed by the addition of a solution of ethyl oxalyl chloride (34.9 µL, 313 µmol) in DCM (2 mL) at 0° C., and the resulting mixture was stirred at room temperature for 30 minutes. Saturated aqueous NaHCO$_3$ (5 mL) was added and the mixture was stirred at room temperature for 1 hour. The mixture was extracted with DCM (3×3 mL) and concentrated and the residue was purified by preparative HPLC to yield Comparison Compound C5 (5 mg). MS m/z [M+H]$^+$ calc'd for $C_{21}H_{21}ClFNO_6$, 438.10. found 438.2.

Comparison Compound C5 is described in example 5-14 of U.S. Pat. No. 8,691,868 to Hughes et al.

Example 7: Stability Study of Crystals of Calcium (2S,4R)-5-(5'-Chloro-2'-fluoro-[1,1'-biphenyl]-4-yl)-4-(2-ethoxy-2-oxoacetamido)-2-(hydroxymethyl)-2-methylpentanoate (1')

One challenge in pharmaceutical drug development relates to discovering a stable, crystalline form of a drug having a reasonably high melting point. The challenge of the present invention was that crystals of the free acid of Compound 1 could not be obtained. Furthermore, many crystal screens failed, with the exception of two-arginine and calcium crystals of (2S,4R)-5-(5'-chloro-2'-fluorobiphenyl-4-yl)-4-(ethoxyoxalylamino)-2-hydroxymethyl-2-methylpentanoic acid were obtained. However, the arginine crystals (see Example 1) were deliquescent at ambient conditions and were difficult to develop further. On the other hand, the calcium crystals were stable and melted around 239° C. For that reason, an accelerated stability study of Compound 1' was conducted at the temperatures and % relative humidity (RH) reported below.

Example 6: (2R,4R)-5-(5'-Chloro-T-fluorobiphenyl-4-yl)-2-hydroxy-4-(oxalylamino)pentanoic Acid (Comparison Compound C6)

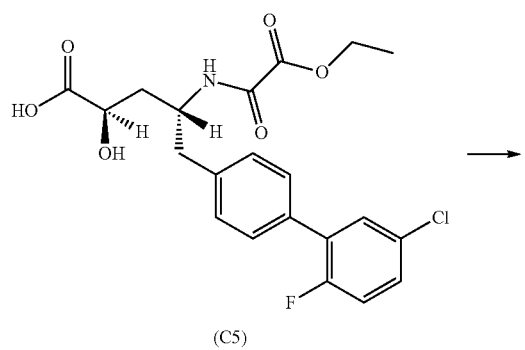

(C5)

| Time | 25° C., 60% RH | | 40° C., 75% RH | | 5° C. | |
|---|---|---|---|---|---|---|
| (months) | Assay$^a$ | Purity$^b$ | Assay | Purity | Assay | Purity |
| 0 | 95.0 | 97.3 | 95.0 | 97.3 | 95.0 | 97.3 |
| 1 | nt$^c$ | nt | 95.5 | 95.9 | nt | nt |
| 2 | 94.4 | 97.3 | 92.1 | 95.3 | 93.4 | 97.6 |
| 3 | 92.9 | 96.8 | 92.1 | 93.9 | 92.4 | 97.5 |

$^a$Assay = (mass substance/total mass) * 100 = % (w/w).
$^b$Purity = (AUC of pure substance/AUC of impure substance) * 100 = % (a/a).
$^c$nt = not tested.

These data demonstrate that Compound 1' remains relatively stable up to at least three months at the temperatures and relative humidity tested.

Assays

Compound 1 and Comparison Compounds C2, C3, C4, C5, and C6 were evaluated in the assays described below.

The following table illustrates metabolites that may be formed from one or more compounds being cleaved at various locations on its structure.

| Compound or Prodrug → | Active Metabolite |
|---|---|
| Compound 1 | Comparison Compound C2 |
| Comparison Compound C3 | Comparison Compound C2 |
| Comparison Compound C4 | Comparison Compound C6 |
| Comparison Compound C5 | Comparison Compound C6 |

Assay 1: In Vitro Assays for the Quantitation of Inhibitor Potencies at Human and Rat NEP The inhibitory activities at human and rat neprilysin (EC 3.4.24.11; NEP) were determined using in vitro assays as described below.

Extraction of NEP Activity from Rat Kidneys

Rat NEP was prepared from the kidneys of adult Sprague Dawley rats. Whole kidneys were washed in cold phosphate buffered saline (PBS) and brought up in ice-cold lysis buffer (1% Triton X-114, 150 mM NaCl, 50 mM tris(hydroxymethyl) aminomethane (Tris) pH 7.5; Bordier (1981) *J. Biol. Chem.* 256: 1604-1607) in a ratio of 5 mL of buffer for every gram of kidney. Samples were homogenized on ice using a polytron hand held tissue grinder. Homogenates were centrifuged at 1000×g in a swinging bucket rotor for 5 minutes at 3° C. The pellet was resuspended in 20 mL of ice cold lysis buffer and incubated on ice for 30 minutes. Samples (15-20 mL) were then layered onto 25 mL of ice-cold cushion buffer (6% w/v sucrose, 50 mM pH 7.5 Tris, 150 mM NaCl, 0.06%, Triton X-114), heated to 37° C. for 3-5 minutes and centrifuged at 1000×g in a swinging bucket rotor at room temperature for 3 minutes. The two upper layers were aspirated off, leaving a viscous oily precipitate containing the enriched membrane fraction. Glycerol was added to a concentration of 50% and samples were stored at −20° C. Protein concentrations were quantitated using a BCA detection system with bovine serum albumin (BSA) as a standard.

Enzyme Inhibition Assays

Recombinant human NEP was obtained commercially (R&D Systems, Minneapolis, Minn., catalog number 1182-ZN). The fluorogenic peptide substrate Mca-D-Arg-Arg-Leu-Dap-(Dnp)-OH (Medeiros et al. (1997) *Braz. J. Med. Biol. Res.* 30:1157-62; Anaspec, San Jose, Calif.) was used.

The assays were performed in 384-well white opaque plates at 37° C. using the fluorogenic peptide substrate at a concentration of 10 μM in Assay Buffer (50 mM HEPES, pH 7.5, 100 mM NaCl, 0.01% polyethylene glycol sorbitan monolaurate (Tween-20), 10 μM $ZnSO_4$). The respective enzymes were used at concentrations that resulted in quantitative proteolysis of 1 μM of substrate after 20 minutes at 37° C.

Test compounds were assayed over the range of concentrations from 10 μM to 20 pM. Test compounds were added to the enzyme and incubated for 30 minute at 37° C. prior to initiating the reaction by the addition of substrate. Reactions were terminated after 20 minutes of incubation at 37° C. by the addition of glacial acetic acid to a final concentration of 3.6% (v/v).

Plates were read on a fluorometer with excitation and emission wavelengths set to 320 nm and 405 nm, respectively. Inhibition constants were obtained by nonlinear regression of the data using the equation (GraphPad Software, Inc., San Diego, Calif.):

$$v = v_0/[1+(I/K')]$$

where v is the reaction rate, $v_0$ is the uninhibited reaction rate, I is the inhibitor concentration and K' is the apparent inhibition constant.

| Compound | rat $pK_i$ | human $pK_i$ |
|---|---|---|
| 1 | 9.1 | 9.1 |
| C2 | 9.5 | 9.2 |
| C3 | 5.7 | 5.4 |
| C4 | 8.1 | 7.8 |
| C5 | 9.7 | 9.7 |
| C6 | 9.8 | 9.7 |

These data show that Compound 1 has potency at rat and human NEP similar to Comparison Compound C2 whereas Comparison Compound C3 has a very low potency at the rat and human NEP enzyme compared to that of Comparison Compound C2. Likewise, Comparison Compound C5 has potency at rat and human NEP similar to Comparison Compound C6 whereas Comparison Compound C4 has a low potency at the rat and human NEP enzyme compared to that of Comparison Compound C6.

Compounds 1, C2, C5, and C6 have significant activity at the rat and human NEP enzyme and meet the activity threshold of pKi ≥9.0 to be useful as a therapeutic use as described above.

Assay 2: PO Pharmacokinetic Study in Rats, Dogs, and Monkeys

Each rat, dog, or monkey pharmacokinetic study began with formulation of the test compound. Appropriate masses of each test compound were added into a volume of vehicle (e.g. 5% sodium bicarbonate, 5% dextrose in water) such that the final concentration of each compound was appropriate to be dosed at 2 mL/kg. Although a homogenous suspension was acceptable for oral dosing, intravenous dosing solutions were sterile-filtered (0.2 μm) prior to dosing to ensure no particulates were administered.

In the rat study, pre-cannulated male Sprague-Dawley rats (3 per route) between 8 and 10 weeks of age were obtained from Harlan Laboratories (Indianapolis, Ind.). Rats received either a single oral gavage or a single intravenous (via lateral tail vein) dose of the dosing solution. The final dose was typically 0.5-3 mg/kg. Serial blood samples were harvested via the cannula implanted in the jugular vein at 3 minutes, 15 minutes, 30 minutes, 1 hour, 2 hours, 4 hours, 6 hours, and 24 hours post-dose. Sampling was performed either manually or using automated blood samplers. Samples were collected into microtainer tubes containing sodium fluoride, potassium oxalate and paraoxon (anticoagulants and esterase inhibitor, respectively), and were processed to plasma by refrigerated centrifugation.

In the dog study, male beagle dogs (3 per route) housed at Agilux Laboratories (Worcester, Mass.) and weighing between 7-12 kg received a single oral gavage dose of the dosing solution. The final dose was typically 0.1-2 mg/kg. Serial blood samples were harvested via direct venipuncture at 3 minutes, 15 minutes, 30 minutes, 1 hour, 2 hours, 4 hours, 6 hours, 8 hours, 12 hours, and 24 hours post-dose. All samples were collected manually into microtainer tubes containing sodium fluoride, potassium oxalate and paraoxon, and were processed to plasma by refrigerated centrifugation.

In the monkey study, male cynomolgus monkeys (3 per route) housed at Xenometrics (Stilwell, Kans.) and weighing between 4-5 kg, received a single oral gavage dose of the dosing solution. The final dose was 2 mg/kg. Serial blood samples were collected from the cephalic or saphenous veins prior to dose administration and 5 minutes, 15 minutes, 30 minutes, 1 hour, 2 hours, 4 hours, 8 hours, 12 hours, and 24 hours post-dose. All samples were collected into tubes containing potassium oxalate, sodium fluoride and paraoxon, and were processed to plasma by refrigerated centrifugation.

Plasma samples were extracted with 3 volumes of MeCN containing a suitable internal standard. Extracts were reconstituted into 3 volumes of water containing 1% formic acid, and analyzed via HPLC-coupled MS/MS. Plasma concentration-time data were analyzed using the Phoenix software (Pharsight Corp., St. Louis, Mo.) to calculate pharmacokinetic parameters.

Oral bioavailability (% F) represents the percentage of a dose that reaches the systemic circulation after an oral dose when compared to an intravenous dose where the entire dose is administered directly into the systemic circulation. It is equal to the ratio of the area under the concentration-time curve after an oral dose to the area under the concentration-time curve after an intravenous dose, normalized for any differences in dose levels between routes.

| Species | Comparison Compound C2 | | Compound 1 | |
|---|---|---|---|---|
| | $AUC_{last}$[a] (μg*hr/mL) (normalized)[b] | Oral Bioavailabilty (% F) | $AUC_{last}$[a] (μg*hr/mL) (normalized)[b] | Oral Bioavailabilty % F |
| rat | 0.45 | 33 | 3.4 | >100 |
| dog | 0.27 | 13 | 0.89 | 44 |
| monkey | 0.82 | 1.7 | 7.4 | 77 |

[a]$AUC_{last}$ is the area under the plasma concentration versus time curve from time 0 to the time after dosing at which the last quantifiable concentration was observed, estimated by linear trapezoidal method
[b]Normalized by dividing $AUC_{last}$ by the administered dose These data show that Comparison Compound C2 (active metabolite of Compound 1) has low oral bioavailability while Compound 1 has relatively high oral bioavailability in all three animal models tested.

Assay 3: IV/PO Pharmacokinetic Study in Rats and Dogs

Each rat or dog pharmacokinetic study began with formulation of the test compound. Appropriate masses of each test compound were added into a volume of vehicle (e.g. 5% sodium bicarbonate, 5% dextrose in water) such that the final concentration of each compound was appropriate to be dosed at 2 mL/kg. Although a homogenous suspension were acceptable for oral dosing, intravenous dosing solutions were sterile-filtered (0.2 μm) prior to dosing to ensure no particulates were administered.

In the rat study, pre-cannulated male Sprague-Dawley rats (3 per route) between 8 and 10 weeks of age were obtained from Harlan Laboratories (Indianapolis, Ind.). Rats received either a single oral gavage or a single intravenous (via lateral tail vein) dose of the dosing solution. The final dose was typically 0.5-3 mg/kg. Serial blood samples were harvested via the cannula implanted in the jugular vein at 3 minutes, 15 minutes, 30 minutes, 1 hour, 2 hours, 4 hours, 6 hours, and 24 hours post-dose. Sampling was performed either manually or using automated blood samplers. Samples were collected into microtainer tubes containing sodium fluoride, potassium oxalate and paraoxon, and were processed to plasma by refrigerated centrifugation.

In the dog study, male beagle dogs (3 per route) housed at Agilux Laboratories (Worcester, Mass.) and weighing between 7-12 kg received either a single oral gavage or a single intravenous (via indwelling catheter) dose of the dosing solution. The final dose was typically 0.1-2 mg/kg. Serial blood samples were harvested via direct venipuncture at 3 minutes, 15 minutes, 30 minutes, 1 hour, 2 hours, 4 hours, 6 hours, 8 hours, 12 hours, and 24 hours post-dose. All samples were collected manually into microtainer tubes containing sodium fluoride, potassium oxalate and paraoxon, and were processed to plasma by refrigerated centrifugation.

Plasma samples were extracted with 3 volumes of MeCN containing a suitable internal standard. Extracts were reconstituted into 3 volumes of water containing 1% formic acid, and analyzed via HPLC-coupled MS/MS. Plasma concentration-time data were analyzed using the Phoenix software (Pharsight Corp., St. Louis, Mo.) to calculate pharmacokinetic parameters.

| Rat Pharmacokinetic Data | | | | | |
|---|---|---|---|---|---|
| Compound Dosed | Route | Analyte | $AUC_{last}$[a] (μg*hr/mL) | | Oral Bioavailability[b] of Active Metabolite |
| | | | Mean | CV | Mean |
| 1 | PO | 1 | 0 | NA | NA |
| 1 | PO | C2 | 15 | 18% | >100% |
| C2 | IV | C2 | 16 | 32% | NA |
| C3 | PO | C3 | 0.56 | 20% | NA |
| C3 | PO | C2 | 0.67 | 20% | 21% |
| C2 | IV | C2 | 16 | 32% | NA |
| C5 | PO | C5 | 0 | NA | NA |
| C5 | PO | C6 | 0.62 | 12% | 11% |
| C6 | IV | C6 | 15 | 17% | NA |
| C4 | PO | C4 | 0.04 | 32% | NA |
| C4 | PO | C6 | 0.59 | 34% | 9% |
| C6 | IV | C6 | 15 | 17% | NA |

[a]$AUC_{last}$ is the area under the plasma concentration versus time curve from time 0 to the time after dosing at which the last quantifiable concentration was observed, estimated by linear trapezoidal method
[b]Oral Bioavailability is calculated as $AUC_{last}$ of the active molecule following oral administration of the prodrug, divided by $AUC_{last}$ following intravenous administration of the active molecule, normalized for any differences in administered doses, expressed as a percentage.

These rat data show that the compound of the invention, Compound 1, results in significantly greater systemic exposure of its active metabolite than either Compound C3, C5 or C4 (metabolite bioavailability values of >100%, 21%, 11% and 9%, respectively).

| Active Metabolite | Compound or Prodrug | Active AUC$_{last}$/ Prodrug AUC$_{last}$ |
|---|---|---|
| C2 | 1 | No Prodrug Detected |
| C2 | C3 | 1.2 |
| C6 | C5 | No Prodrug Detected |
| C6 | C4 | 17 |

For both Compound 1 and Comparison Compound C5, no prodrug was detected so it may be assumed that complete conversion of prodrug compounds to active metabolite occurred in vivo in the rat. Both of these compounds have metabolite exposure ratios greater than either Comparison Compound C4 (17) or Comparison Compound C3 (1.2).

These prodrugs cleave by ester hydrolysis, which often occurs more rapidly in rats than in dogs or humans. For that reason, the rat model of ester hydrolysis is not always predictive of cleavage in humans. Thus, prodrugs like that of the invention should also be evaluated in dogs to get additional predictive data for estimation of cleavage rates in humans.

Dog Pharmacokinetic Data

| Compound Dosed | Route | Analyte | AUC$_{last}$ (μg*hr/mL) Mean | CV | Oral Bioavailability of Active Metabolite Mean |
|---|---|---|---|---|---|
| 1 | PO | 1 | 0.0037 | 37% | NA |
| 1 | PO | C2 | 0.65 | 30% | 44% |
| C2 | IV | C2 | 1.97 | 5% | NA |
| C3 | PO | C3 | 0.95 | 3% | NA |
| C3 | PO | C2 | 0 | 0% | 0% |
| C2 | IV | C2 | 1.97 | 5% | NA |
| C5 | PO | C5 | 0.029 | 26% | NA |
| C5 | PO | C6 | 0.37 | 19% | 29% |
| C6 | IV | C6 | 1.28 | 26% | NA |
| C4 | PO | C4 | 0.48 | 33% | NA |
| C4 | PO | C6 | 0.59 | 17% | 46% |
| C6 | IV | C6 | 1.28 | 26% | NA |

These canine data show that the compound of the invention, Compound 1, results in similar oral bioavailability of its active metabolite to Comparison Compound C4 and much greater bioavailability than either Compound C3 or C5 (values of 44%, 46%, 0% and 29%, respectively).

| Active Metabolite | Compound or Prodrug | Active AUC$_{last}$/ Prodrug AUC$_{last}$ |
|---|---|---|
| C2 | 1 | 177 |
| C2 | C3 | 0 |
| C6 | C5 | 13 |
| C6 | C4 | 1.2 |

These canine data show that the prodrug of the invention, Compound 1, yields a significantly greater relative exposure to its active metabolite molecule (i.e., AUC$_{last}$) than any of the other compounds or prodrugs tested. Such rapid and extensive prodrug hydrolysis provides a significant and surprising advantage to the compound of the invention. In the dog, Compound 1 cleaves much more efficiently than Comparison Compound C5, resulting in more than a 10-fold improvement in exposure ratio (177 versus 13). Moreover, Compound 1 cleaves even more efficiently when compared with Comparison Compound C3 (exposure ratios of 177 versus 0). The magnitude of this difference could not have been predicted based on the comparison of the extent of hydrolysis of Comparison Compound C5 as compared with C4 (13 versus 1.2).

Assay 4: Renal Excretion of Compound 1 in Male Beagle Dogs

An important factor for insuring appropriate long term drug dosing and correct steady-state drug concentrations in patients is drug clearance. In general, decreased drug clearance results in higher drug concentrations and greater drug effects. In order to understand renal clearance of Compound 1, the percent of administered dose recovered in urine following a single IV dose was assessed in male beagle dogs as described below.

Male beagle dogs (N=3), having body weights of 9.58-10.42 kg, received an IV dose of 1.0 mg/kg of Compound 1. Compound 1 was formulated in 5% NaHCO$_3$ in D5W. The dogs were fasted overnight and pretreated with pentagastrin (60 μg/mL, 0.1 mL/kg, IM) approximately 30 minutes prior to dose administration to stimulate gastric secretion. Food was returned approximately 4 hours postdose. Urine samples were collected surrounded by cold ice packs during the collection period. After 24 hours, the sample weight was recorded, the sample was thoroughly mixed, and aliquots were obtained and frozen (−80° C.) prior to bioanalysis.

Dog urine concentrations of Compound 1 were determined by LC/MS/MS. Urine study samples (diluted in plasma) were vortexed and 50 μL was placed in a 96-well plate. The samples were extracted with acetonitrile with internal standard chrysin. The extract was centrifuged and supernatant was transferred to a new 96-well plate and diluted 1 part sampe in 4 parts water with 0.2% formic acid. Samples (12 μL) were injected on a Waters Acquity UPLC BEH C18 (50×2.1 mm, 1.7 μm) column with a flow rate of 0.9 mL/min. Mobile phase A consisted of 95:5:0.1 (v:v:v) water:acetonitrile:formic acid and mobile phase B consisted of 50:50:0.1 (v:v:v) methanol:acetonitrile:formic acid. Compound 1 assay range was 0.001 to 5.00 μg/mL.

The mean amount of urine excreted over a collection period of 24 hrs and the approximate % of administered dose excreted in urine is reported in the table below.

| Species | Amount of IV Administration (mg/kg) | Amount of Compound 1 Excreted in Urine over Collection Period (0-24 hrs) (μg) Mean[a] | Urinary Excretion (approximate % of administred dose excreted in urine) Mean[a] |
|---|---|---|---|
| Dog | 1.0 | 28.9 | 0.284% |

[a]Average of three determinations

The renal excretion of Compound 1 in the dog was approximately <0.5% of the administered dose. This data indicates that Compound 1 has low renal excretion in male beagle dogs.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents, and patent applications cited herein are hereby incorporated by reference in their entirety to the same extent as if each document had been individually incorporated by reference herein.

What is claimed is:

1. An arginine crystalline form of the compound:

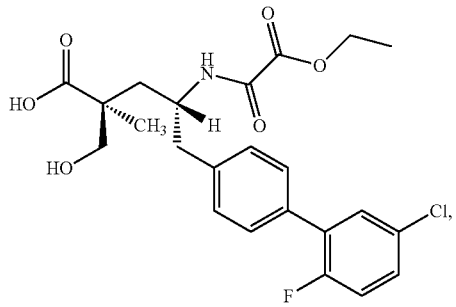

wherein the arginine crystalline form is characterized by a differential scanning calorimetry profile which shows a maximum in endothermic heat flow at a temperature in the range of about 113° C. and about 117° C.

Figure 6:
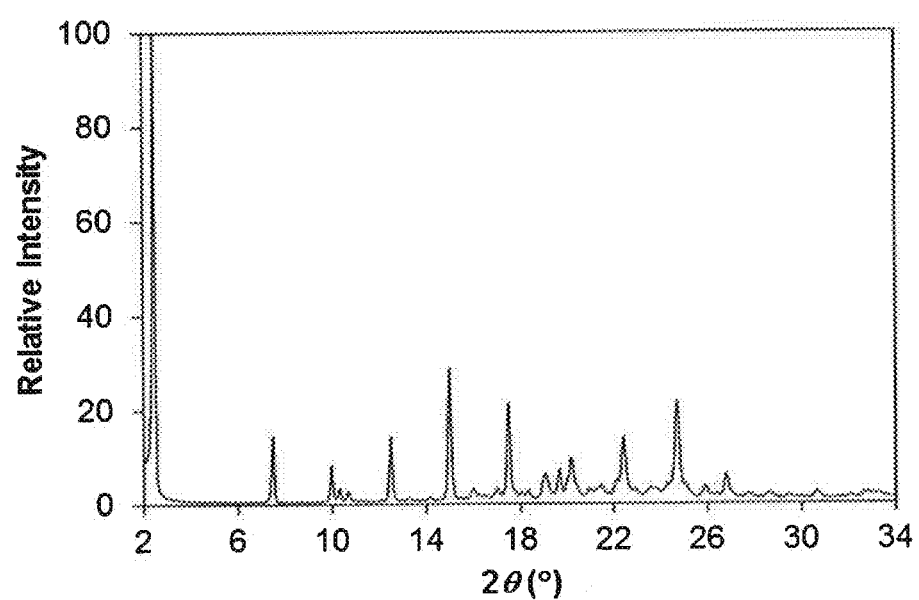
FIG. 6 shows a powder X-ray diffraction (PXRD) pattern of the crystalline form of arginine (2S,4R)-5-(5'-chloro-2'-fluoro-[1,1'-biphenyl]-4-yl)-4-(2-ethoxy-2-oxoacetamido)-2-(hydroxymethyl)-2-methylpentanoate (1").
Figure 7:
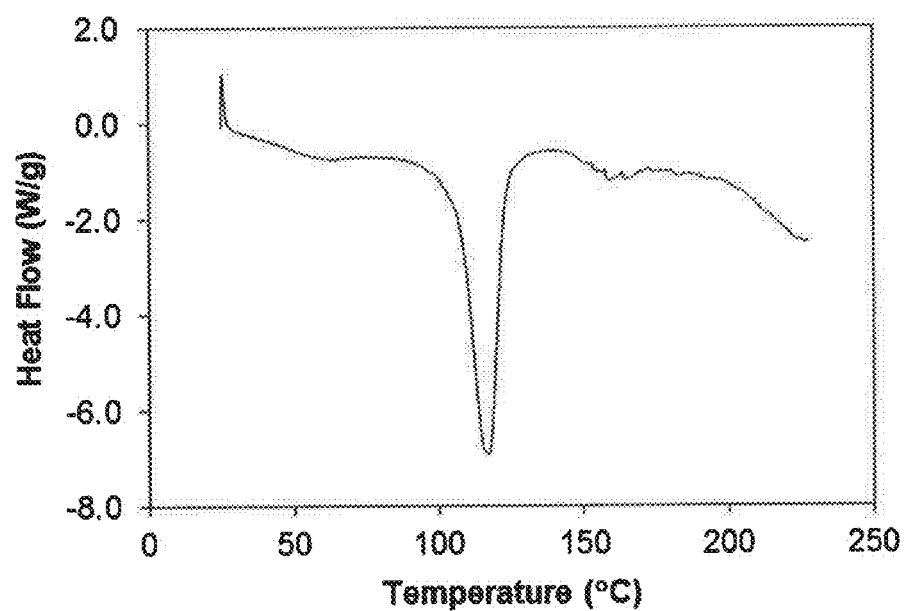
FIG. 7 shows a differential scanning calorimetry (DSC) thermogram of the crystalline form of arginine (2S,4R)-5-(5'-chloro-2'-fluoro-[1,1'-biphenyl]-4-yl)-4-(2-ethoxy-2-oxoacetamido)-2-(hydroxymethyl)-2-methylpentanoate (1").

2. An arginine crystalline form of the compound:

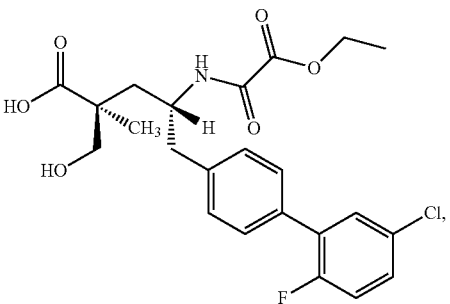 [SMILES: CCOC(=O)C(=O)N[C@H](Cc1ccc(-c2cc(Cl)ccc2F)cc1)C[C@@](C)(CO)C(=O)O]

wherein the arginine crystalline form is characterized by a powder X-ray diffraction pattern in which the peak positions are substantially in accordance with the peak positions of the pattern shown in FIG. 6 and by a differential scanning calorimetry profile substantially in accordance with that shown in FIG. 7.

* * * * *